United States Patent [19]
Handa et al.

[11] Patent Number: 5,876,715
[45] Date of Patent: Mar. 2, 1999

[54] ANTIBODIES THAT BIND NOVEL CARBOHYDRATE LIGANDS (MYELOROLLINS) THAT CAUSE E-SELECTIN DEPENDENT CELL ROLLING, AND USES THEREOF

[75] Inventors: Kazuko Handa, Bellevue; Mary Ellen K. Salyan, Silverdale; Mark R. Stroud, Seattle; Sen-itiroh Hakomori, Mercer Island, all of Wash.

[73] Assignees: The Biomembrane Institute, Seattle, Wash.; Seikagaku Corporation, Tokyo, Japan

[21] Appl. No.: 635,849

[22] Filed: Apr. 22, 1996

Related U.S. Application Data

[63] Continuation-in-part of Ser. No. 516,174, Aug. 17, 1995, abandoned.

[51] Int. Cl.$^6$ .................. A61K 39/395; C07K 16/00
[52] U.S. Cl. .................. 424/130.1; 514/54; 530/387.5
[58] Field of Search .................. 424/137.1; 514/54; 530/387.5

[56] References Cited

U.S. PATENT DOCUMENTS

| | | | |
|---|---|---|---|
| 4,851,511 | 7/1989 | Hakomori et al. | 530/387.5 |
| 5,011,920 | 4/1991 | Hakomori et al. | 536/53 |
| 5,198,424 | 3/1993 | McEver | 514/13 |
| 5,211,936 | 5/1993 | Brandley et al. | 424/1.73 |
| 5,227,369 | 7/1993 | Rosen et al. | 514/23 |
| 5,268,364 | 12/1993 | Kojima et al. | 514/25 |
| 5,316,913 | 5/1994 | Butcher et al. | 435/7.24 |
| 5,326,752 | 7/1994 | Nashed et al. | 514/25 |
| 5,369,017 | 11/1994 | Wong et al. | 435/68.1 |
| 5,369,096 | 11/1994 | Yamada et al. | 514/61 |
| 5,412,123 | 5/1995 | Rao et al. | 552/209 |
| 5,418,129 | 5/1995 | Nudelman et al. | 435/2 |
| 5,426,178 | 6/1995 | Laine et al. | 536/1.11 |
| 5,464,778 | 11/1995 | Cummings et al. | 436/503 |

FOREIGN PATENT DOCUMENTS

| | | | |
|---|---|---|---|
| 0 344 955 A | 12/1989 | European Pat. Off. | |
| WO 91/19501 | 12/1991 | WIPO | A61K 31/70 |
| WO 91/19502 | 12/1991 | WIPO | A61K 31/70 |

OTHER PUBLICATIONS

Alon et al., 1995, *J. Immunol.* 154:5356–5366.
Asada et al., 1991, *Biochem.* 30:1561–1571.
Atkins et al., 1974, *Polymer* 15:263–271.
Berg et al., 1991, *J. Biol. Chem.* 266:14869–14872.
Fukuda et al., 1979, *J. Biol. Chem.* 254:5458–5465.
Fukuda et al., 1984, *J. Biol. Chem.* 259: 10925–10935.
Fukushi et al., 1984, *J. Biol. Chem.* 259:10511–10517.
Fukushima et al., 1984, *Cancer Res.* 44:5279–5285.
Handa et al., 1991, *Biochem. Biophys. Res. Comm.* 181:1223–1230.
Handa et al., 1995, *Int. J. Oncol.* 6:773–781.
Ito et al., 1994, *Glycoconj. J.* 11:232–237.
L.A. Lasky, 1995, *Ann. Rev. Biochem.* 64:113–139.
Lawrence et al., 1987, *Blood* 70:1284–1290.
Lawrence et al., 1990, *Blood* 75:227–237.
Lawrence & Springer, 1991, *Cell* 65:859–873.
Lowe et al., 1991, *J. Biol. Chem.* 266:17467–17477.
Mulligan et al., 1993, *J. Exp. Med.* 178:623–631.
Muroi et al., 1992, *Blood* 79:713–719.
Niemann et al., 1978, *Biochem. Biophys. Res. Comm.* 81:1286–1293.
Nudelman et al., 1988, *J. Biol. Chem.* 263:13942–13951.
Osanai et al., 1996, *Biochem. Biophys. Res. Comm.* 218:610–615.
Patel et al., 1994, *Biochem.* 33:14815–14824.
Phillips et al., 1990, *Science* 250:1130–1132.
Polley et al., 1991, *PNAS USA* 88:6224–6228.
Rees, D.A., 1975, *MTP International Rev. of Science*, W.J. Whelan, ed., Butterworths (London), Univ. Park Press (Baltimore) 5:1–42.
Sako et al., 1993, *Cell* 75:1179–1186.
Stroud et al., 1995, *Biochem. Biophys. Res. Comm.* 209:777–787.
Stroud et al., 1996, *Biochem.* 35:758–769.
Stroud et al., 1996, *Biochem.* 35:770–778.
Takada et al., 1991, *Biochem. Biophys. Res. Comm.* 179:713–719.
Tiemeyer et al., 1991, *PNAS USA* 88:1138–1142.
A. Varki, 1994, *PNAS USA* 91:7390–7397.
Walz et al., 1990, *Science* 250:1132–1135.
Yang & Hakomori, 1971, *J. Biol. Chem.* 246:1192–1200.
Brandley et al. Cell 63, 861–863, 1990.
Tyrell et al. Proc. Natl. Acad. Sci. USA 88, 10372–10376, 1991.
Macher et al. J. Biol. Chem. 263, 10186–10191, 1988.

*Primary Examiner*—Stephen Walsh
*Assistant Examiner*—Elizabeth C. Kemmerer
*Attorney, Agent, or Firm*—Pennie & Edmonds, LLP

[57] ABSTRACT

The invention relates to antibodies that specifically bind a myelorollin comprising an unbranched polylactosamine comprising at least 10 monosaccharides and having terminal α2→3 sialylation and internal α1→3 fucosylation at various N-acetylglucosamine residues except the penultimate N-acetylglucosamine residue. The invention also relates to a method of using such antibodies to inhibit E-selectin-dependent rolling of a cell on another cell, wherein one of the cells expresses a myelorollin that binds the antibodies.

6 Claims, 25 Drawing Sheets

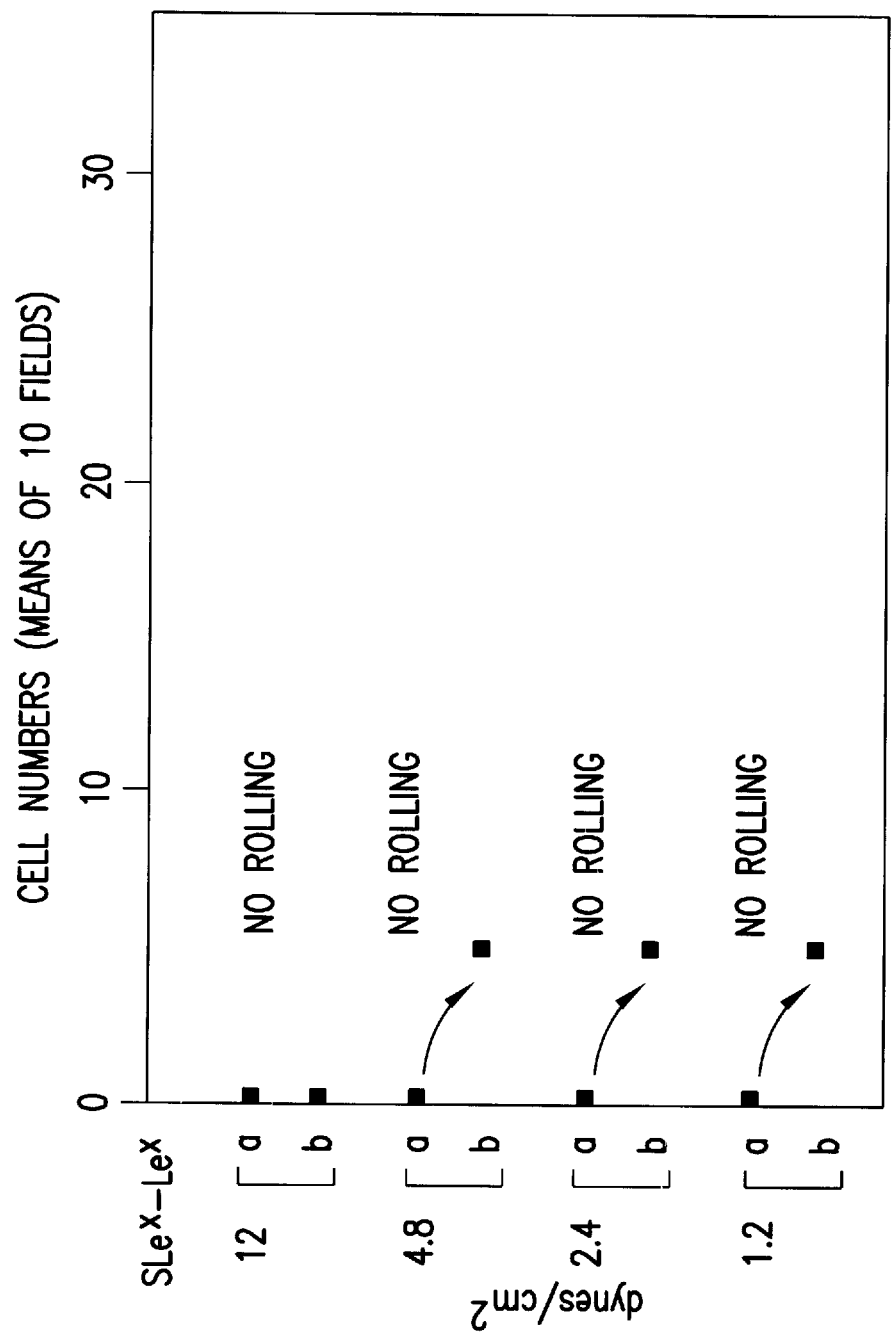

Structures of myeloglycan type and related gangliosides.

| Str. # | name | structure |
|---|---|---|
| 1 | SLe$^x$-Le$^x$ | Galβ4GlcNAcβ3Galβ4Glcβ1Cer<br>3　　3<br>NeuAcα　Fucα |
| 2 | Fr. 13-1 | Galβ4GlcNAcβ3Galβ4GlcNAcβ3Galβ4Glcβ1Cer<br>3　　　　　　　　　　　3<br>NeuAcα　　　　　　　　　　Fucα |
| 3 | Fr. 14 | Galβ4GlcNAcβ3Galβ4GlcNAcβ3Galβ4GlcNAcβ3Galβ4Glcβ1Cer<br>3　　　　　　　　　　　　　　　　　　　　　　3<br>NeuAcα　　　　　　　　　　　　　　　　　　　　　Fucα |
| 4 | Fr. 14 | Galβ4GlcNAcβ3Galβ4GlcNAcβ3Galβ4GlcNAcβ3Galβ4GlcNAcβ3Galβ4Glcβ1Cer<br>3　　　　　　　　　　　　　　　　　　　　　　　　　　　　　　3<br>NeuAcα　　　　　　　　　　　　　　　　　　　　　　　　　　　　Fucα |
| 5 | Fr. 14 | Galβ4GlcNAcβ3Galβ4GlcNAcβ3Galβ4GlcNAcβ3Galβ4GlcNAcβ3Galβ4GlcNAcβ3Galβ4Glcβ1Cer<br>3　　　　　　　　　　　　　　　　　　　　　　　　　　　　　　　　　　　　　3<br>NeuAcα　　　　　　　　　　　　　　　　　　　　　　　　　　　　　　　　　　　Fucα |
| 6 | Fr. 14 | Galβ4GlcNAcβ3Galβ4GlcNAcβ3Galβ4GlcNAcβ3Galβ4GlcNAcβ3Galβ4GlcNAcβ3Galβ4GlcNAcβ3Galβ4Glcβ1Cer<br>3　　　　　　　　　　　　　　　　　　　　　　　　　　　　　　　　　　　　　　　　　　　3<br>NeuAcα　　　　　　　　　　　　　　　　　　　　　　　　　　　　　　　　　　　　　　　　　Fucα |

FIG. 8A

ANTIBODIES THAT BIND NOVEL CARBOHYDRATE LIGANDS (MYELOROLLINS) THAT CAUSE E-SELECTIN DEPENDENT CELL ROLLING, AND USES THEREOF

This application is a continuation-in-part of application Ser. No. 08/516,174, filed Aug. 17, 1995, now abandoned the entire disclosure of which is incorporated herein by reference.

FIELD OF THE INVENTION

The present invention relates to a group of compounds having saccharide sequences that cause, under dynamic flow conditions, E-selectin dependent rolling and adhesion stronger that $SLe^x$-$Le^x$. The present invention relates to the presence of a group of monosialofucogangliosides that cause E-selectin dependent rolling and adhesion. The invention is based on the discovery that novel carbohydrate ligands (called "myelorollin") expressed on leukocytes and leukemic cells mediate E-selectin dependent rolling and adhesion to activated endothelial cells at sites of inflammation under dynamic flow conditions. Myelorollin is a group of unbranched polyactosamine compounds having $\alpha2\rightarrow3$ sialosyl residue at the terminus and $\alpha1\rightarrow3$ fucosyl residues at the internal GlcNAc but not at the penultimate GlcNAc. The invention is also based on the fact that a mixture of different types of myelorollins showed a synergistic rolling and adhesion effect on E-selectin under dynamic flow conditions. In this specification, unless otherwise indicated, 'rolling' includes plain rolling, rolling followed by adhesion and adhesion followed by rolling and 'adhesion' means plain adhesion without any accompaniment of rolling.

BACKGROUND OF THE INVENTION

The following abbreviations are used throughout this disclosure: BSA, bovine serum albumin; CID, collision-induced dissociation; CHO cells, Chinese hamster ovary cells; EC, endothelial cell; EDTA, ethylenediaminetetra acetic acid; ES-MS, electrospray mass spectrometry; FABMS, fast atom bombardment mass spectrometry; Fr., fraction(s); GSL, glycosphingolipid; Ig, immunoglobulin; IHW, isopropanol/hexane/water; mAb, monoclonal antibody; MFI, mean fluorescence intensity; NMR, nuclear magnetic resonance; PLA, polylactosamine; PBS, phosphate-buffered saline; $Sdiy^2$ or $SLe^x$-$Le^x$, sialosyl $Le^x$-$Le^x$; $SLe^x$, sialosyl-$Le^x$; $SLe^a$, sialosyl-$Le^a$, Str., structure(s); TLC, thin layer chromatography. Glycolipids are abbreviated according to the recommendations of the IUPAC-IUB Commission on Biochemical Nomenclature (Lipids 12:455–463, 1977); however, the suffix -OseCer is shortened to -Cer. In particular, sialosyl-$Le^x$ and sialosyl$Le^x$-$Le^x$ have the following structures:

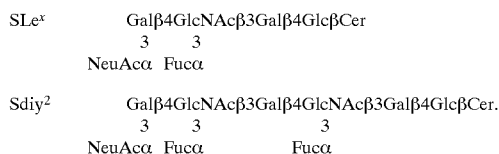

As illustrated in the formulas above, the number "1" to show the glycoside-OH position in saccharide and the arrow to show the bond to adjacent saccharide is, unless otherwise indicated, omitted for abbreviation purpose in this specification.

Since 1989, cloning of vascular or platelet adhesive proteins, now termed "selectins," has led to focused attempts to identify carbohydrate epitopes which are expressed on leukocytes (Varki, A., 1994, Proc. Natl. Acad. Sci. USA 91:7390–7397; Lasky, L. A., 1995, Ann. Rev. Biochem. 64:113–139) and function as targets of selectin-dependent "rolling" and adhesion of leukocytes on activated endothelial cells, followed by transendothelial migration. This mechanism plays a central role in inflammatory responses (Lasky, L. A., 1995, Ann. Rev. Biochem. 64:113–139). Such epitopes are involved in recruitment of the cells to inflammatory sites following infection or wounding. Currently, sialosyl-$Le^x$ ($SLe^x$) is generally believed to be the target epitope of E-selectin binding, based on the following claims: (i) Human leukocytes, leukemic leukocytes, and leukemic cell lines (e.g., HL60 and U937 cells), but not non-human leukocytes, express $SLe^x$. This claim was based on strong reactivities of these types of cells with mAbs believed to be directed to $SLe^x$ (Ito et al.,1994, Glycoconj. J. 11:232–237). These $SLe^x$-expressing cells adhere to activated endothelial cells or platelets which express E- or P-selectin (Phillips et al., 1990, Science 250:1130–1132; Polley et al., 1991, Proc. Natl. Acad. Sci. USA 88:6224–6228). (ii) Chinese Hamster Ovary (CHO) cells expressing sialosyl type 2 chain do not adhere to E-selectin, whereas transfectants of these cells with fucosyltransferase III cDNA do adhere to E-selectin (Lowe et al., 1991, J. Biol. Chem. 266:17467–17477). (iii) E-selectin-dependent adhesion of $SLe^x$-expressing cells to activated ECs is inhibited by liposomes containing $SLe^x$GSLs, or by oligosaccharides with terminal $SLe^x$ structure (Phillips et al., 1990, Science 250:1130–1132; Polley et al., 1991, Proc. Natl. Acad. Sci. USA 88:6224–6228; Handa et al., 1991, Biochem. Biophys. Res. Commun. 181:1223–1230).

These observations have encouraged acceptance of the idea that $SLe^x$ is the epitope to which E-selectin binds. E- and P-selectin also bind to $SLe^a$, the positional isomer of $SLe^x$ (Handa et al., 1991, Biochem. Biophys. Res. Commun. 181:1223–1230; Berg et al., 1991, J. Biol. Chem. 266:14869–14872; Takada et al., 1991, Biochem. Biophys. Res. Commun. 179:713–719); however, $SLe^a$ is absent in leukocytes and is not considered to be a physiologic epitope of selectins for hematopoietic cells. There has been no systematic characterization of $SLe^x$-containing gangliosides present in neutrophils and HL60 cells, nor any unambiguous demonstration that $SLe^x$ is the major epitope present in N-linked or 0-linked glycoprotein side chains in normal or leukemic leukocytes or cell lines derived therefrom.

It is reported that, in an IgG immune complex model of rat with neutrophil-mediated and E-selectin-dependent lung injury, $SLe^x$ provides protective effects against inflammatory vascular injury (Mulligan, et al., J. Exp. Med. 178:623–631 (1993)).

However, it is also reported that, from the results of immunostaining by antibodies and of indirect binding assay to E- or P-selectin affixed on plate, of human neutrophil (polymorphonuclear leukocytes; PMN), only human PMN and promyelogenous leukemia HL60 cell expressed $SLe^x$ and other lacto-series epitopes, such as Le$^x$ or Le$^y$, but no other mammalian PMN, such as PMN of baboon, macaque, pig, rabbit, rat, guinea pig and hamster (Ito et al., Glycoconj. J. 11:232–237 (1994)). And that the E-selectin ligand saccharide sequences obtained from mouse kidney and murine leukocyte are identified as, Galβ4GlcNAcβ6GalNAcβ3Galα4Galβ4Glcβ1Cer
     3                     3
Fucα1 Galβ1 and

Galβ3GlcNAcβ3Gal
     3        4
NeuAcα2 Fucα1

(Osanai et al., Biochem. Biophys. Res. Commun. 218:610–615 (1996)).

These reports showed that ligands for selectin of mammals other than human beings are not SLe$^x$. And hitherto Galβ4GlcNAcβ3Galβ4GlcCer,
    3        3
NeuAcα2 Fucα1

Galβ4GlcNAcβ3Galβ4GlcNAcβ3Galβ4GlcCer
    3        3
NeuAcα2 Fucα1 and

Galβ4GlcNAcβ3Galβ4GlcNAcβ3Galβ4GlcCer
    3        3        3
NeuAcα2 Fucα1     Fucα1 commonly found in solid tumor cells and tissues does not exist in human neutrophils and HL60 cells and that the following glycolipids,

1   GalβGlcNAcβ3Galβ4GlcNAcβ3Galβ4GlcNAcβ3Galβ4GlcNAcβ3Galβ4GlcCer,
               3                               3
     NeuAcα2          Fucα1

2   Galβ4GlcNAcβ3Galβ4GlcNAcβ3Galβ4GlcNAcβ3Galβ4GlcNacβ3Galβ   4GlcCer,
               3                               3
     NeuAcα2          Fucα1

3   Galβ4GlcNAcβ3Galβ4GlcNAcβ3Galβ4GlcNAcβ3Galβ4GlcNAcβ3Galβ4GlcNacβGalβ4GlcCer,
               3                               3
     NeuAcα2          Fucα1

4   Galβ4GlcNAcβ3Galβ4GlcNAcβ3Galβ4GlcNAcβ3Galβ4GlcNAcβ3Galβ4GlcCer
               3                               3          3
     NeuAcα2          Fucα1      Fucα1 and

5   Galβ4GlcNAcβ3Galβ4GlcNAcβ3Galβ4GlcNAcβ3Galβ4GlcNAcβ3Galβ4GlcCer
               3    3              3             3
     NeuAcα2 Fucα1     Fucα1     ±Fucα1 certified results on anti-inflammatory effects obtained by using animal models have become questionable.

Further, it is disclosed that, when in vitro, liposomes containing the glycolipid;

Galβ4GlcNAcβ3Galβ4GlcNAcβ3Galβ4Glcβ1Cer
    3        3            3
NeuAcα2 Fucα1     Fucα1 are added to activated endothelial cells and thereto HL60 cells are added, binding of HL60 cells to activated endothelial cells are selectively blocked (WO91/19501 and WO91/19502).

Further, it is reported that glycolipids extracted from leukocytes of patients with chronic myelogenous leukemia was either absorbed to polyvinyl chloride microtiter wells or resolved on TLC plates, screened by binding to COS cells expressing endothelial leukocyte adhesion molecule-1 (ELAM-1) and analyzed structurally, so that detected was the glycolipid below:

Galβ4GlcNAcβ3Galβ4GlcNAcβ3Galβ4GlcNAcβ3Galβ4Glcβ1Cer
    3                 3
NeuAcα2         Fucα1

(Proc. Nat. Acad. Sci. USA 88:1138–1142 (1991)).

Further, Stroud et al. (Biochem. Biophys. Res. Commun. 209:777–787 (1995)) reported that the following glycolipids, were extracted from human neutrophils and HL60 cells, developed on TLC and placed into contact with E-selectin expressing CHO cells to detect adhesion, which proved that these cells adhered to the glycolipid #4 including very little amount of #5.

On the other hand, since the rolling-type adhesion between the selectins on vascular endothelium and the oligosaccharide ligands of leukocytes participates in the initiation of the inflammatory response, it is expected to protect from influx of leukocytes into the tissue sites of inflammation and localized damage to endothelium by activated neutrophils via an inhibition of leukocyte rolling along endothelium (Lasky, L. A., Ann. Rev. Biochem. 64:113–139 (1995)).

The currently known E-selectin ligand compounds were selected and proved to be effective under conditions without any shear stress, not taking into consideration the above-mentioned rolling phenomena really occurring in human body. Therefore, these compounds should not be a real E-selectin ligand material. They could control neither E-selectin dependent rolling and adhesion of leukocytes along E-selectin expressing cells, such as endothelium, which is activated in living body nor human inflammation specifically.

It is reported that E-selectin expressing CHO cells tethered under a shear stress of 0.78 dyne/cm$^2$ along the solid phase affixed with SLe$^x$ via egg lecithin phosphatidylcholine (abbreviated as PC). The solid phase used for this experiment was prepared by adding 3 μl of SLe$^x$ (dissolved at 1 μg/ml in 20:1 methanolbutanol solution containing 4 μg/ml PC) to the area having a diameter of 4 mm and drying, whereby, based on the amount added to said solid phase, 15% of SLe$^x$ was affixed via PC to the solid phase (J. Immunol. 154:5356–5366 (1995)). However, as mentioned before, not existing in human neutrophil, SLe$^x$ could not control human inflammation safely and specifically.

SUMMARY OF THE INVENTION

We studied binding of $^{32}$P-labeled CHO cells permanently expressing E-selectin to gangliosides separated on TLC. Only those gangliosides having unbranched polylactosamine with 10- to 12-sugar monosaccharide cores showed binding by this method. The study was extended using a new method under static and dynamic flow conditions. We found that gangliosides containing a novel structure termed "myelorollin" are primarily responsible for E-selectin-dependent rolling and adhesion, particularly under dynamic flow conditions.

The present invention relates to material containing saccharide sequences, such that rolling of E-selectin-expressing cells, such as CHO cells expressing E-selectin, can be observed on solid phase affixed with said saccharide sequence under dynamic flow conditions. The dynamic flow conditions mean those conditions where a physiological shear stress attainable in human body means such as a shear stress caused by blood flow. And said materials should have the saccharide sequence existing in human neutrophils or other cells similar thereto.

Myelorollin is embodied by the following group of non-SLe$^x$-containing structures A, B, C, D and X, Y, which are unbranched polylactosamines with terminal α2→3 sialyation and internal fucosylation at various GlcNAc residues except for the penultimate GlcNAc:

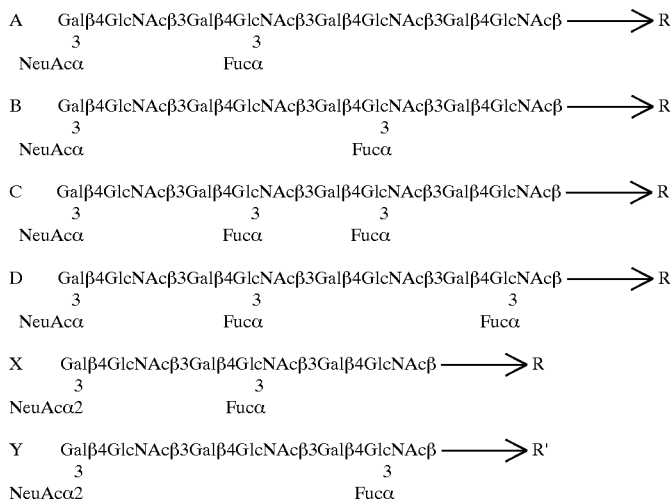

wherein → indicates covalent bond; R is a H atom, a substituted or unsubstituted aryl group, an alkyl, alkenyl or hydroxyalkyl group having 1 to 10 carbon atoms, a complex lipid, a simple lipid, an oligosaccharide, a ceramide residue, a pharmaceutically active ingredient, a solid carrier or a covalent compound thereof; R' is a H atom, a substituted or unsubstituted aryl group, an alkyl, alkenyl or hydroxyalkyl group having 1 to 10 carbon atoms, a complex lipid, a simple lipid, an oligosaccharide which does not contain any lactosamine residue, a ceramide residue, a pharmaceutically active ingredient, a solid carrier or a covalent compound thereof.

Myelorollin-containing structures, especially that exists in human body or ganglioside, as well as antibodies that block myelorollin caused rolling and adhesion on E-selectin expressing cells, are useful reagents for inhibitive inflammatory responses, particularly chronic conditions such as rheumatoid arthritis, kidney disease, and hepatitis.

A mixture of myelorollin rather than a single molecular species causes stronger rolling and adhesion of E-selectin expressing cells. Therefore, mixtures of myelorollin containing such components as A, B, C, D, X and Y are particularly useful reagents to inhibit inflammatory responses.

Figure 2:
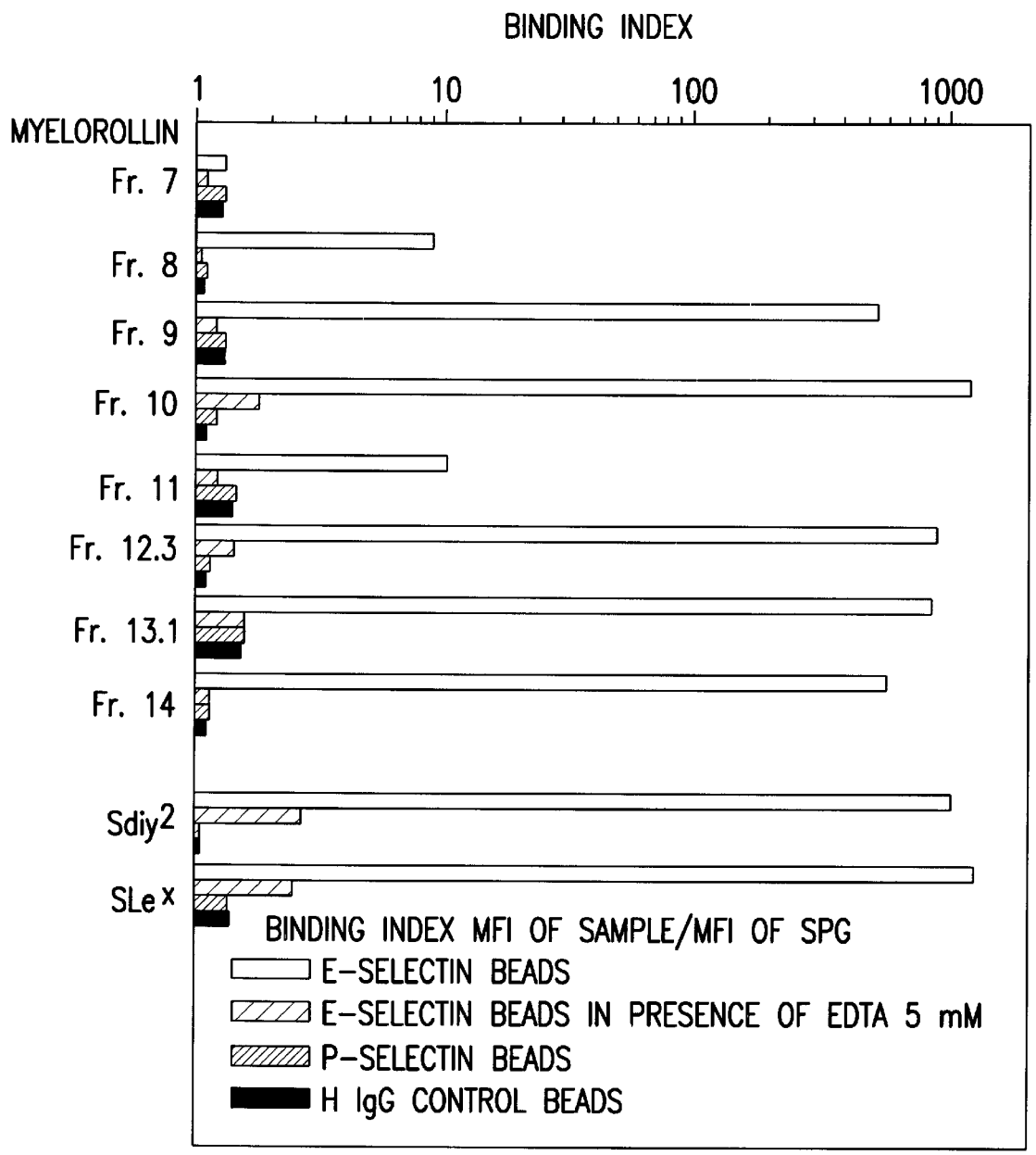

FIG. 2 shows adhesion under static conditions of E-selectin-expressing CHO cells to various gangliosides coated and affixed on polystyrene beads. The various coated beads are: E-selectin beads (□); E-selectin beads in presence of 5 mM EDTA (▨); P-selectin beads (▨); H IgG control beads (■).

FIGS. 2A–2E show rolling and adhesion of E-selectin-expressing CHO cells to polystyrene beads coated with various gangliosides under dynamic flow conditions. Various poly-LacNac gangliosides were quantitatively adsorbed on beads affixed to glass microscope slides as described in the Materials & Methods section in the EXAMPLE. These polystyrene beads affixed on galss plates are resistant to dynamic flow. GSL coated on beads are therefore very stable in dynamic flow. Slides were blocked by placing 2% BSA in PBS at room temp for 1 hr, and assembled in a parallel-plate laminar-flow chamber. E-selectin-expressing CHO cells were freshly harvested and suspended in RPMI medium ($1 \times 10^5$ cells/mL). The cell suspensions were placed in an infusion pump connected to the flow chamber, and infused into the assembly at various laminar flow rates. Cell movements were observed under phase-contrast microscope and recorded by videocassette recorder. Numbers of rolling cells (○) and adherent (nonrolling) cells (●), in at least 10 microscope fields, at four different shear stresses (dynes/$cm^2$; see abscissa), were plotted.

Figure 2A:
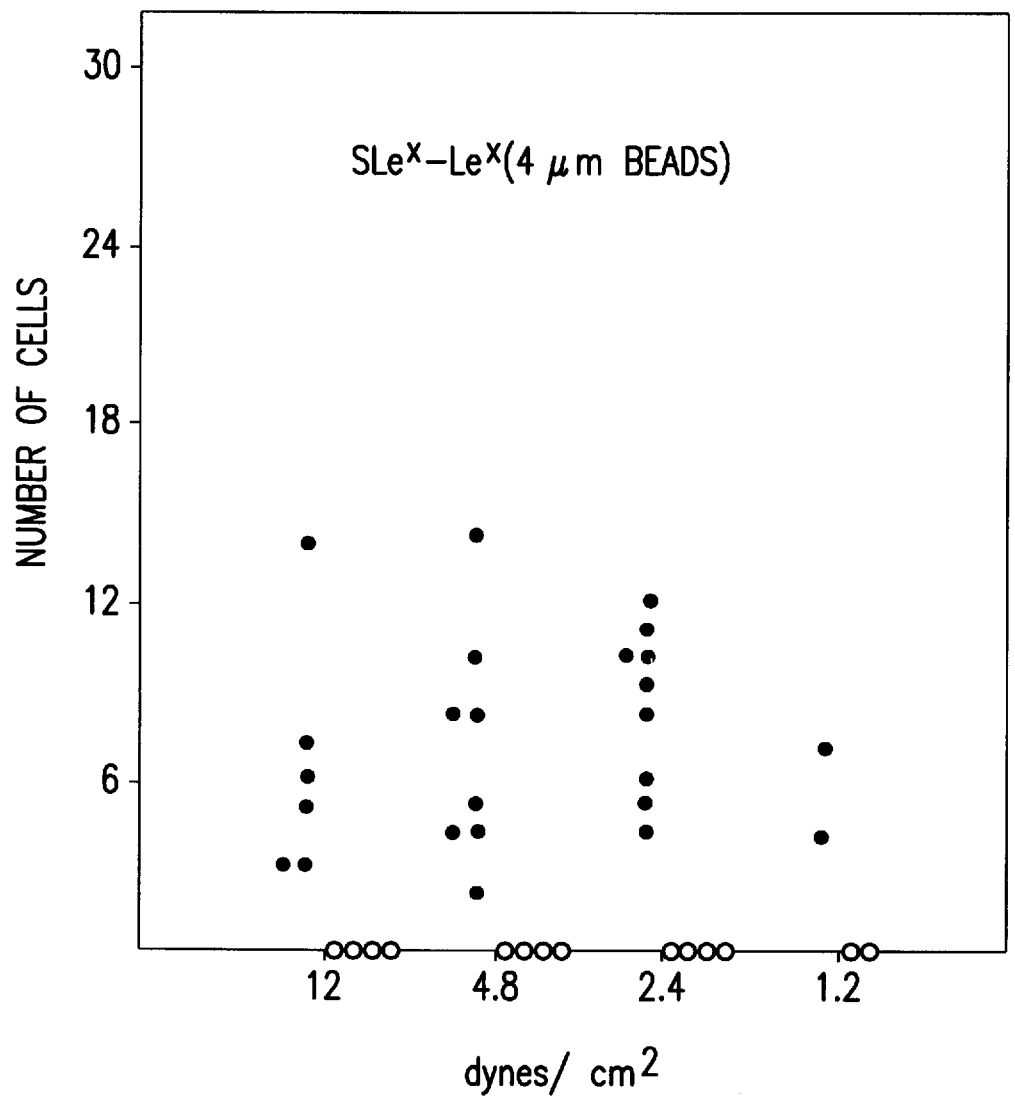

FIG. 2A Rolling/adhesion of cells on $SLe^x-Le^x$ (Str. 1 in FIG. 8) adsorbed on 4 μm beads. There were adherent, but not rolling (i.e. rolling number=0), cells in every field at all shear stresses.

Figure 2B:
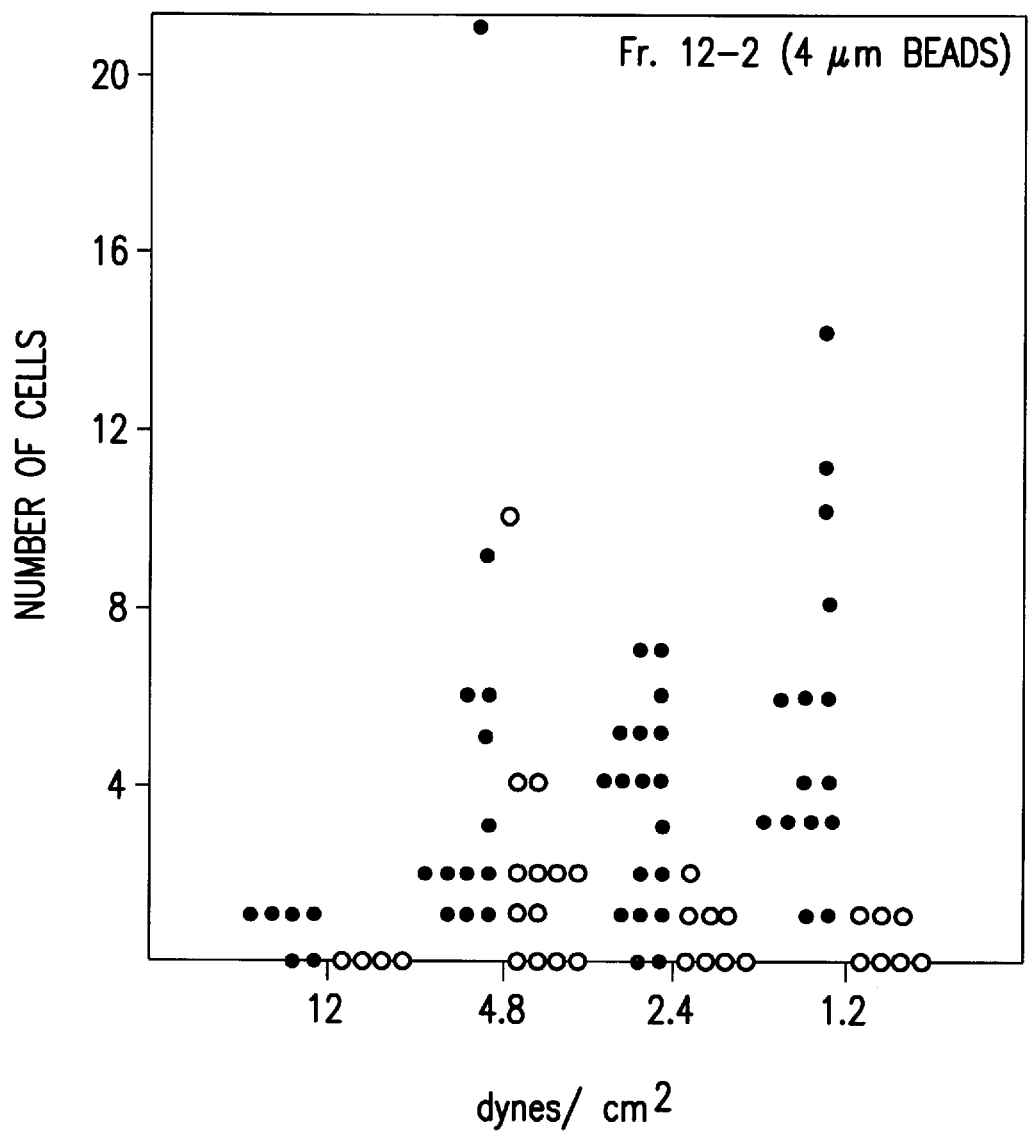

FIG. 2B Fr. 12-2 (Str. 9 in FIG. 8) absorbed on 4 μm beads. Rolling was highest at 4.8 dynes/$cm^2$. Both rolling and adhesion were lower than for Fr. 13-1 and 14 (FIG. 2C and FIG. 2E), but comparable to $SLe^x-Le^x$.

Figure 2C:
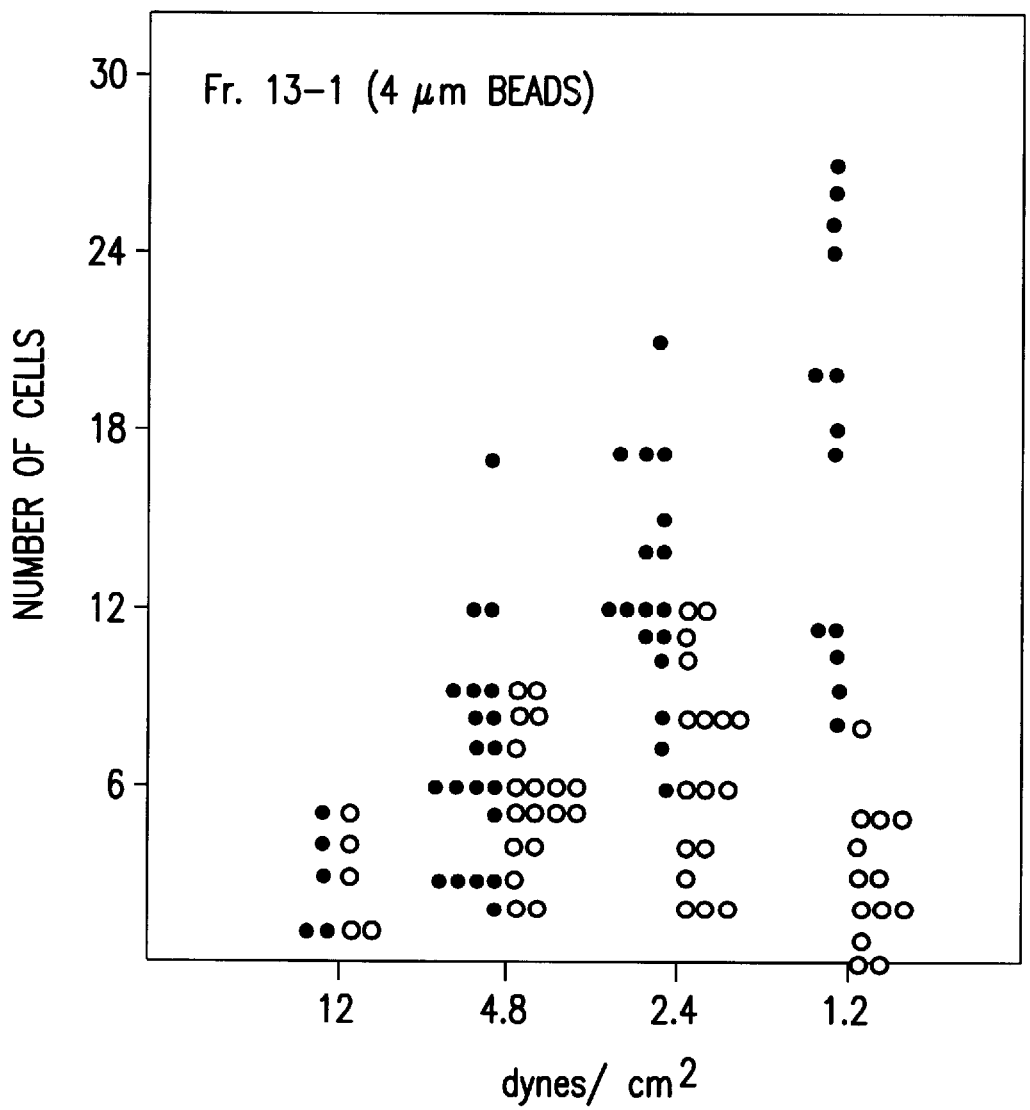

FIG. 2C Fr. 13-1 (Str. 2 in FIG. 8) absorbed on 4 μm beads. Rolling was more frequent at 4.8 and 2.4 than at 1.2 dynes/$cm^2$.

Figure 2D:
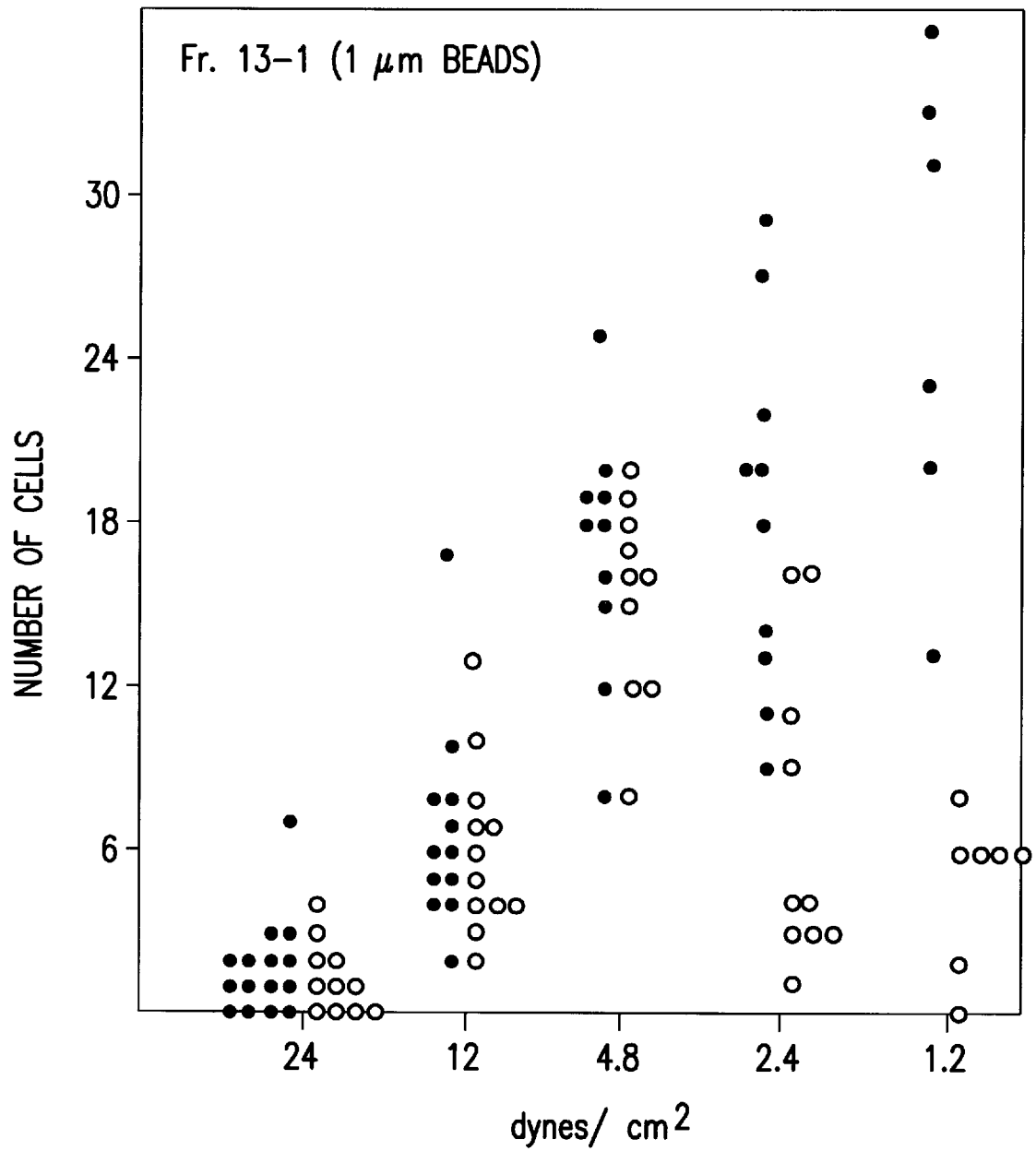

FIG. 2D Fr. 13-1 absorbed on 1 μm beads. Rolling was highest at 4.8. Adhesion was higher and rolling was lower at 1.2 dynes/$cm^2$.

Figure 2E:
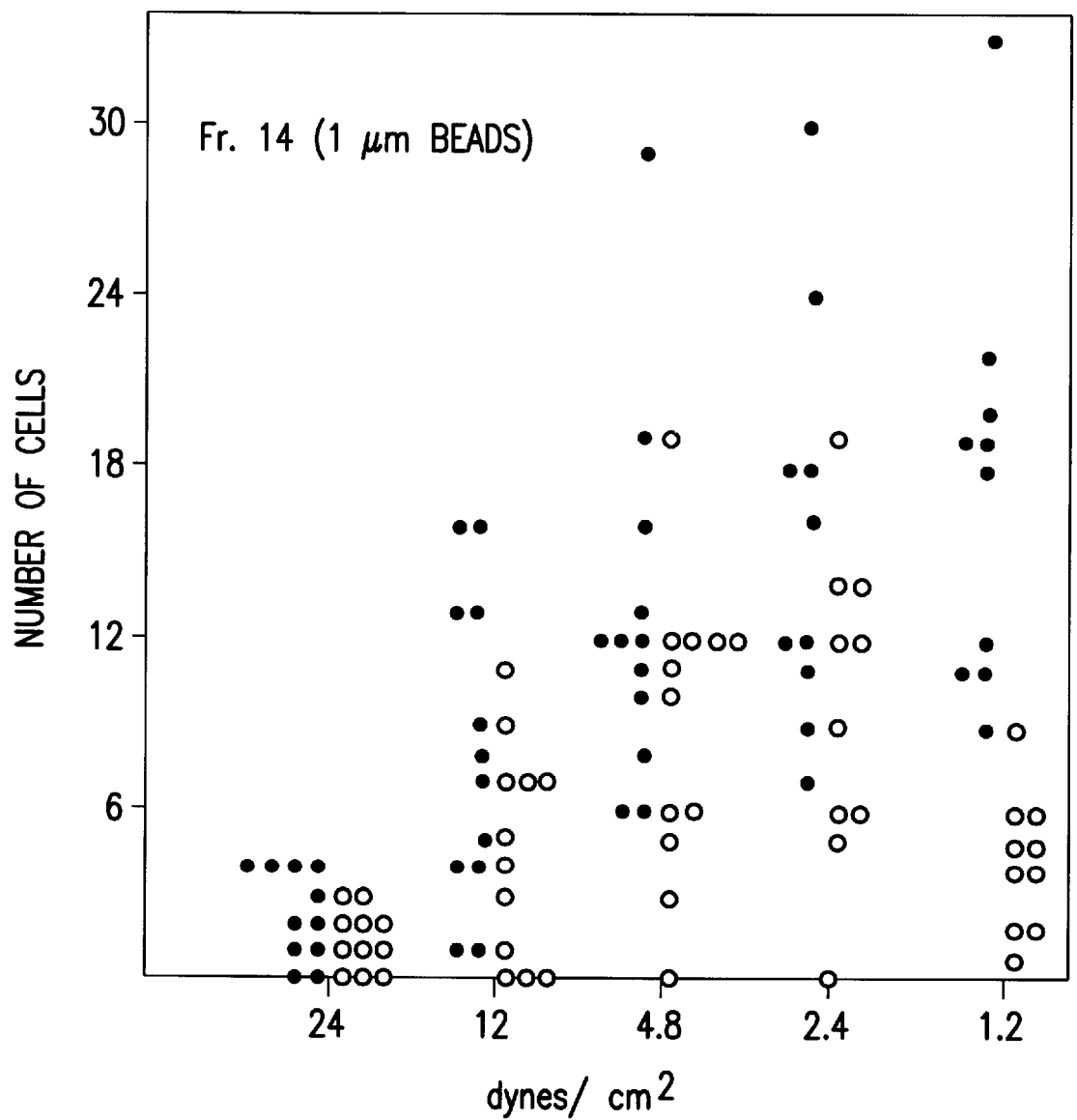

FIG. 2E Fr. 14 absorbed on 1 μm beads. Rolling/adhesion were highest at 2.4 and 4.8 dynes/$cm^2$. Rolling was lower at 1.2 dynes/$cm^2$.

Figure 3:
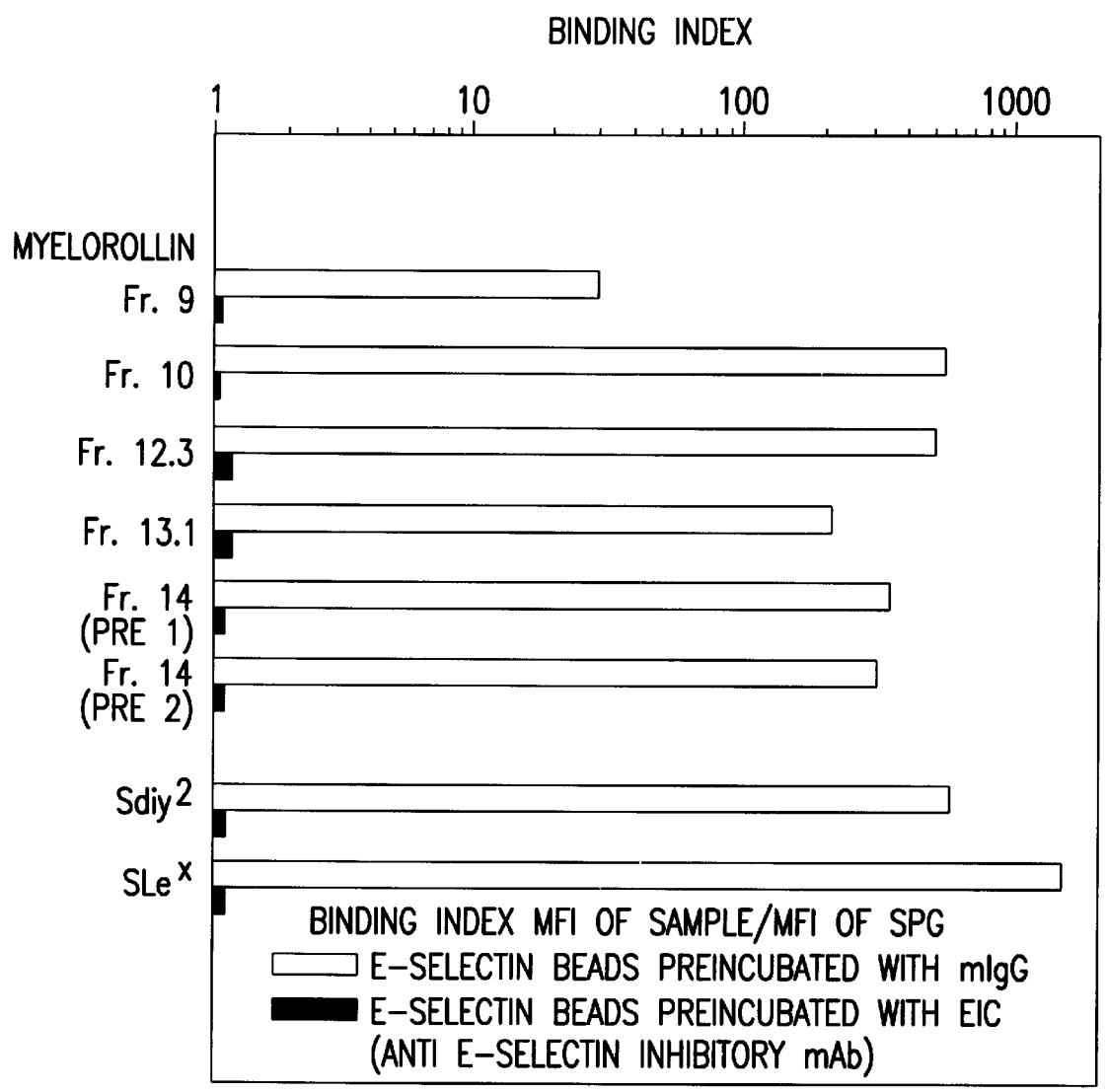

FIG. 3 shows the inhibitory effect of anti-E-selectin antibody on E-selectin binding to various myelorollin fractions. The beads are: E-selectin beads preincubated with mIgG (□); E-selectin beads preincubated with EIC (■), EIC is an anti E-selectin inhibitory mAb.

Figure 3A:
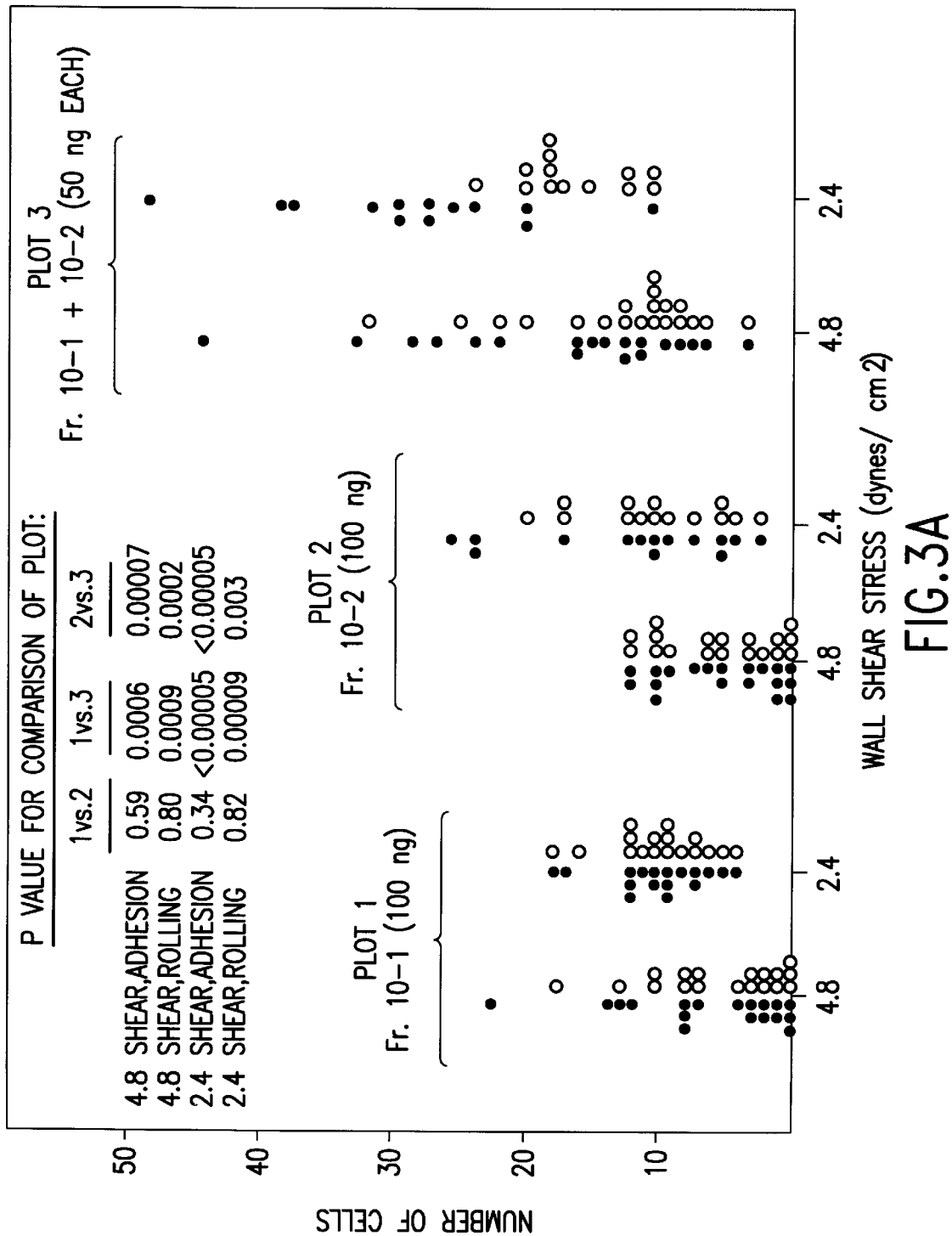
Figure 3B:
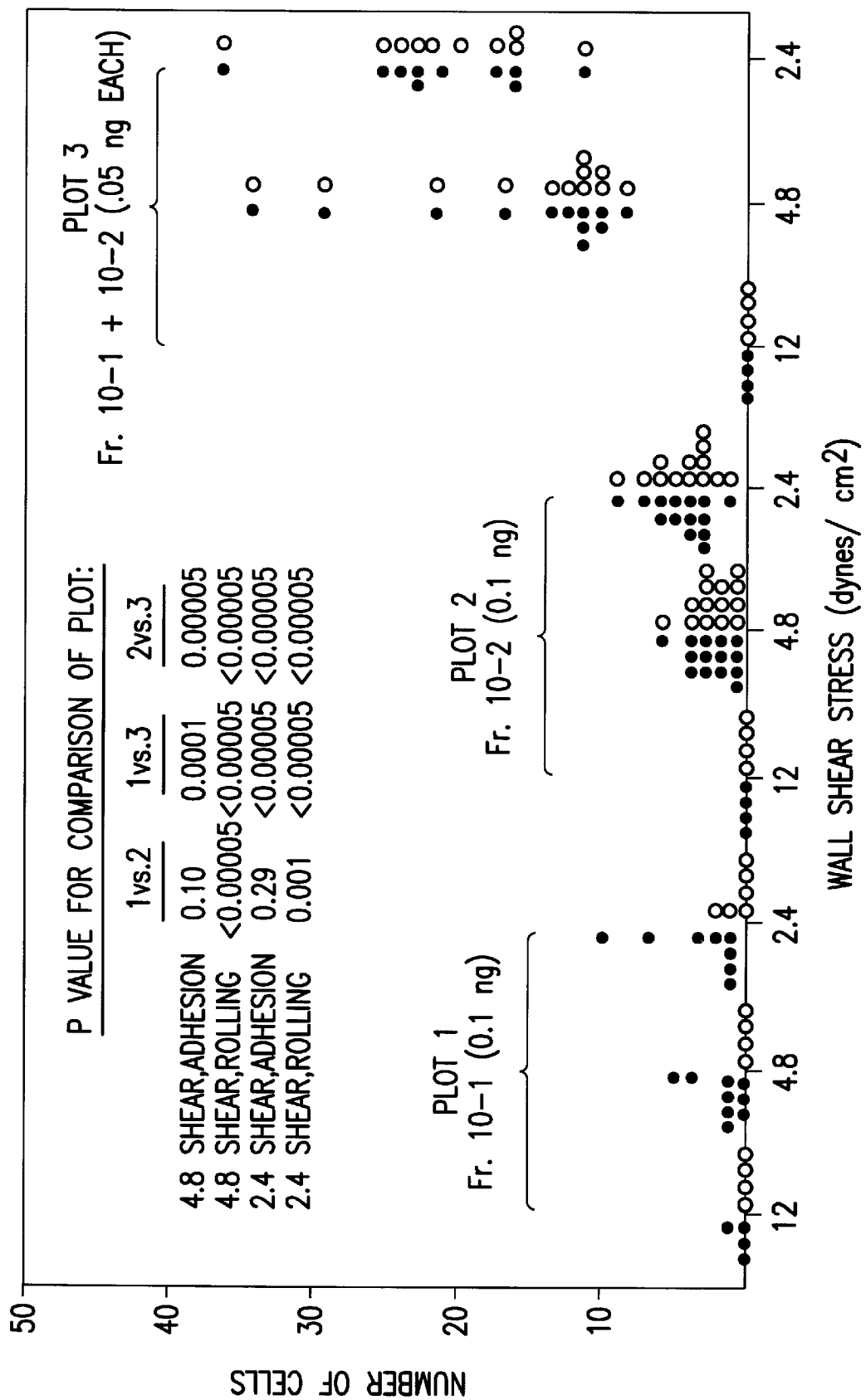

FIGS. 3A and 3B show rolling and adhesion of E-selectin-expressing CHO cells on polystyrene beads coated with under dynamic flow conditions. Fraction 10-1, Fraction 10-2 and mixture FIG. 3A Plot 1. Adhesion (●) and rolling (○) on 100 ng of Fr. 10-1 (Str. 7 in FIG. 8). Plot 2. 100 ng of Fr. 10-2 (Str. 8 in FIG. 8). Plot 3. Mixture of 50 ng each of Fr. 10-1 and 10-2. Gangliosides were adsorbed on 1 μm beads. Values for shear stresses of 12 and 4.8 dynes/$cm^2$ are shown. Statistical significance of differences between various subsets of data were evaluated by unpaired Student's t-test, and P values are summarized in the insert table.

FIG. 3B Plot 1. Rolling/adhesion on 0.1 ng of Fr. 10-1. Plot 2. 0.1 ng of Fr. 10-2. Plot 3. Mixture of 0.05 ng each of Fr. 10-1 and 10-2. Gangliosides were adsorbed on 1 μm beads. Three different shear stress values are shown. Rolling/adhesion occurred even at this low ganglioside concentration. Number of rolling and adhered cells was greatest for the mixture of gangliosides (plot 3). P values are summarized in inset table as in FIG. 3A.

Figure 4:
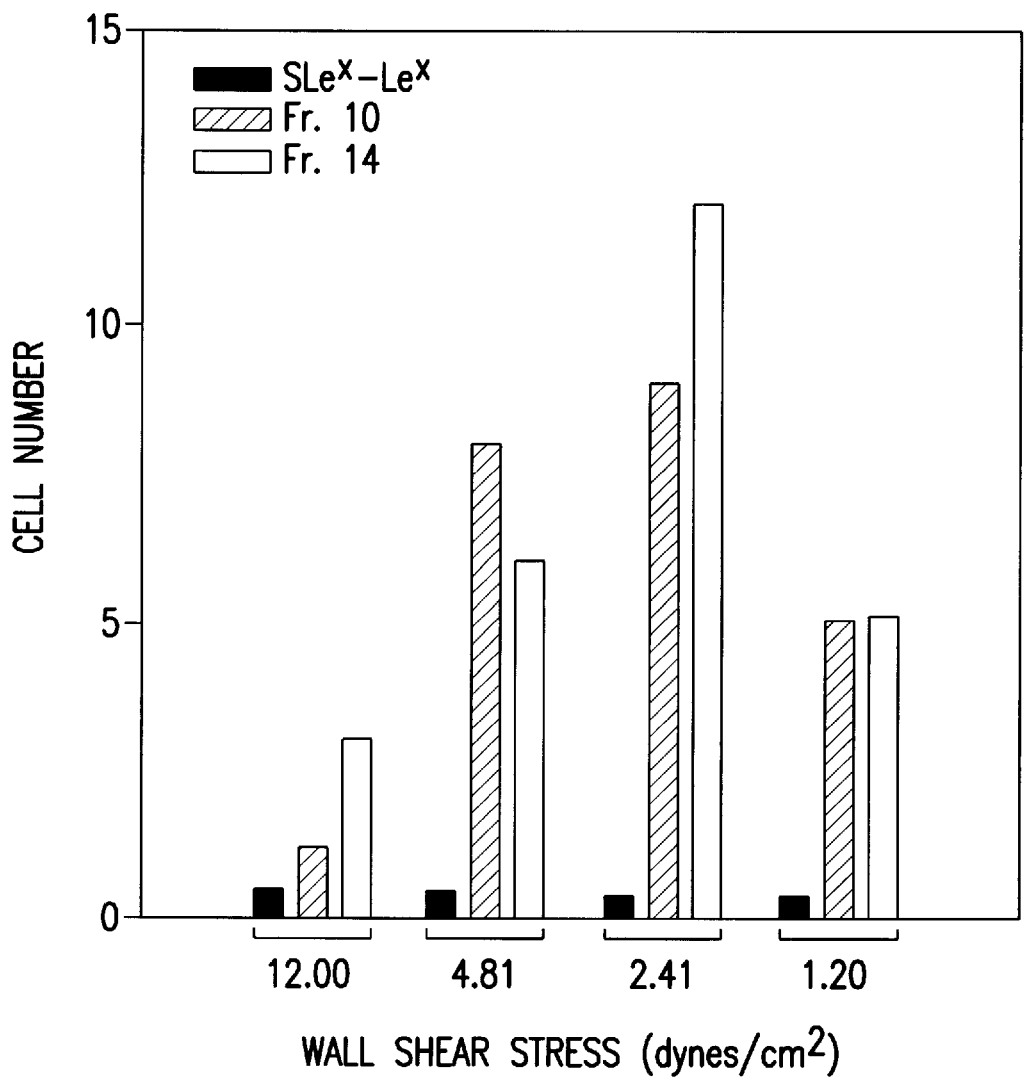

FIG. 4 shows rolling of E-selectin-expressing CHO cells under dynamic flow conditions (part I). The figure shows the number of rolling cell (E-selectin expressing cells) caused by various ganglioside coated materials (means of ten different fields). The various coated beads are: Fr. 14 (□); Fr. 10 (▨); $SLe^x-Le^x$ (■).

Figure 4A:
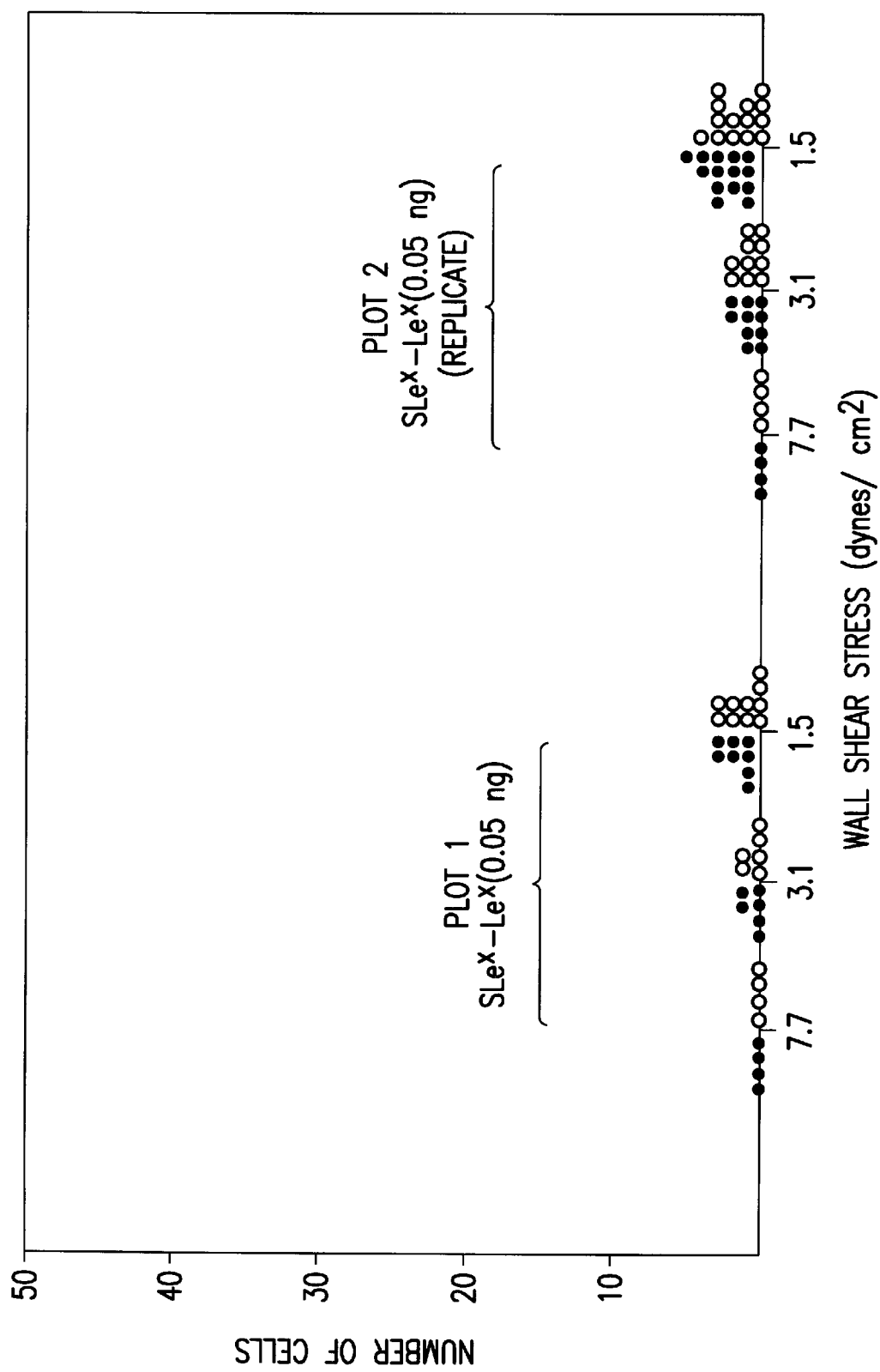
Figure 4B:
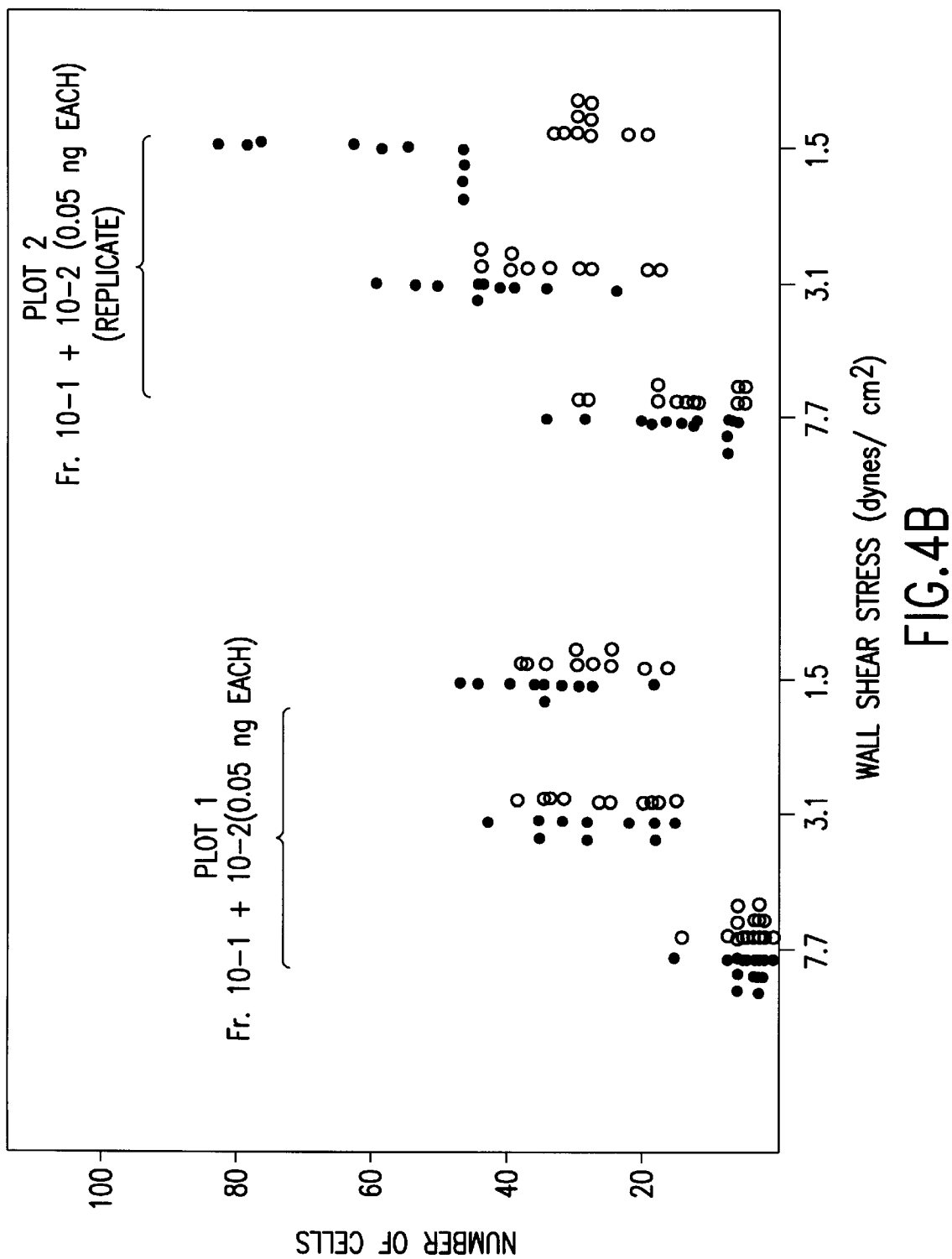

FIGS. 4A and 4B show rolling and adhesion of E-selectin-expressing CHO cells under dynamic flow conditions, with a particular focus on the difference of rolling/adhesion on $SLe^x-Le^x$ versus Fraction 10-1 and Fraction 10-2 at very low quantities.

FIG. 4A Plot 1. Adhesion (●) and rolling (○) of cells on 0.05 ng of $SLe^x-Le^x$ at shear stresses of 7.7, 3.1, and 1.5 dynes/$cm^2$. Plot 2. Replicate experiment, same conditions as plot 1.

FIG. 4B Plot 1. Mixture of 0.005 ng each of Fr. 10-1 and 10-2 (note: this gives the same molarity as 0.05 ng of $SLe^x-Le^x$, because molecular weight of $SLe^x-Le^x$ is twice that of Fr. 10-1 or 10-2). Same shear stresses as in FIG. 4A. Plot 2. Replicate experiment, same conditions as plot 1.

Figure 5:
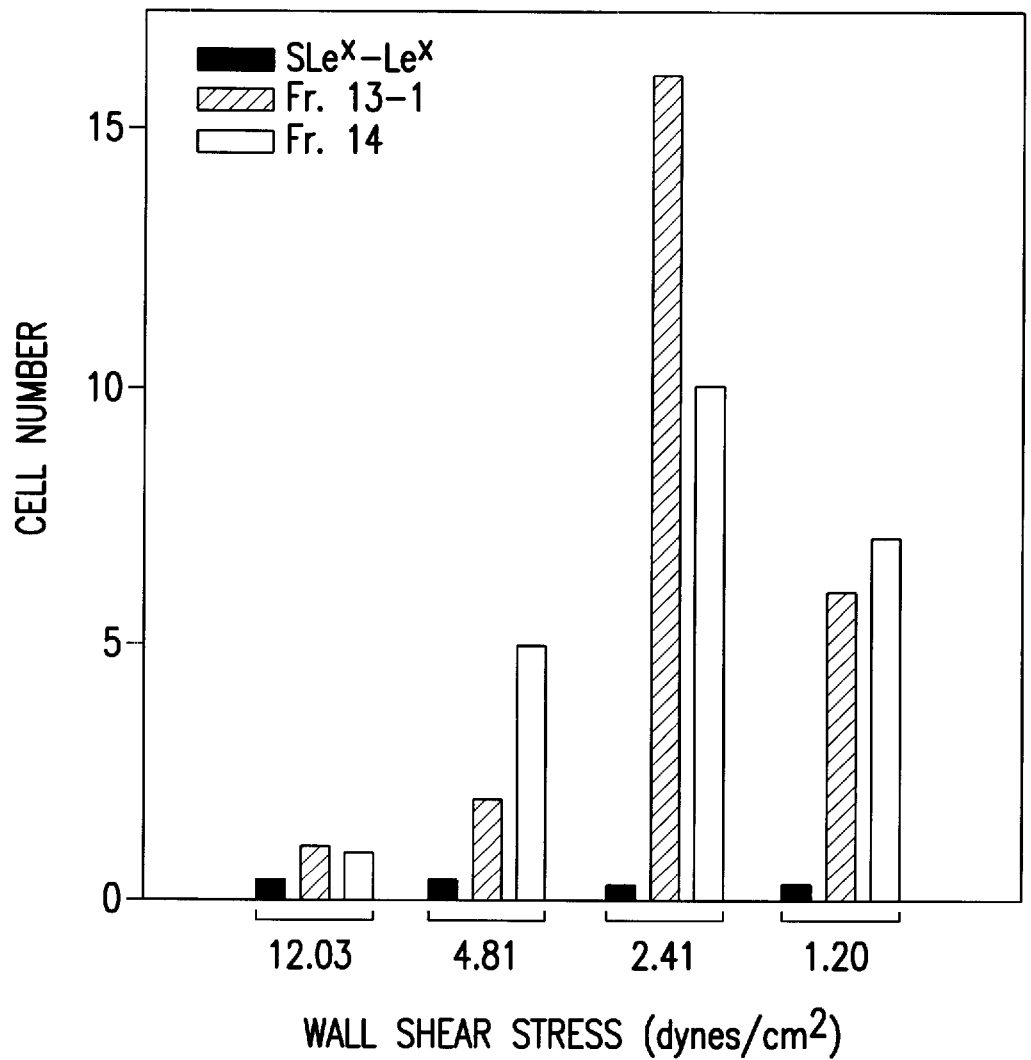

FIG. 5 shows rolling of E-selectin-expressing CHO cells under dynamic flow conditions using fraction 13-1 and repeating fraction 14 (part II). The figure shows the number of rolling cell (E-selectin expressing cells) caused by various gangliosides coated on plastic surfaces (means of ten different fields). The various coated surfaces are: Fr. 14 (□); Fr. 13-1 (▨); Fr. 10 ) (▨) $SLe^x-Le^x$ (■).

Figure 5A:
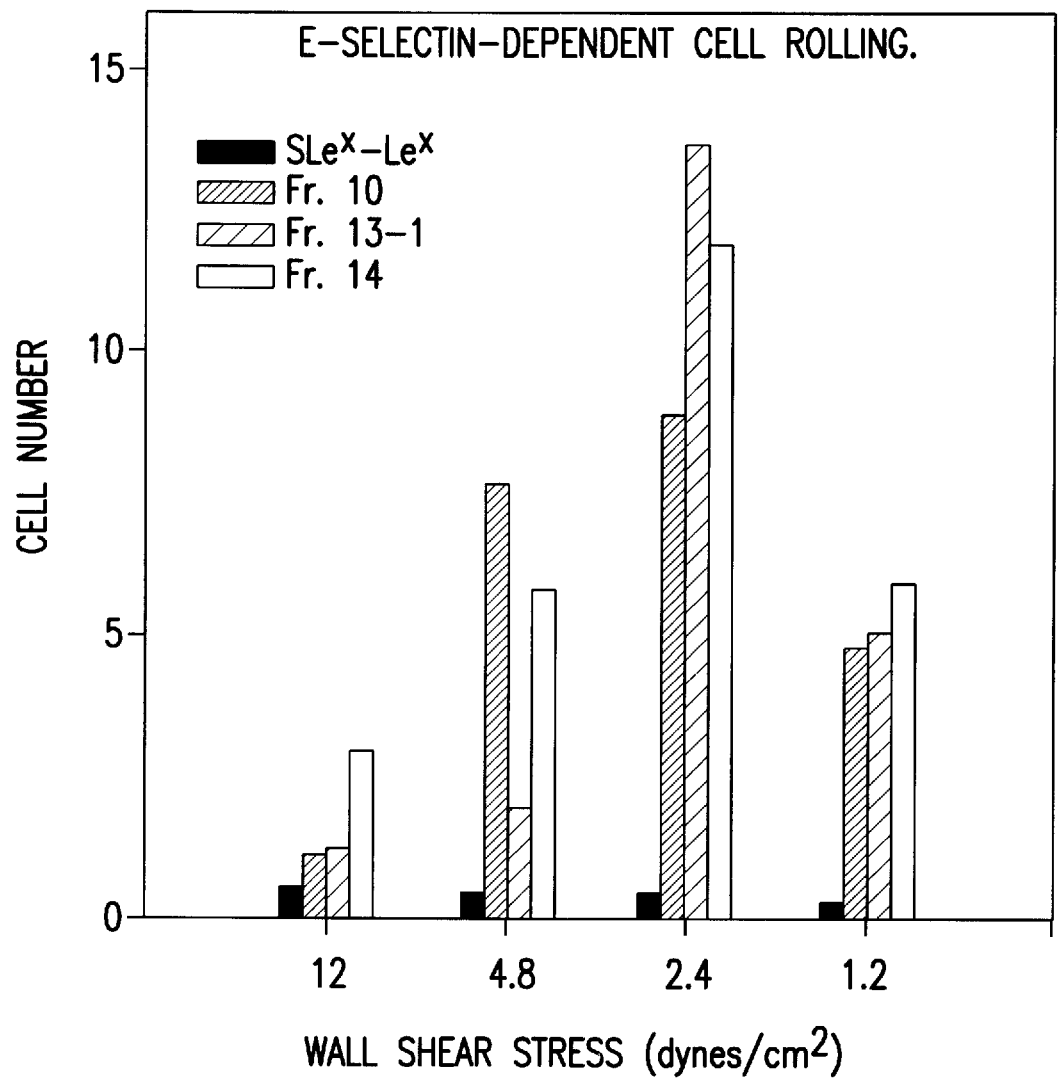

FIG. 5A shows rolling of E-selectin-expressing CHO cells under dynamic flow conditions. Mean value of rolling cell number on various gangliosides (100 ng each) coated on polystyrene beads (diameter 4 μm) affixed on glass plates at different shear stresses in dynamic flow system. Ordinate: number of rolling cells (note including adherent cells on $SLe^x-Le^x$ and various myelorollins. Abscissa: wall shear stress (dynes/$cm^2$). In each shear stress group, the columns from left to right are: $SLe^x-Le^x$; mixture of Fr. 10-1 and 10-2; Fr. 13-1 and Fr. 14. Structures of these gangliosides are shown in FIG. 8. The data shown combine those shown in FIGS. 4 and 5.

FIGS. 6A–6D show adhesion and rolling followed by adhesion of E-selectin-expressing CHO cells to polystyrene beads coated with various gangliosides under dynamic flow conditions. The curved arrow represents dynamic cell adhesion without cell rolling. The spiral arrow represent dynamic cell adhesion with cell rolling. The abscissa represents the number of adherent cells (means of 10 fields).

Figure 7A:
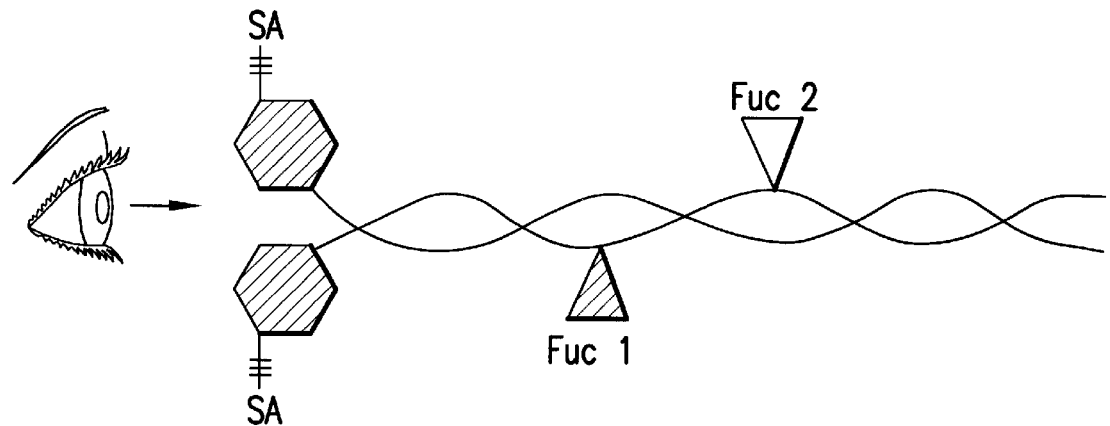
Figure 7B:
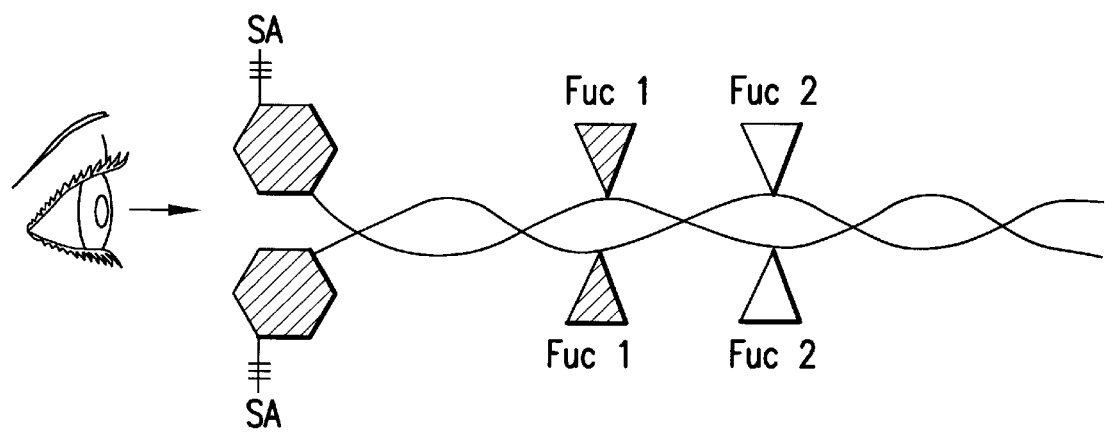
Figure 7C:
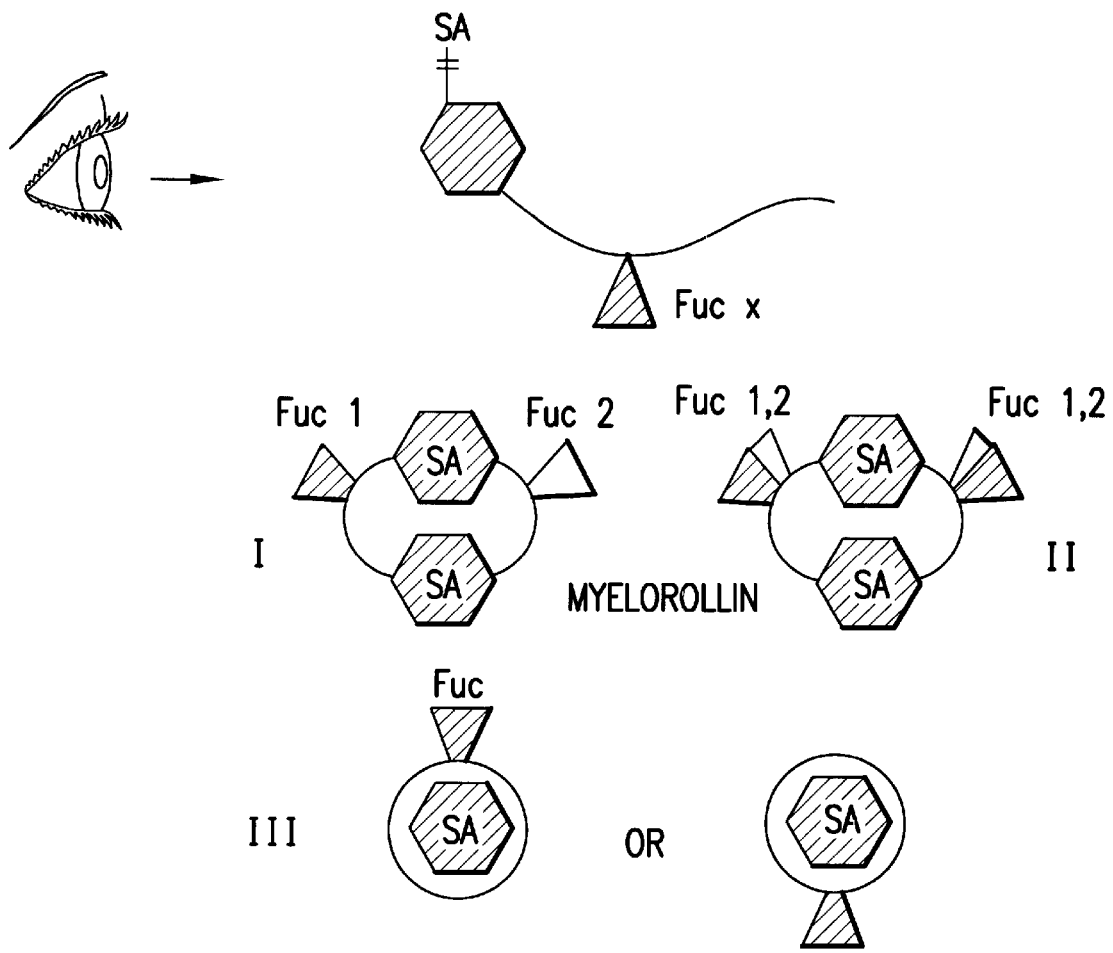

FIGS. 7A–7C show the possible spatial arrangements of sialosyl residues (SA) and fucosyl residues at the internal GlcNAc of different positions (Fuc1 and Fuc2) along the polylactosamine chain.

Figure 8B:
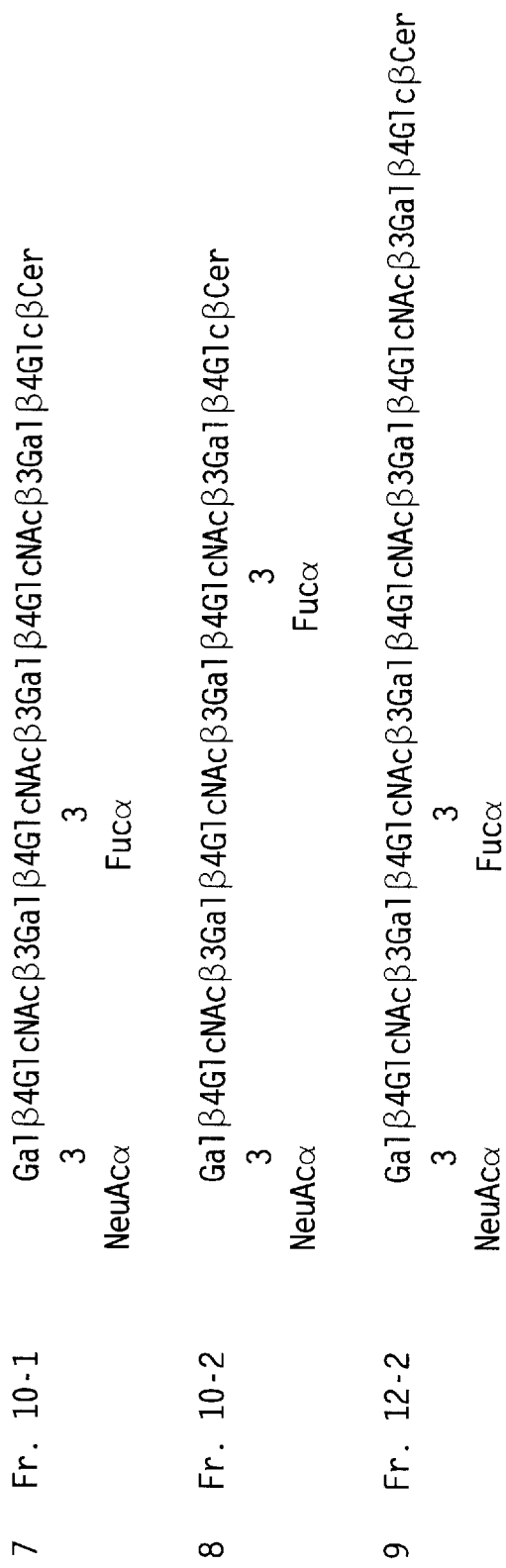

FIGS. 8 and 8B show the structures of myeloglycan type and related gangliosides.

DETAILED DESCRIPTION OF THE PREFERRED EMBODIMENT

We detected the presence, in neutrophils and human promyelogenous leukemia HL60 cells, of polylactosamine gangliosides with terminal α2→3 sialylation and α1→3 fucosylation at various internal (but not the penultimate)

GlcNAc residues, a group of compounds having the saccharide sequence of such gangliosides is collectively termed "myelorollin". In contrast, SLe$^x$-Le$^x$ determinant without internal α1→3 fucosylation of polylactosamine chain were absent in these cells. In this study, a series of myelorollin (A, B, C, D, X, Y below) without SLe$^x$ determinant, affixed to latex beads, were found to interact strongly with E-selectin-human-Ig Fc portion fusion protein coated on fluorescent latex beads. The interaction was quantifiable by flow cytometry. The myelorollin of the invention included the following compounds:

expressed by human neutrophils or other cells similar thereto, to a solid phase, adding thereto under a shear stress attainable in human body E-selectin expressing cells, such as E-selectin expressing CHO cells, observing, for each time unit, rolling, adhesion and streaming of said cells on said solid phase and consequently selecting materials causing rolling. A shear stress attainable in human body means preferably a shear stress to be caused by human blood flow, in the preferable range of 0.8–12 dyne/cm$^2$.

Alternatively, myelorollins A, B, C, D and X, Y were adhered on polystyrene beads affixed to a glass slide which

```
A    Galβ4GlcNAcβ3Galβ4GlcNAcβ3Galβ4GlcNAcβ3Galβ4GlcNAcβ ─────▶ R
                3                           3
          NeuAcα                      Fucα

B    Galβ4GlcNAcβ3Galβ4GlcNAcβ3Galβ4GlcNAcβ3Galβ4GlcNAcβ ─────▶ R
                3                                       3
          NeuAcα                                  Fucα

C    Galβ4GlcNAcβ3Galβ4GlcNAcβ3Galβ4GlcNAcβ3Galβ4GlcNAcβ ─────▶ R
                3              3                        3
          NeuAcα           Fucα                   Fucα

D    Galβ4GlcNAcβ3Galβ4GlcNAcβ3Galβ4GlcNAcβ3Galβ4GlcNAcβ ─────▶ R
                3              3                        3
          NeuAcα           Fucα                   Fucα

X    Galβ4GlcNAcβ3Galβ4GlcNAcβ3Galβ4GlcNAcβ ─────▶ R
                3                           3
          NeuAcα2                     Fucα

Y    Galβ4GlcNAcβ3Galβ4GlcNAcβ3Galβ4GlcNAcβ ─────▶ R'
                3                           3
          NeuAcα2                     Fucα
``` wherein → indicates covalent bond; R is a H atom, a substituted or unsubstituted aryl group, an alkyl, alkenyl or hydroxyalkyl group having 1 to 10 carbon atoms, a complex lipid, a simple lipid, an oligosaccharide, a ceramide residue, a pharmaceutically active ingredient, a solid carrier or a covalent compound thereof; R' is a H atom, a substituted or unsubstituted aryl group, an alkyl, alkenyl or hydroxyalkyl group having 1 to 10 carbon atoms, a complex lipid, a simple lipid, an oligosaccharide which does not contain any lactosamine residue, a ceramide residue, a pharmaceutically active ingredient, a solid carrier or a covalent compound thereof. Myelorollins of the invention also include the following compounds:

was then placed in a parallel laminar-flow chamber assembly, allowing determination of rolling and adhesion of E-selectin-expressing cells under dynamic flow conditions with defined shear stress. The apparatus was similar to that described by Lawrence et al. (Blood 75:227, 1990). Rolling and adhesion of E-selectin-expressing cells was clearly observed on affixed myelorollin A, B, C, D, X, Y or a mixture thereof, but not affixed SLe$^x$-Le$^x$. The rolling is more remarkable with a mixture rather than a purified single component under a dynamic flow condition. In contrast, under static conditions, a higher number of E-selectin-expressing cells adhered to SLe$^x$-Le$^x$ affixed to beads as compared to myelorollin-coated plates. These results sup-

```
       Galβ4GlcNAcβ3Galβ4GlcNAcβ3Galβ4GlcNAcβ3Galβ4GlcNAcβ3Galβ4GlcNAcβ→R       I
                 3                                       3
           NeuAcα2                                 Fucα

Galβ4GlcNAcβ3Galβ4GlcNAcβ3Galβ4GlcNAcβ3Galβ4GlcNAcβ3Galβ4GlcNAcβ→R       J
                 3                    3                  3
           NeuAcα2              Fucα               Fucα

Galβ4GlcNAcβ3Galβ4GlcNAcβ3Galβ4GlcNAcβ3Galβ4GlcNAcβ3Galβ4GlcNAcβ→R       K
                 3              3                        3
           NeuAcα2         Fucα                    Fucα
``` wherein R comprises a H atom, a substituted or unsubstituted aryl group, an alkyl, alkenyl or hydroxyalkyl group having 1 to 10 carbon atoms, a complex lipid, a simple lipid, an oligosaccharide, a ceramide residue, a pharmaceutically active ingredient, a solid carrier or a covalent compound thereof.

Myelorollin of the present invention should be selected by an appropriate procedure. It includes the procedure comprising affixing probe material, such as gangliosides port the concept that E-selectin-dependent rolling and adhesion of leukocytes and leukemic cells (e.g., HL60) in general is mediated by myelorollin (A, B, C, D and X, Y) rather than by SLe$^x$-containing structures.

In the above formulas, R and R' is, respectively, H, a substituted or unsubstituted aryl group, an alkyl, alkenyl or hydroxyalkyl group having 1 to 10 carbon atoms, a complex lipid, a simple lipid, an oligosaccharide (oligosaccharide containing no lactosamine residue for R'), a ceramide residue, a pharmaceutically active ingredient, a solid carrier or covalent compound thereof. The groups R and R' can be covalently bound to GlcNAc at the reducing terminus of the formulas via an appropriate spacer, such as diamine, aminoalcohol, amino acid, peptide.

As substituent for the aryl group, illustrated are alkyl, alkenyl and alkynyl groups having 1 to 6 carbon atoms, halogen atoms, hydroxyl group, nitro group and carboxyl group.

Among complex lipids and simple lipids, ceramide is the most preferred and naturally occurring lipid carrier of myelorollins. Glycerolipids include diacylglycerol and the like neutral lipids. Chain length and unsaturation degree of the acyl group in those lipids are not particularly limited.

The oligosaccharide includes oligosaccharides consisted of 1 to 10 monosaccharides, specifically Gal, Gal→Glc, $$(Gal \rightarrow GlcNAc)_n,$$
$$|$$
$$(Fuc\alpha)_m$$

and the like, wherein n is an integer of 1 to 5 and m is an integer of 0 to 5. The pharmaceutically active ingredient includes non-steroid anti-inflammatory drugs, for example, salicylic acid derivatives such as aspirin; aryl acetic acid derivatives such as indomethacin; propionic acid derivatives such as ibuprofen; pyrazolone derivatives such as phenylbutazone; oxicam derivatives such as piroxicam; epirizol and the like. The covalent compound includes covalently combined oligosaccharide and ceramide, specifically Gal$\beta$1→4Glc$\beta$1→Cer and the like.

Our results and conclusions are summarized as follows:
1. SLe$^x$-containing structures do not cause rolling, are virtually absent in neutrophils and HL60 cells, and have no physiological role in rolling, adhesion and extravasation of neutrophils.
2. It is not SLe$^x$-containing structure, but rather a group of non-SLe$^x$-containing structures collectively called "myelorollin" (i.e., unbranched polylactosamine with terminal $\alpha$2→3 sialylation and internal fucosylation [at various GlcNAc residues except for the penultimate GlcNAc alone]) which are responsible for causing rolling, adhesion and extravasation of neutrophils.
3. Various types of myelorollin in a mixture synergistically cause E-selectin-dependent rolling and adhesion as compared with a singular molecule of myelorollin.
4. Mylerollin is the major glycan and ganglioside of HL60 cells and human leukocytes.
5. Myelorollin-containing structures and their mimetics are considered useful reagents for inhibiting inflammatory responses, particularly chronic conditions such as rheumatoid arthritis, kidney disease, hepatitis, etc. Mimetics of structures A, B, C, D and X, Y are constructed based on spatial configuration, i.e., location of sialic acid and different sites of fucosyl residue. The orientation of fucosyl residue and its relationship with sialic acid position is of primary importance (see FIG. 7A–7C).
6. Myelorollin can by synthesized in large quantities by polymerization of N-acetyllactosamine followed by $\alpha$2→3 sialylation and $\alpha$1→3 fucosylation by sialosyltransferase and fucosyltransferase, respectively. Myelorollin can also be prepared from a large scale culture of HL60 cells or U937 cells as described below.

Myelorollin can be obtained by reacting (a) unbranched polylactosamine having $\alpha$2→3 sialosyl residue at the non-reducing terminus and $\alpha$1→3 fucosyl residues at the internal GlcNAc but not solely at the penultimate GlcNAc directly or via spacer with (b) a substituted or unsubstituted aryl halide, an alkyl, alkenyl or hydroxyalkyl halide having 1 to 10 carbon atoms, a complex lipid, a simple lipid, an oligosaccharide, a ceramide, a pharmaceutically active ingredient, a solid carrier or a covalent compound thereof using known method, such as glycosylation of the saccharide residue at the reducing terminus.

7. Blocking of myelorollin function can be achieved by a minimal essential structure involving in myelorollin that causes rolling and adhesion dependent on E-selectin. Antibodies highly specific to saccharide sequence of myelorollin can be readily prepared, selected, and used for anti-inflammatory drug preparation.

MATERIALS AND METHODS

GSLs and monosialogangliosides:

Monosialoganglioside fractions used for adhesion assay are shown in Table 1, and adhesion assay is performed as described for FIGS. 1, 1A–B, 2, 2A–E, 3, 3A–B. Structures were verified by endo-$\beta$-galactosidase digestion (Fukada, et al. J. Biol. Chem 254:5458–5465, (1979)), $^1$H-NMR, $^+$ion FABMS, and ES-MS with CID of permethylated compounds (Stroud et al., Biochem. Biophys. Res. Comm. 209:777–787 (1995); Stroud, M. R. Biochemistry 35:758–778 (1996)).

Cells and binding assay:

CHO cells transfected with E-selectin cDNA were established as described previously (Handa, et al., 1995, Int. J. Oncol. 6:773–781). E-selectin-expressing transfectants were isolated by cytofluorometry using anti-E-selectin mAb E1A. Inhibition of E-selectin-dependent cell adhesion was performed using anti-E-selectin mAb E1C at 10 $\mu$g/mL concentration. These mAbs were established through immunization of BALB/c mice with NS1 cells expressing E- or P-selectin.

Demonstration of Direct Binding of E- or P-selectin to myelorollin gangliosides by fluorometric analysis:

$5 \times 10^6$ polystyrene latex beads (diameter 4.2±3.7% $\mu$m) (IDC Spheres™; IDC, Portland, Oreg.) were washed with ethanol by centrifugation. 1 $\mu$g of GSL in 50 $\mu$L of ethanol was added to the washed beads and the mixture was evaporated under nitrogen stream. The beads were resuspended in 1% BSA in PBS(+) and washed twice by centrifugation. Washed beads were blocked with 3% BSA in PBS(+) at room temperature for 2 hr. After centrifugation, beads were resuspended in 1% BSA in PBS(+) with 0.1% azide and stored at 4° C. Yellow-green fluorescent sulfated latex beads (diameter 1 $\mu$m) (Molecular Probes, Inc., Portland, Oreg.) were coated with goat anti-human IgG (Fc-fragment specific) antibody (Jackson Immunoresearch Lab, West Grove, Pa.) according to manufacturer's protocol. After washing 3x with PBS, beads were blocked with 3% BSA in PBS at 4° C. for 2 hr. Blocked beads (about $5 \times 10^8$) were mixed with 1.5 mL of E- or P-selectin-Ig fusion protein containing culture supernatant (about 1 $\mu$g/mL fusion protein) from CHO transfectants (Handa et al., 1995 Int. J. Oncol. 6:773–781) with a blood mixer at 4° C. for 6–18 hr. This mixing procedure was repeated 3 times more using new culture supernatant containing the fusion protein. After washing with PBS, beads were incubated in 1 mL PBS containing 50 $\mu$g human IgG (Jackson Immunoresearch). For preparation of control beads, human IgG was used at 1 $\mu$g/mL, instead of fusion protein. The ganglioside-coated beads were mixed with the fluorescent beads at room temperature for various durations. The resulting suspension was subjected to flow cytometric analysis. Conditions of each assay are detailed below.

E-selectin-dependent cell rolling and adhesion through various GSLs under dynamic flow conditions:

Polystyrene latex beads (4.2±3.7% μm or 1 μm) used as carriers of GSLs as above were suspended in ethanol. 1 μL aliquots of suspension were placed on precleaned and specially treated microscope slides (Labcraft Superfrost® Plus, Curtin Matheson Scientific, Houston, Tex.). Beads were distributed homogeneously on the glass surface within a circular spot with diameter about 1 cm. Slides were heated at 150° C. for 50 sec, which caused the beads to adhere strongly to the surface such that they could not be washed off by water stream at various velocities. Gangliosides dissolved in IHW at the same molar concentration were applied to latex beads affixed on the slides; namely, 1 μL aliquots containing 50–100 or 0.05–0.1 ng ganglioside were placed on the center of a circular spot. The ganglioside thus became affixed to the bead surface.

Slides prepared as above, as they are or after treatment consisted of incubating said slides for at least an hour at room temperature with 3% BSA prewarmed at 37° C. and washing with PBS containing $CA^{2+}/Mg^{2+}$ (i.e., PBS(+)) were placed in a parallel plate laminar flow chamber connected to an infusion pump (model 935, Harvard Apparatus, Cambridge, Mass.). The assembly, originally described by Lawrence et al. (Lawrence et al., 1990, Blood 75:227–237; Lawrence and Springer, 1991, Cell 65:859–873), simulates the flow shear stress present in physiological microvascular environments. A laminar flow with defined rate and wall shear stress is achieved by manipulation of the infusion pump, which is connected to the inlet of the flow chamber. A suspension of E- or P-selectin-expressing CHO cells ($1\times10^5$/mL in FIGS. 2A–2E, $2\times10^5$/cells mL in FIG. 3A, $5\times10^5$/cells mL in FIGS. 3B, 4A and 4B), freshly harvested from culture with EDTA, washed, and resuspended in 1% FCS-RPMI medium, was infused into the assembly at various laminar flow rates. Cell movements were observed under inverted phase-contrast microscope (Diaphot-TMD, Nikon) and recorded by time-lapse videocassette recorder. Cell rolling and adhesion were observed, and numbers of rolling and adherent cells during a 2 min period at shear stresses, from 0.6–12.0 dynes/cm² were counted from at least 10 fields on videotape. Wall shear stress (T) was calculated by the equation of Lawrence et al. (Lawrence et al., 1990 Blood 75:227–237; Lawrence et al., 1987, Blood 70: 1284–1290): $T=3 \mu Q/2ba^2$, where $\mu$=coefficient of viscosity (1.0 cP), Q=volumetric flow rate (cm³/sec), a=half channel height (in this case, $5.7\times10^{-3}$ cm), and b=channel width (1.3 cm).

E-selectin-dependent cell adhesion to ganagliosides affixed on polystyrene beads under static conditions:

Gangliosides coated on polystyrene beads affixed on glass slides as described above and placed in petri dishes were incubated with E-selectin-expressing CHO cells in 1% FCS-RPMI medium. After 30 min, slides were washed 3 times with PBS, and numbers of adherent cells were counted under a microscope.

E-selection-dependent cell adhesion to various GSLs under static conditions on plastic plate Static adhesion assay using 96-well plates: Poly-LacNAc gangliosides with $SLe^x$-$Le^x$ structure and Frs. 9, 10-1, 10-2 and 12-2, dissolved in 50% ethanol, were serially diluted in 96-well plates (the first well contained 200 ng), and plates were dried at 37° C. for 5 hr. Plates with similar serial dilutions of poly-LacNAc gangliosides were prepared for control cell adhesion in the presence of mAb E1C (see above). E-selectin-expressing CHO cells (Handa et al., Int. J. Oncol. 6:773–781 (1995)) were metabolically labeled with [³H] thymidine and incubated for 2 days. Cell suspension ($2\times10^6$ per mL) was prepared by 2 mM EDTA treatment of cultured cells. A 50 μL aliquot of this cell suspension (containing $1\times10^5$ cells; approximately 5000 cpm) was added to each well and incubated for 1 hr. As a control, EDTA-harvested cells were washed with DMEM and incubated with mAb E1C on ice for 30 min, followed by preparation of cell suspension as above, but containing 10 μg mAb E1C per mL. Aliquots were added to each well and incubated as above. Cells were washed 3× with PBS by inversion of the plate on blotting paper. Adherent cell count as measured by ³H activity was determined.

TABLE 1

Gangliosides used for E-selectin binding study.

| Fr.* | Str. | Structure | Cer ion |
|---|---|---|---|
| 7 | 1 | NeuAcα3Galβ4GlcNAcβ3Galβ4GlcNAcβ3GalβGlcβCer | 536 |
| 8 | 2 | Galβ4GlcNAcβ6<br>　　　　　　Galβ4GlcNAcβ3Galβ4GlcNAcβ3GalβGlcβCer<br>　　　　　　3<br>　　　　　　NeuAcα | 658/660 |
| ** | 3 | Galβ4GlcNAcβ3Galβ4GlcNAcβ3GalβGlcβCer<br>3　　　　　　3　　　　　　3<br>NeuAcα　Fucα　　　Fucα | |
| 10-1 | 4 | Galβ4GlcNAcβ3Galβ4GlcNAcβ3Galβ4GlcNAcβ3Galβ4GlcβCer<br>3　　　　　　　　　　　　3<br>NeuAcα　　　　　　　Fucα | 546/548 |
| 10-2 | 5 | Galβ4GlcNAcβ3Galβ4GlcNAcβ3Galβ4GlcNAcβ3Galβ4GlcβCer<br>3　　　　　　　　　　　　3<br>NeuAcα　　　　　　　Fucα | 546/548 |

TABLE 1-continued

Gangliosides used for E-selectin binding study.

| Fr.* | Str. | Structure | Cer ion |
|---|---|---|---|
| 12-2 | 6 | Galβ4GlcNAcβ3Galβ4GlcNAcβ3Galβ4GlcNAcβ3Galβ4GlcNAcβ3Galβ4GlcβCer<br>3                                3<br>NeuAcα                        Fucα            (same as ACFH-18 antigen) | 548 |
| 13-1‡ | 7 | Galβ4GlcNAcβ3Galβ4GlcNAcβ3Galβ4GlcNAcβ3Galβ4GlcNAcβ3Galβ4GlcβCer<br>3                    3                    3<br>NeuAcα            Fucα            Fucα | 548 |
| 13-1 | 8 | Galβ4GlcNAcβ3Galβ4GlcNAcβ3Galβ4GlcNAcβ3Galβ4GlcNAcβ3Galβ4GlcβCer<br>3       3                    3<br>NeuAcα  Fucα            Fucα | 548 |
| 14§ | 9 | Galβ4GlcNAcβ3GalβGlcNAcβ3Galβ4GlcNAcβ3Galβ4GlcNAcβ3Galβ4GlcNAcβ3Galβ4GlcβCer<br>3                            3<br>NeuAcα                    Fucα | 548 |
| 14 | 10 | Galβ4GlcNAcβ3GalβGlcNAcβ3Galβ4GlcNAcβ3Galβ4GlcNAcβ3Galβ4GlcNAcβ3Galβ4GlcβCer<br>3                                        3<br>NeuAcα                                Fucα | 548 |
| 14 | 11 | Galβ4GlcNAcβ3GalβGlcNAcβ3Galβ4GlcNAcβ3Galβ4GlcNAcβ3Galβ4GlcNAcβ3Galβ4GlcβCer<br>3                    3                    3<br>NeuAcα            Fucα            Fucα | 660 |
| 14 | 12 | Galβ4GlcNAcβ3GalβGlcNAcβ3Galβ4GlcNAcβ3Galβ4GlcNAcβ3Galβ4GlcNAcβ3Galβ4GlcβCer<br>3                    3                    3<br>NeuAcα            Fucα            Fucα | 660 |

*Fraction numbers correspond to those used in our previous paper (Stroud MR, et al., submitted MS).
** This structure was isolated from colonic adenocarcinoma (Fukushi et al., 1984, J. Biol. Chem. 259:10511–10517).
†Molar ratio of Str. 4 and 5 present in Fr. 10 was 1:1.
‡Molar ratio of Str. 7 and 8 present in Fr. 13-1 was 100 < 1.
§Molar ratio of Str. 9, 10, 11, and 12 present in Fr. 14 was 5:1:3:1.

RESULTS

E-selectin-dependent adhesion under static conditions

Figure 1:
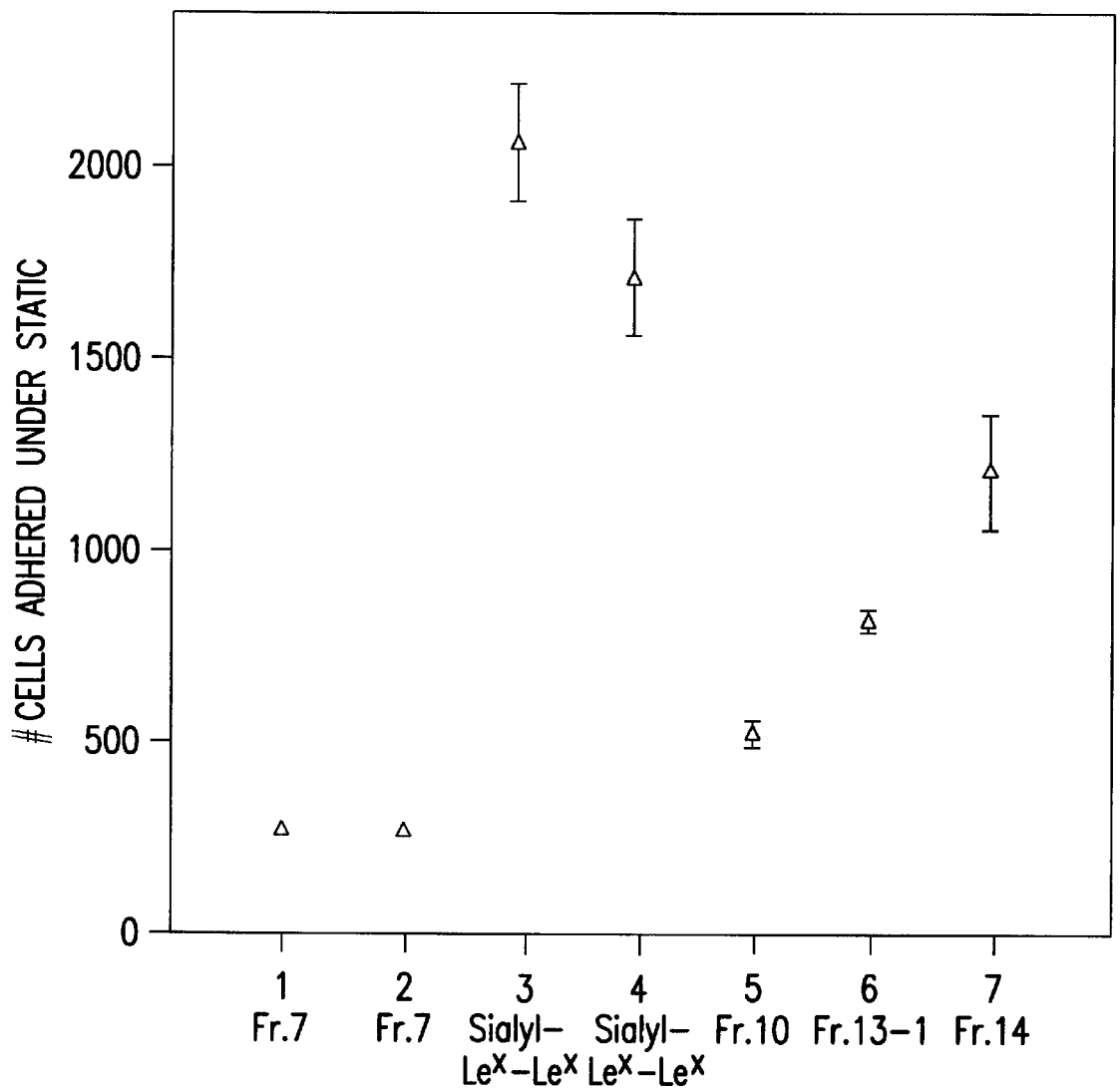
FIG. 1 shows adhesion under mixed conditions of E-selectin-expressing CHO cells to various gangliosides coated and affixed on polystyrene beads. The figure shows the results of static adhesion of E-selectin expressing cells on various ganglioside-coated plastic beads.

FIG. 1 shows adhesion under static conditions of E-selectin-expressing CHO cells to various gangliosides coated and affixed on polystyrene beads. Polystyrene latex beads were affixed on glass microscope slides, added with 1 nmol of ganglioside fraction dissolved in isopropanol-hexane-water (50:45:10), allowed to dry for 1 hr, and then immersed in PBS(+) containing 1% bovine serum albumin. The slides were placed in Petri dishes containing permanently E-selectin-expressing CHO cells ($1\times10^5$) in RPMI medium. After 30 min. incubation, slides were washed with PBS and total numbers of cells adhered on the affixed beads were counted. Sdiy$^2$ is sialyl-Le$^x$-Le$^x$ (VI$^3$NeuAcV$^3$FucIII$^3$FucnLc$_6$Cer). Structure of meylorollin indicated by fraction number is shown in Table 1 and FIG. 8.

Under these static conditions, E-selectin-expressing CHO cells did not bind to plates coated with latex beads coated with Str. 1 or 2 (Table 1). In contrast, a much higher number of cells bound to beads coated with Str. 3, which has SLe$^x$ determinant. Numbers of cells adherring to the mixture of Fr. 10-1 and Fr. 10-2 (containing Str. 4 and 5 (Table 1)), Fr. 13-1 (see above), and Fr. 14 (see above) were less than numbers binding to Str. 3 (Table 1) (which has SLe$^x$ structure) under these static conditions (FIG. 1).

Figure 1A:
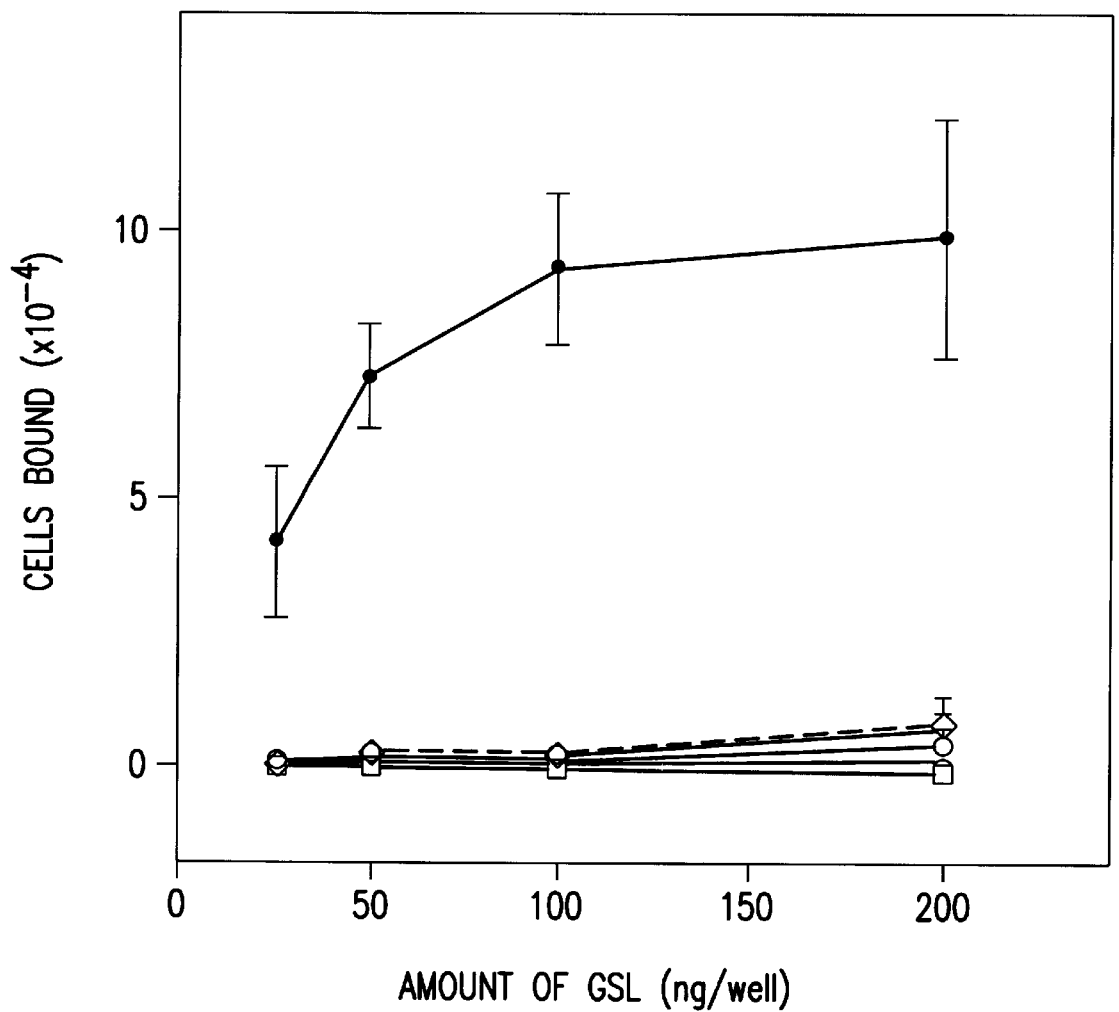
FIG. 1A shows adhesion under static conditions of E-selectin-expressing CHO cells to various gangliosides coated on wells on well plates. Adhesion of E-selectin-expressing CHO cells to various quantities of poly-LacNAc gangliosides coated on 96-well plates (Falcon, Becton-Dickinson, Lincoln Park, N.J.). Points represent mean experimental minus control value in the presence of mAb E1C, ±SE of triplicate experiments. ●SLe$^x$-Le$^x$, Δ Fr. 10-1, ▲ Fr. 10-2, □ Fr. 9, ○ Fr. 12-2. Only SLe$^x$-Le$^x$ but none of myelorollin was capable of binding E-selectin expressing cells under such static conditions.

Adhesion of E-selectin-expressing cells to myelorollin gangliosides and SLe$^x$-containing gangliosides was studied by two different methods as described in Materials & Methods: (i) Gangliosides are coated directly on 96-well plates followed by blocking by BSA, and [$^3$H]thymidine-labeled E-selectin-expressing cells are added and incubated in the presence and absence of anti-E-selectin antibodies. Results indicate that only SLE$^x$-Le$^x$, but no myelorollin, bound to E-selectin under these static conditions (FIG. 1A). (ii) Use of polystyrene beads (diameter 1 μm) affixed on glass microscope slides by fusion through heating at 150° C. for 2 min. Gangliosides were quantitatively adsorbed on the beads. To this matrix, non-radiolabeled E-selectin-expressing CHO cells were added, incubated, washed and number of adhered cells counted. Under these conditions, SLe$^x$-Le$^x$ showed greatest cell adhesion, followed in order by Fr. 13 and 14, which contain two fucose (Fuc) residues. Myelorollins containing one Fuc residue did not bind (FIG. 1B).

Figure 1B:
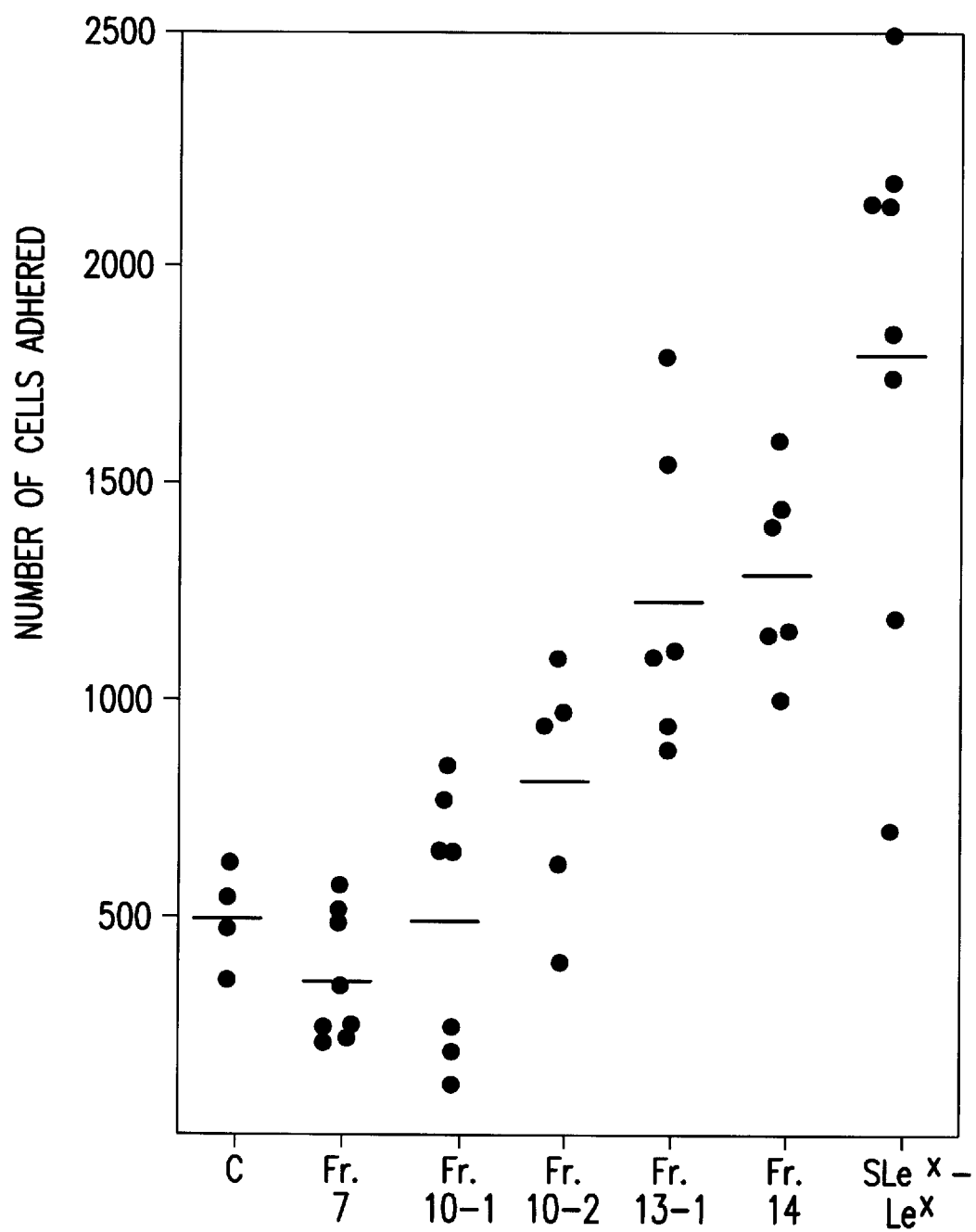
FIG. 1B shows adhesion under static conditions of E-selectin-expressing CHO cells to various gangliosides coated on wells on well plates. Polystyrene beads (1 μm diameter) were spread and affixed to glass microscope slides as described in Materials & Methods, added with 100 ng of poly-LacNac ganglioside dissolved in isopropanol-hexane-water (50:45:10), allowed to dry for 1 hr, and immersed in PBS containing 2% BSA. The slides were placed in Petri dishes and overlaid with RPMI medium containing E-selectin-expressing CHO cells (1×10$^5$/cells mL). After 10 min incubation, slides were washed with PBS and total numbers of cells adhered on beads were counted. Each point represents one experiment. Horizontal lines indicate arithmetic means.

Additional details of the experiment whose data are shown in FIGS. 1A and 1B are as follows: SLe$^x$-Le$^x$ and poly-LacNAc gangliosides (Frs. 7, 9, 10-1, 10-2, 12-2, 13-1 and 14) dissolved in 50% ethanol were appropriately diluted and coated on wells of 96-well plates (amounts of 25 to 200 ng as shown on abscissa). Wells were dried at 37° C. for 5 hr. Two identical plates (1 and 2) were prepared in this way. To each well of plate 1, 50 μL aliquots of RPMI containing $1\times10^5$ E-selectin-expressing CHO cells metabolically labeled with [$^3$H] thymidine were added. To each well of plate 2, aliquots of the same cell preparation preincubated with anti-E-selectin mAb E1C (10 μg Ig per mL) and suspended in RPMI containing mAb E1C were added. Plates 1 and 2 were incubated for 25 min. and washed with PBS. Experience showed that washing was best performed in the following manner. Each well was filled with 200 μL of PBS, carefully shaken, and plates were inverted on blotting paper for 10 min. All non-adherent cells were sedimented and absorbed on the blotting paper. Adherent cells remaining on wells were counted. Cell numbers (expressed on ordinate)

were calculated based on measured radioactivity. Solid circle, SLe$^x$-Le$^x$ without E1C (from plate 1). Open circle, SLe$^x$-Le$^x$ with E1C (from plate 2). Adhesion values from various poly-LacNAc gangliosides with and without E1C were all near zero and cannot be distinguished on the graph.

Important findings were that, under static conditions, SLe$^x$-Le$^x$ showed much stronger adhesion than myelorollin (Frs. 13-1 and 14), sialosyl-poly-LacNAc with single internal α1→3 fucosylation (Frs. 9, 10-1, 10-2 and 12-2) and sialosyl-poly-LacNAc without fucosylation (Fr. 7) showed little or no adhesion.

Direct binding of myelorollin to E- and P-selectin determined by flow cytometry

In our previous studies, poly-LacNAc gangliosides having two α1→3 Fuc residues (e.g. Fr. 12-3, 13-1, 14) were only capable of binding E-selectin under static conditions. We did not observe adhesion of poly-LacNAc gangliosides having a single α1→3 Fuc residue at internal GlcNAc (Fr. 9, 10, 12-1) to E-selectin under static conditions (Stroud et al., *Biochem Biophys Res Commun* 209:777–778, 1995; Stroud et al., *Biochemistry* 35:758–769; and Stroud et al., *Biochemistry* 35:770–778, 1996). These findings were confirmed through experiments shown in FIGS. 1A and 1B.

In contrast, under dynamic flow conditions, poly-LacNAc gangliosides having a single α1→3 Fuc residue at internal GlcNAc (Fr. 9, 10, 12-1) bound to and caused strong rolling of E-selectin-expressing cells. Since these myelorollin fractions are the major components of neutrophils and HL60 cells, it is important to confirm their E-selectin binding ability by other methods.

Adhesion under conditions of E- or P-selectin-binding to various gangliosides was assessed by a novel, sensitive method using E- or P-selectin-coated fluorescent beads (FIGS. 2 and 3). Adhesion was determined by aggregation of polystyrene beads coated with myelorollin, and selectin-coated fluorescent beads. Gangliosides were coated on non-fluorescent polystyrene beads and mixed with fluorescent beads coated with E- or P-selectin in the presence or absence of EDTA. Since aggregation occurs under brief, strong agitation, the process is neither "static" nor "dynamic" adhesion, in which myelorollin is presented as immovable solid phase. In this system, solid phases containing both myelorollin and selectin are in dynamic condition. Binding was determined by cytofluorometry. Ganglioside fractions used in this experiment were the same as described in Table 1. In addition: Sdiy$^2$, sialosyl Le$^x$-Le$^x$ (VI$^3$NeuAcV$^3$FucIII$^3$FucnLc$_6$Cer); SLe$^x$ (IV$^3$NeuAcIII$^3$FucnLc$_4$Cer). These designated structures are based on $^1$H NMR, mass spectrometry. Binding index was defined as mean fluorescence intensity (MFI) of ganglioside fraction divided by MFI of sialylparagloboside (IV$^3$NeuAcnLc$_4$Cer).

Referring to FIG. 2: open columns, E-selectin-IgG beads. Lighter shaded columns, E-selectin-IgG beads in the presence of 5 mM EDTA. Darker shaded columns, P-selectin-IgG beads. Solid columns, human IgG control beads. The binding of myelorollin to E-selectin beads was completely abolished in the presence of EDTA; myelorollin was unable to bind to P-selectin.

Under this standard assay method, a mixture of Str. 4 and 5 in Table 1, which have no SLe$^x$ terminus but are internally α1→3 fucosylated at GlcNAc-III and GlcNAc-V, bound strongly to E-selectin. Ganglioside Fr. 13-1 (containing Str. 7 as major and Str. 8 as minor component (see Table 1); ratio of Str. 7 to 8=10:1) and Fr. 14 containing myelorollin Str. 9-12 (Table 1) but not SLe$^x$) also showed clear binding. In contrast, Fr. 7 (containing Str. 1 in Table 1; α2→3 sialylnorhexaosylceramide) and Fr. 8 (containing Str. 2 in Table 1), which have no internal fucosylation, showed no binding to E-selectin. Str. 3 in Table 1, which has SLe$^x$ terminus with internal α1→3 fucosylation, did show binding, as expected.

FIG. 3 shows inhibitory effect of anti-E-selectin antibody on E-selectin binding to various myelorollin fractions. Binding index was defined as MFI of sample divided by MFI of sialylparagloboside as in FIG. 2. Open columns, E-selectin-IgG beads preincubated with control mouse IgG. Solid columns, E-selectin-IgG beads preincubated with mAb E1C. E1C was one of the anti-E-selectin mAbs selected based on inhibitory effect on E-selectin binding to HL60 cells. Sdiy$^2$ and SLe$^x$ are as defined for FIG. 2. The results shown in FIGS. 2 and 3 confirm that myelorollin having a single internal α1→3 fucosyl residue (e.g. Fr. 9, 10, 12) shows similar degree of adhesion as SLe$^x$-Le$^x$.

E-selectin-dependent cell binding to gangliosides affixed to latex bead-coated plates under dynamic flow conditions:

In contrast to the results described above, rolling and adhesion under dynamic flow conditions were observed with Fr. 10, 13-1, and 14 (containing Str. 4-5, Str. 7-8, and Str. 9-12 in Table 1, respectively). Rolling was strongest for Fr. 10 and 14, which have myelorollin structure and lack SLe$^x$ epitope (FIG. 4). Polystyrene beads were affixed to glass microscope slides. Various gangliosides were coated as described in Materials & Methods. Slides were blocked by placing 1% or 2% bovine serum albumin in PBS for 1 hr, and then assembled in a parallel laminar-flow chamber as described by Lawrence et al. (Lawrence et al., 1990, *Blood* 75:227–237) and outlined in Material & Methods. E-selectin-expressing CHO cells were freshly harvested and suspended (1×10$^5$ cells) in RPMI medium. The cell suspensions were placed in an infusion pump connected to the flow chamber, and infused into the assembly at various laminar flow rates. Cell movements were observed under phase-contrast microscope and recorded by videocassette recorder. Numbers of rolling cells in at least 10 microscope fields were counted, and average numbers were recorded. FIG. 4: Solid columns, SLe$^x$-Le$^x$ (same as Sdiy$^2$ in FIGS. 2 and 3). Shaded columns, fraction 10 ganglioside. Open columns, fraction 14 ganglioside.

Rolling was particularly evident at 2.4–4.8 dynes/cm$^2$ shear stress for these fractions. Str. 3 in Table 1 (sialyl Le$^x$-Le$^x$) produced no cell rolling. It did produce cell adhesion, but to a lesser extent than the myelorollin fractions under dynamic flow conditions. Str. 3 is absent in neutrophils and HL60 cells (see below). There was no cell adhesion to Str. 1 or 2 in Table 1.

The results of a similar experiment under dynamic flow conditions with Fr. 13 and Fr. 14 (see Table 1) are shown in FIG. 5. No rolling was observed on sialyl Le$^x$-Le$^x$ (solid column) regardless of shear stresses in a striking contrast to a remarkable rolling followed by adhesion observed with myelorollin Fr. 13-1 and Fr. 14. FIG. 5 shows results of the same experiment as in FIG. 4, but using fraction 13-1 and repeating fraction 14. Experimental design, same as in FIG. 4. Solid columns, SLe$^x$-Le$^x$. Shaded columns, fraction 13-1 ganglioside. Open columns, fraction 14 ganglioside. FIG. 5A summarizes the results shown in FIGS. 4 and 5.

E-selectin dependent plain rolling, rolling followed by adhesion and adhesion in a dynamic flow system under various shear stresses are compared in FIGS. 6A–6D. Cell rolling was not observed (or barely observed) on SLe$^x$-Le$^x$ coated matrix regardless of shear stresses (12 to 1.2 dynes/ cm$^2$). A small number of cells (less than 5/field) were adhered without rolling. In contrast, in the myelorollin coated matrix the number of plain rolling cells was clearly observed during shear stress conditions (4.8–12 dynes/cm$^2$). The number of cells showing plain rolling and rolling followed by adhesion was most clearly observed at 2.4 dynes/cm$^2$ for all types of myelorollin (Fr. 13-1, Fr. 14, and Fr. 10; Table 1). At shear stress conditions (0.6–1.2 dynes/cm$^2$) the number of rolling cells followed by adhesion greatly increased.

Figure 6B:
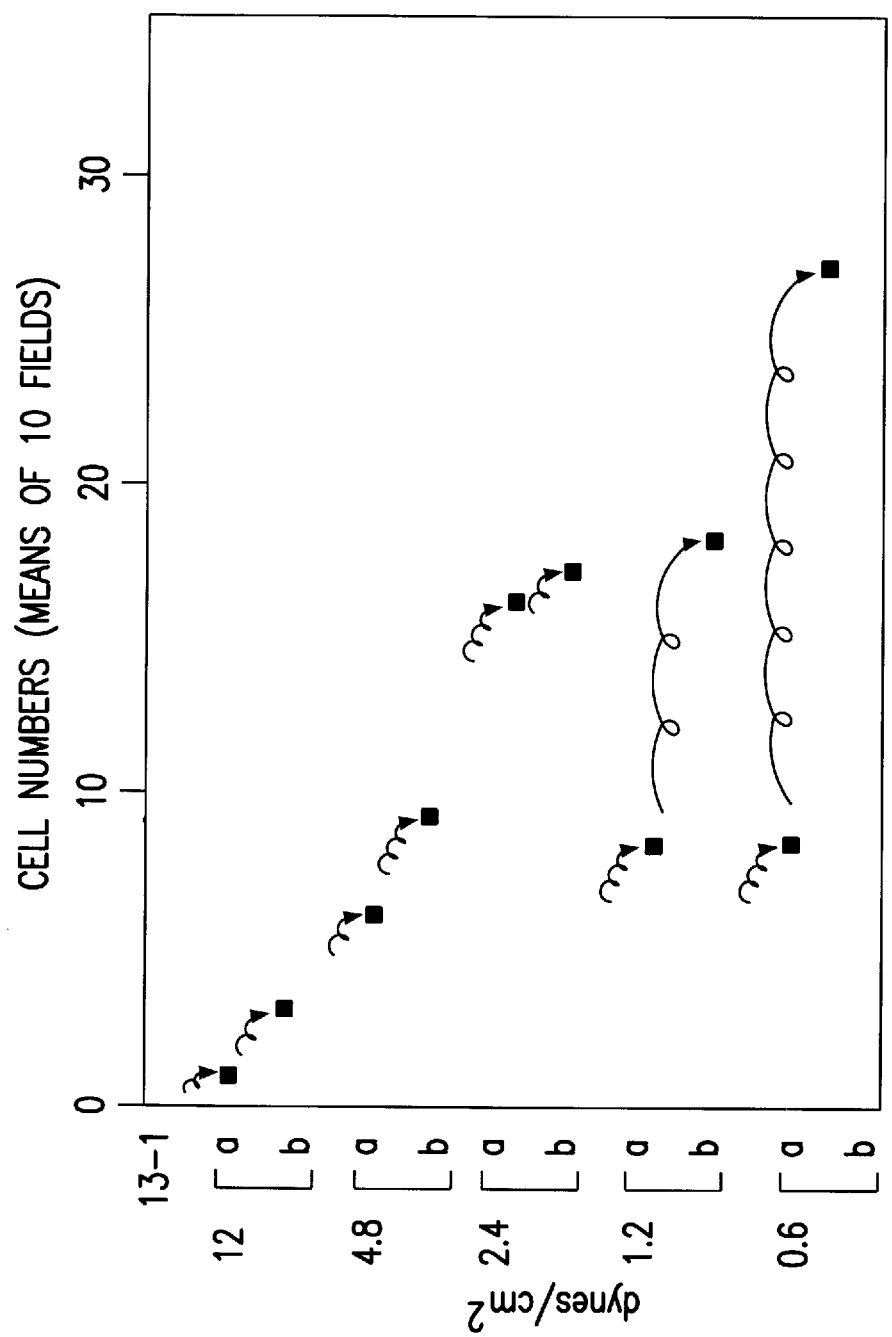
Figure 6C:
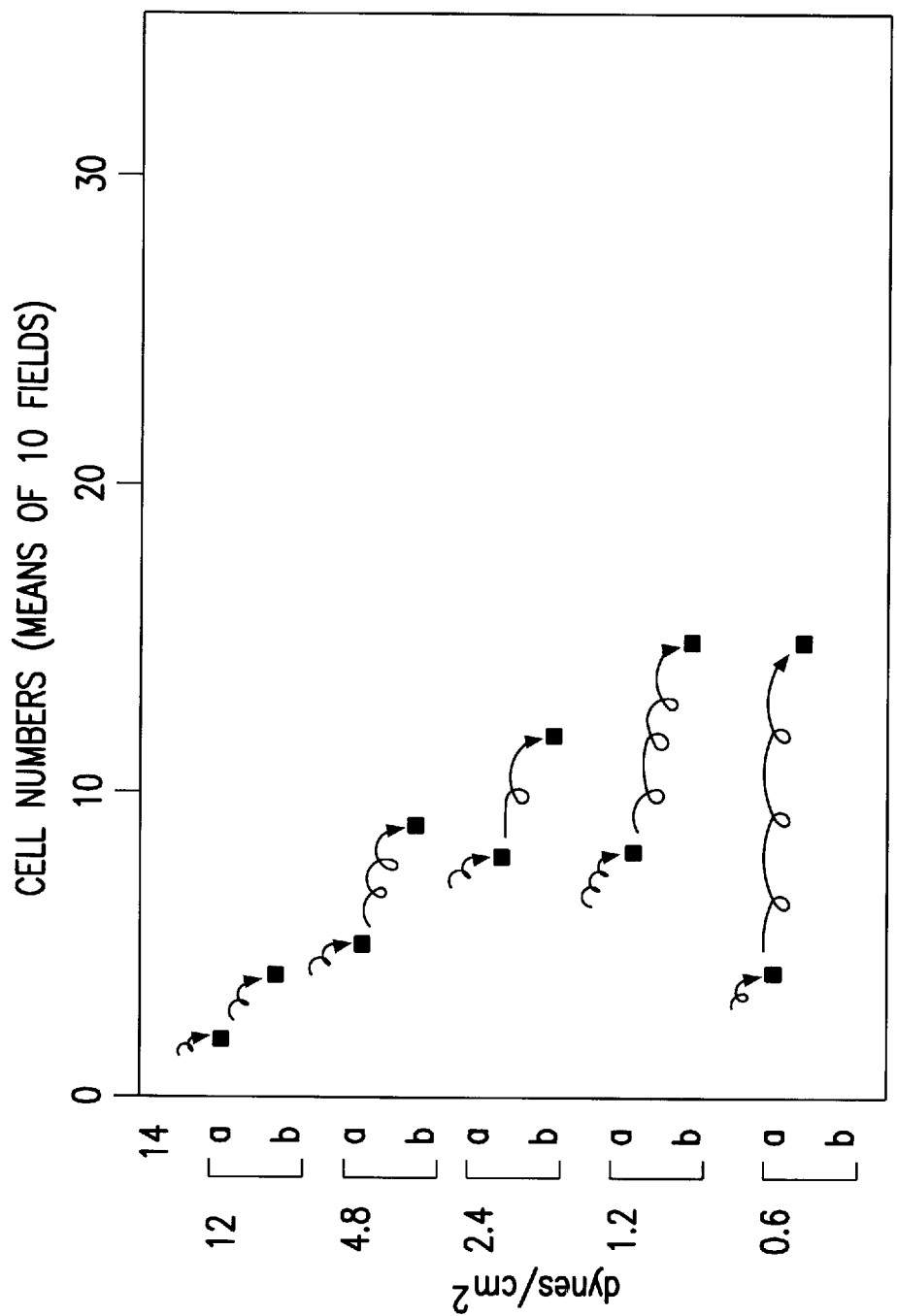
Figure 6D:
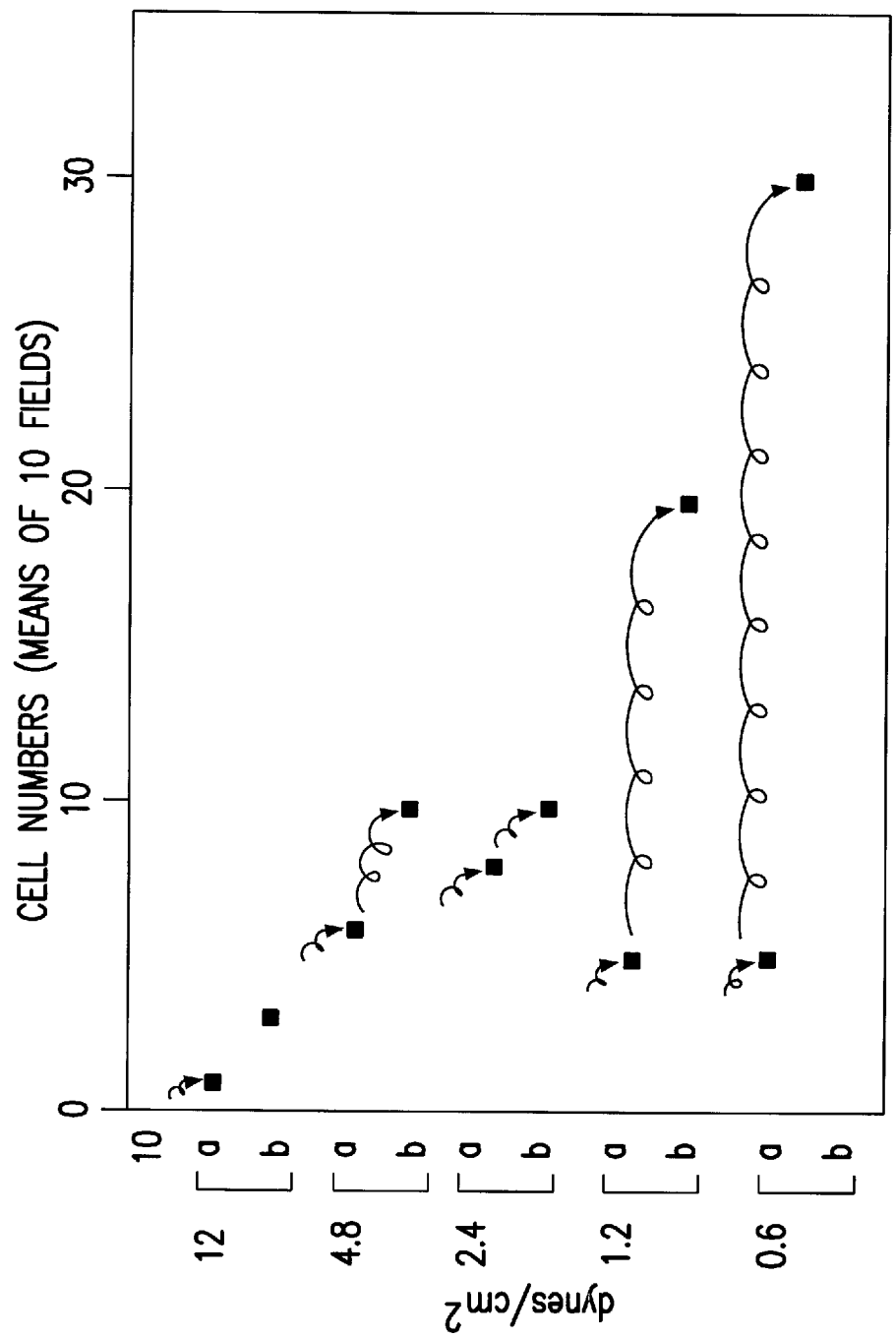

Referring to FIGS. 6A–6D in more detail, numbers of plain rolling cells and rolling cells followed by adhesion under defined wall shear stress conditions (12, 4.8, 2.4, 1.2 and 0.6 dynes/cm$^2$) is indicated by the coiled arrow symbol. FIG. 6A: cell adhesion to SLe$^x$-Le$^x$ (Sdiy$^2$). There was no rolling. Low level of adhesion without rolling was observed at 4.8 to 1.2 dynes/cm$^2$ shear stress. No variation in the number of adherent cells at different wall shear stresses. a, number of rolling cells; b, non-rolling adherent cell. FIG. 6B: plain rolling cell and rolling cell followed by adhesion to ganglioside fraction 13-1 (Structure 7 in Table 1). Rolling was maximal at 2.4 dynes/cm$^2$, and declined at lower shear stress. a, number of rolling cells; b, number of rolling cells followed by adhesion. FIG. 6C: plain rolling cell and rolling cell followed by adhesion to fraction 14, a mixture of Structures 9, 10, 11 and 12 in Table 1. High rolling followed by adhesion were observed at 2.4 to 1.2 dynes/cm$^2$. a, number of rolling cells; b, number of rolling cells followed by adhesion. FIG. 6D plain rolling cell and rolling cell followed by adhesion to the mixture of fraction 10-1 and 10-2, a mixture of Structures 4 and 5 in Table 1. Maximal rolling followed by adhesion were observed at 2.4 dynes/cm$^2$. a, number of rolling cells; b, number of rolling cells followed by adhesion.

Rolling and adhesion of E-selectin-expressing CHO cells under dynamic flow conditions FIGS. 2A–2E show the results under shear stress conditions similar to those in human vascular endothelium obtained by the experimental method as mentioned above. Numbers of total rolling cells (○) and numbers of total rolling and adhesion cells (●) found in at least 10 microscope fields, at four different shear stresses (dyne/cm$^2$; see abscissa), were plotted. Numbers of circles greater than 4 are simply represented as 4 on these figures. What are shown in these figures are:

FIG. 2A. Rolling and adhesion of cells on SLe$^x$-Le$^x$ absorbed on 4 μm beads. There were adherent, but not rolling (i.e. rolling number=0), cells in every field at all shear stresses.

FIG. 2B. Fr. 12-2 on 4 μm beads. Rolling was highest at 4.8 dynes/cm$^2$. Both rolling and adhesion were lower than for Frs. 13-1 and 14 (FIGS. 2C and 2E), but comparable to SLe$^x$-Le$^x$.

FIG. 2C. Fr. 13-1 (Str. 7 in Table 1) on 4 μm beads. Rolling was more frequent at 4.8 and 2.4 than at 1.2 dynes/cm$^2$.

FIG. 2D Fr. 13-1 on 1 μm beads. Rolling was highest at 4.8. Adhesion was higher and rolling was lower at 1.2.

FIG. 2E. Fr. 14 on 1 μm beads. Rolling and adhesion were highest at 2.4 and 4.8. Rolling was lower at 1.2.

Myelorollin analogs showed higher E-selectin-dependent rolling and adhesion than SLe$^x$-Le$^x$ under dynamic flow conditions at physiological shear stress:

100 ng of poly-LacNAc ganglioside (Fr. 13-1, Fr. 14 or SLe$^x$-Le$^x$) was adhered to beads affixed to microscope slides, which were then placed in the dynamic flow system as described in Material & Methods. We observed rolling and adhesion of E-selectin-expressing CHO cells in this system at various shear stresses. Trends of adhesion of poly-LacNAc gangliosides to beads with diameter 4 μm or 1 μm were essentially similar (FIGS. 2C and 2D). Fr. 13-1 and Fr. 14 produced strong rolling and adhesion at 4.8 or 2.4 dynes/cm$^2$. Number of rolling cells was lower at 1.2 dynes/cm$^2$ (FIGS. 2C, 2D and 2E). Number of adhering cells on beads coated with SLe$^x$-Le$^x$ was significantly lower than for Fr. 13-1 or 14. No rolling was observed with SLe$^x$-Le$^x$ (FIG. 2A).

A series of experiments on rolling/adhesion of E-selectin-expressing cells to various gangliosides under dynamic conditions indicate that SLe$^x$-containing structures do not cause rolling. Sialosyl poly-LacNAc having one α1→3 linked Fuc at different GlcNAc as found in Fr. 10 and 14 produced strong rolling. Fr. 13-1, which is essentially pure component having two α1→3 Fuc residues, also caused strong rolling. Rolling cells were counted, excluding adherent cells, and results shown in FIGS. 4 and 5 and summarized in FIG. 5A.

Myelorollin mixture causes better rolling and adhesion than purified components.

The data shown in FIGS. 4, 5, and 6A–6D under dynamic conditions are all a mixture of myelorollin. Fr. 11 is a pure compound representing Str. 6 in Table 1, which showed a weak adhesion, while Fr. 10 is a mixture of Str. 4 and 5 in Table 1, which showed a remarkable E-selectin binding (FIG. 2). Further studies indicate the "myelorollin mixture" displays a much higher capability of causing E-selectin-dependent rolling followed by adhesion than the purified compound (see Table 2).

Enhanced adhesion and rolling of cells on two poly-LacNAc gangliosides having fucosyl α1→3 linked at different GlcNAc residues.

Indicated are synergistic effects when myelorollin is combined, FIG. 3A.

Plot 1: Total rolling and adhesion (●) and total rolling (○) on 100 ng of Fr. 10-1 (Str. 4 in Table 1).

Plot 2: 100 ng of Fr. 10-2 (Str. 5 in Table 1).

Plot 3: Mixture of 500 ng each of Frs. 10-1 and 10-2.

Gangliosides were absorbed on 1 μm beads. Values for shear stresses of 4.8 and 2.4 dyne/cm$^2$ are shown. Statistical significance of differences between various subsets of data were evaluated by unpaired Student's t-test and P values are summarized in the inset table.

FIG. 3B

Plot 1: Adhesion and rolling on 0.1 ng of Fr. 10-1.

Plot 2: 0.1 ng of Fr. 10-2.

Plot 3: Mixture of 0.05 ng each of Frs. 10-1 and 10-2.

Gangliosides were absorbed on 1 μm beads. Three different shear stress values are shown. Rolling and adhesion occurred even at this low ganglioside concentration. Number of rolling and adhesion cells was greatest for the mixture of gangliosides (Plot 3). P values are summarized also in the inset table of FIG. 3B.

Frs. 10-1 and 10-2 were characterized as poly-LacNAc gangliosides having α1→3 fucosylation at GlcNAc-V and GlcNAc-III respectively. 100 ng of either fraction adhered to beads affixed on slides showed comparable rolling and Vadhesion at 4.8 and 2.4 dynes/cm$^2$ (FIG. 3A, Plots 1 and 2). An artificial mixture of 50 ng each of Fr. 10-1 and 10-2 produced much higher rolling and adhesion at these shear stresses (Plot 3). Statistical significance of differences between plots (P values from unpaired Student's t-test) are shown in the inset table on FIG. 3A.

Enhancement of rolling and adhesion by a mixture of Fr. 10-1 and Fr. 10-2, as compared to either fraction alone, was more evident when a 1000-fold smaller concentration was used (FIG. 3B). Fr. 10-2 at this small concentration (0.1 ng per spot) still produced marked rolling and adhesion (FIG. 3B, Plot 2), but Fr. 10-1 did not (Plot 1). Much higher rolling and adhesion at physiological shear stress (2.4–4.8 dynes/cm$^2$) was observed when a mixture of 0.05 ng each of Fr. 10-1 and Fr. 10-2 was used (Plot 3). Statistical significance between plots (P values from unpaired Student's t-test) are shown in the inset table on FIG. 3B.

Comparison of SLe$^x$-Le$^x$ with the mixture of Fr. 10-1+Fr. 10-2 at low concentration.

FIG. 4A, Plot 1. Total rolling and adhesion (●) and total rolling (○) of cells on 0.05 ng of SLe$^x$-Le$^x$ at shear stresses of 7.7, 3.1, and 1.5 dynes/cm$^2$. Plot 2. Replicate experiment, same conditions as Plot 1.

FIG. 4B, Plot 1. Mixture of 0.05 ng each of Fr. 10-1 and Fr. 10-2. Same shear stresses as in FIG. 4A. Plot 2. Replicate experiment, same conditions as Plot 1.

The experiment with 0.05 ng of SLe$^x$-Le$^x$ (the compound which produced strongest adhesion under static conditions) showed no rolling or adhesion under dynamic conditions in two replicate experiments (FIG. 4A, Plots 1 and 2). On the other hand the new experiment with 0.05 ng each of Fr. 10-1 and Fr. 10-2 again showed high rolling and adhesion at the same shear stresses in two replicate experiments (FIG. 4B, Plots 1 and 2). By further experiment using 0.1 ng of SLe$^x$-Le$^x$, there was no rolling and adhesion observed (data not shown).

DISCUSSION

Expression of E- and P-selectin on ECs in response to inflammatory stimuli causes interaction of ECs with neutrophils or other leukocytes, resulting in rolling followed by adhesion and transendothelial migration of leukocytes. E-selectin-dependent rolling followed by adhesion and E-selectin-dependent adhesion have been thought to be mediated by recognition of SLe$^x$ epitope expressed on leukocytes by E-selectin. This concept was based on various observations which, however, did not include unequivocal chemical identification of the real carbohydrate epitope present on neutrophils. Human neutrophils, other leukocytes, and leukemic leukocyte cell lines (HL60 and U937) show strong reactivity with various mAbs previously claimed to be directed to SLe$^x$. However, quantities of SLe$^x$ chemically detectable in these cells are extremely small. $^+$Ion FABMS of permethylated side chains of N-linked structures in leukemic leukocytes gave a barely detectable m/z 999 signal, representing SLe$^x$ structure (Fukuda et al., 1984, J. Biol. Chem. 259:10925–10935). The presence of SLe$^x$ in side chains of N- or O-linked structures in neutrophils or myelogenous leukemia cells was assumed (Asada et al., 1991, Biochemistry 30:1561–1571; Patel et al., 1994, Biochemistry 33:14815–14824), but was not supported by unambiguous chemical analysis.

Our recent systematic studies on gangliosides of normal human leukocytes and promyelogenous leukemia HL60 cells has indicated that only unbranched monosialogangliosides having cores with >10 sugars are responsible for E-selectin binding (Stroud et al., 1995, Biochem. Biophys. Res. Commun. 209:777–787). Gangliosides with SLe$^x$ structure (e.g., IV$^3$NeuAcIII$^3$FucnLc$_4$Cer, VI$^3$NeuAcV$^3$FucnLc$_6$Cer, VI$^3$NeuAcV$^3$-FucIII$^3$FucnLc$_6$Cer), which are abundantly present in various types of solid human cancer (Yang and Hakomori, 1971 J. Biol. Chem. 246:1192–1200; Fukushi et al., 1984, J. Biol. Chem. 259:10511–10517), were completely absent from leukocytes and HL60 cells. Among long-chain PLA lipids having 8-, 10-, or 12-sugar cores, structures having SLe$^x$ epitope without internal fucosylation (e.g. VIII$^3$NeuAcVII$^3$FucnLc$_8$Cer, X$^3$NeuAcIX$^3$FucnLc$_{10}$Cer, XII$^3$NeuAcXI$^3$FucnLc$_{12}$Cer) were completely absent. Instead, there were trace components having SLe$^x$ with internal fucosylation (e.g., X$^3$NeuAcIX$^3$FucVII$^3$FucnLc$_{10}$Cer) (Stroud et al., 1995, Biochem. Biophys. Res. Commun. 209:777–787). The major structures present in leukocytes and HL60 cells were a series of unbranched long-chain PLAs having terminal α2→3 sialylation and internal α1→3 fucosylation, with the representative structures A, B, C, D, X and Y shown below:

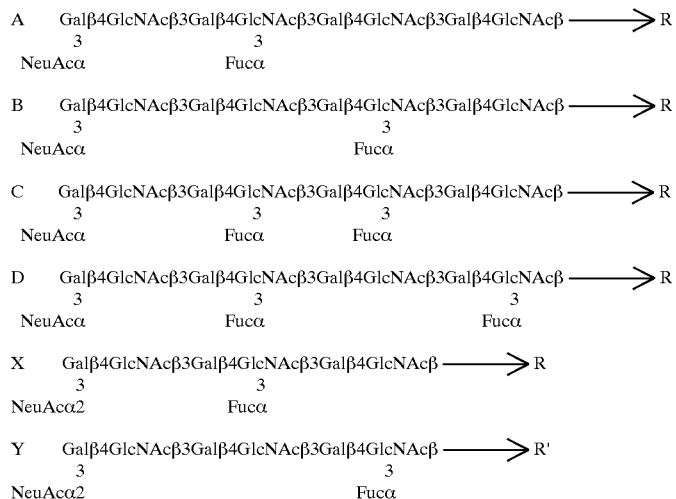

wherein → indicates covalent bond; R is a H atom, a substituted or unsubstituted aryl group, an alkyl, alkenyl or hydroxyalkyl group having 1 to 10 carbon atoms, a complex lipid, a simple lipid, an oligosaccharide, a ceramide residue, a pharmaceutically active ingredient, a solid carrier or a covalent compound thereof; R' is a H atom, a substituted or unsubstituted aryl group, an alkyl, alkenyl or hydroxyalkyl group having 1 to 10 carbon atoms, a complex lipid, a simple lipid, an oligosaccharide which does not contain any lactosamine residue, a ceramide residue, a pharmaceutically active ingredient, a solid carrier or a covalent compound thereof.

Structure A is common to Structure 4 and 6 in Table 1. Structure B is common to Structure 5 and 10 in Table 1. Structure C is common to Structure 7 and 11 in Table 1. Structure D is found in Structure 12 in Table 1. None of these four structures contains SLe$^x$ epitope.

Structure A was previously found in gangliosides isolated from chronic myelogenous leukemia cells (Fukuda et al., 1984, J. Biol. Chem. 259:10925–10935) and from human colonic cancer, and was identified as ACFH-18 antigen Nudelman et al., 1988, J. Biol. Chem. 263:13942–13951). Structure A was also identified as being defined by mAb "VIM-2" (Macher et al., 1988, J. Biol. Chem. 263:10186–10191), and was once claimed to be the E-selectin binding epitope (Tiemeyer et al., 1991, Proc. Natl. Acad. Sci. USA 88:1138–1142). However, VIM-2-positive, SLe$^x$-negative CHO cells showed no E-selectin-dependent adhesion (Lowe et al., 1991, J. Biol. Chem. 266:17467–17477; Walz et al., 1990, Science 250:1132–1135), indicating that VIM-2 epitope is not involved in such adhesion. A possibility for the VIM-2 antigen as a potential E-selectin ligand was denied by the fact that VIM-2 antibodies were unable to block adhesion and cells containing the VIM-2 antigen but not the SLe$^x$ structures were unable to bind to recombinant E-selectin and to activated endothelial cells (Lowe et al., 1991, J. Biol. Chem. 266:17467–17477; Walz et al., 1990, Science 250:1132–1135). In fact, ganglioside Str. 4 and 6 in Table 1, which have VIM-2 epitopes do not show appreciable adhesion under static conditions.

We now introduce a new assay based on interaction between latex beads coated with gangliosides and fluorescent beads coated with E- or P-selectin-Ig fusion protein. The interaction can be monitored easily by flow cytometry with appropriate gating. Using this assay, mixture of Fr. 10-1 and 10-2 (containing Str. 4 and 5 in Table 1), Fr. 13-1 (containing mainly Str. 7, in Table 1), and Fr. 14 (containing Str. 9 and 11 in Table 1 as major components) were found to bind strongly to E-selectin. Of particular importance is the observation that a mixture of different types of myelorollin greatly enhanced the rolling followed by adhesion. This is clearly demonstrated, not only by the flow cytometric method but also by cell adhesion in a dynamic flow chamber (see Table 2).

TABLE 2

| Number of E-selectin expressing cells adhered on myelorollin under dynamic flow (0.6–1.2 dynes/cm$^2$). | | |
| --- | --- | --- |
| | 5 | 10 |
| Str. 6[1] (ACFH 18 antigen) | 5 (±2) | 3 (±1) |
| Fr. 14 (mixture of Str. 9, 10, 11, and 12)[1] | 18 (±18) | 15 (±8) |

[1]Table 1

To summarize, Str. 1 and 2 in Table 1 (which have no internal fucosylation) showed no binding whatsoever. Among these fractions, only Fr. 13-1 contained a trace quantity of Str. 8 in Table 1 (which has SLe$^x$ determinant at the terminus, but also internal fucosylation). None of the other E-selectin-binding fractions contained SLe$^x$ epitope. As expected, Str. 3 in Table 1 (abundantly present in human solid cancers such as colonic, gastric, and lung carcinomas), having SLe$^x$ and internal fucosylation, bound to E-selectin. Monosialogangliosides having terminally α2→3 sialylated and internally α1→3 fucosylated PLAs are the major components of neutrophils and myelogenous leukemia cells, and are collectively termed "myelorollin." mAbs FH6 (Fukushi et al., 1984, J. Biol. Chem. 259:10511–10517), CSLEX (Fukushima et al., 1984, Cancer Res. 44:5279–5285), and SNH3 and SNH4 (Muroi et al., 1992, Blood 79:713–719), previously identified as being directed to SLe$^x$ determinant, were found to react with all myelorollins. There is no mAb specific to SLe$^x$, i.e., not cross-reacting with any myelorollin. The specificity of these mAbs is under investigation.

We compared rolling and adhesion of E- and P-selectin-expressing CHO cells to ganglioside-coated latex beads affixed to microscopic slides under dynamic flow and static conditions. Only myelorollin (in the mixture of Fr. 10-1 and Fr. 10-2, Fr. 13-1 or Fr. 14), produced rolling of cells followed by adhesion under dynamic flow conditions. Fr. 10 and 14, which consist only of myelorollin with no trace of SLe$^x$, showed the strongest rolling and adhesion effects, particularly at 0.6–2.4 dynes/cm$^2$ shear stress. Str. 3 (Table 1), which has SLe$^x$ epitope with internal fucosylation, produced a lower level of adhesion and no cell rolling. Under static conditions, in contrast, Str. 3 caused much higher adhesion than myelorollin.

Since cell adhesion following rolling (rolling followed by adhesion) is regarded as a characteristic feature of selectin-dependent rolling and adhesion (see citation 2 for review), we assume that myelorollin as present in Str. 4, 5, 7 10, 11, in Table 1 etc. without SLe$^x$ determinant plays a major role in adhesion of leukocytes, mediated by selectin expression on ECs. This conclusion is based on the facts that: (i) Myelorollin is the major structure present in leukocytes and HL60 cells. (ii) Only myelorollin (not SLe$^x$ with or without internal fucosylation) produces cell rolling followed by adhesion. (iii) SLe$^x$ without internal fucosylation is completely absent from neutrophils and HL60 cells.

In our study, under static conditions only fractions with terminal α2→3 sialylation and multiple internal α1→3 polyfucosylation (e.g. C and D above, or a mixture of these structures) showed clear E-selectin binding upon application of TLC overlay technique with $^{32}$P-labeled CHO cells permanently expressing E- or P-selectin. These binding properties were confirmed in a static adhesion assay system using E-selectin-expressing CHO cells overlaid on glycolipids coated on polystyrene beads affixed to glass plates. Glycolipid with typical SLe$^x$ structure (SLe$^x$-Le$^x$; VI$^3$NeuAcV$^3$FucIII$^3$FucnLe$_6$Cer) showed highest adhesion in the static system. In contrast, in a dynamic flow system using the same glycolipid-coated beads affixed to glass plates, SLe$^x$-Le$^x$ produced no rolling and only weak adhesion compared to Fr. 10-1, 10-2, 13-1 and 14. Strong rolling and adhesion of cells were observed when structures X and Y were used. Typical examples are Fr. 10-1, 10-2, Fr. 13-1 and Fr. 14 (mixture of A, B, C and D) also produced strong rolling and adhesion under physiological shear stress conditions.

Given the finding that a mixture of myelorollin structures (e.g. Fr. 14) produces the strongest rolling and adhesion under physiological shear stress conditions, we closely investigated Fr. 10-1, Fr. 10-2 and a mixture of equal quantities of Frs. 10-1 and 10-2. Rolling and adhesion caused by 100 ng of pure Fr. 10-1 and Fr. 10-2 under physiological shear stress were comparable to each other. Interestingly, a mixture of 50 ng each of these two components produced much higher rolling and adhesion, particularly under physiological shear stress. This trend was more evident when much smaller quantities of glycolipids were applied. The most dramatic enhancement was seen when 0.05 ng each of 10-1 and 10-2 were used, compared to 0.1 ng of either component alone. These findings suggest that extremely small quantities of Frs. 10-1 and 10-2 may interact with each other to form a suitable structure for E-selectin causing rolling and adhesion under dynamic flow conditions. The mechanism for this synergistic effect remains unknown.

SLe$^x$-Le$^x$ structure, which produced the strongest E-selectin-dependent adhesion under static conditions, was weaker than myelorollin structures under dynamic flow conditions (FIGS. 2A vs. FIGS. 2C, 2D and 2E). The difference was even more striking at very low concentration. SLe$^x$-Le$^x$ at a concentration of 0.05 ng caused essentially no cell rolling and adhesion (FIG. 4A), whereas a mixture of Fr. 10-1 and 10-2 (0.05 ng each, giving the same molarity as 0.05 ng SLe$^x$-Le$^x$) caused strong rolling and adhesion (FIG. 4B). The enhancement by a mixture of Fr. 10-1 and 10-2 compared to either fraction alone was more pronounced when low (0.05–0.1 ng) rather than high concentration (50–100 ng) was used. In contrast to the effects of Fr. 10-1 and 10-2, SLe$^x$-Le$^x$ at low concentration (0.05–0.1 ng) did not cause any E-selectin-dependent cell rolling or adhesion.

These results indicate that myelorollin, rather than SLe$^x$-Le$^x$, is the major ligand for E-selectin-dependent rolling and adhesion of myeloid cells on vascular endothelial cells under physiological dynamic flow conditions.

Poly-LacNAc is known to form helical structures. Myelorollin may have helical backbone structures onto which multiple or single fucosyl residues are linked and oriented in different directions. Such helical structures, based on the positioning of the fucosyl residues, could interact with each other.

Throughout this study, P-selectin-dependent binding was not observed with any of the gangliosides tested, by either flow cytometric methods as described above or by adhesion of P-selectin-expressing CHO cells to ganglioside-coated plates, either under static or dynamic flow conditions. P-selectin-dependent adhesion clearly requires a "PSGL-1-like" assembler molecule in addition to specific carbohydrate structure (Handa et al., 1995 Int. J. Oncol. 6:773–781; Sako et al., 1993, Cell 75:1179–1186). Further studies on the carbohydrate epitope required for P-selectin binding are in progress.

Myelorollin

Consistent with the data presented above, myelorollin is embodied by the following structure, which encompasses a group of unbranched polylactosamines consisting of at least 8 monosaccharides (three lactosamine repeating units are shown) and having terminal α2→3 sialylation and internal α1→3 fucosylation at various N-acetylglucosamine residues except for solely at the penultimate N-acetylglucosamine residue:

$$\begin{array}{c} \text{Galβ4GlcNAcβ(3Galβ4GlcNAcβ)}_{2-1}\text{→R} \\ 3 \phantom{xxxxxxxxxx} | \\ 2 \phantom{xxxxxxxxxx} | \\ \text{NeuAcα} \phantom{xxxx} (\text{R}^1)_{1-3} \end{array}$$

wherein each $R_1$ is independently selected from among —OH and α1→3 fucose ($C_6H_{12}O_5$), provided that at least one $R_1$ is α1→3 fucose.

That is, in addition to Structures A, B, C, D, X and Y, the following monosialyated polylactosamines E, F, and G are also considered to present the myelorollin epitope of E-selectin:

$$\begin{array}{c} \phantom{xxxxxxxxxxxxxxxxxxxxxxxxxxxxxxxxxxxxxx} \text{E} \\ \text{Galβ4GlcNAcβ3Galβ4GlcNAcβ3Galβ4GlcNAcβ3Galβ4GlcNAcβ→R} \\ 3 \phantom{xxxxxxxxxxxxxxxxxxxxxxxxxxxxxxxxx} 3 \\ \text{NeuAcα} \phantom{xxxxxxxxxxxxxxxxxxxxxxxxx} \text{Fucα} \end{array}$$

$$\begin{array}{c} \phantom{xxxxxxxxxxxxxxxxxxxxxxxxxxxxxxxxxxxxxx} \text{F} \\ \text{Galβ4GlcNAcβ3Galβ4GlcNAcβ3Galβ4GlcNAcβ3Galβ4GlcNAcβ→R} \\ 3 \phantom{xxxxxxxxxxxxxxxx} 3 \phantom{xxxxxxxxxx} 3 \\ \text{NeuAcα} \phantom{xxxxxxxxx} \text{Fucα} \phantom{xxxxx} \text{Fucα} \end{array}$$

$$\begin{array}{c} \phantom{xxxxxxxxxxxxxxxxxxxxxxxxxxxxxxxxxxxxxx} \text{G} \\ \text{Galβ4GlcNAcβ3Galβ4GlcNAcβ3Galβ4GlcNAcβ3Galβ4GlcNAcβ→R} \\ 3 \phantom{xxxxxxxx} 3 \phantom{xxxxxx} 3 \phantom{xxxxx} 3 \\ \text{NeuAcα} \phantom{xxx} \text{Fucα} \phantom{xx} \text{Fucα} \phantom{xx} \text{Fucα} \end{array}$$

Furthermore, the following hybrid (Structure H) of SLe$^x$ and the myelorollins described above also presents myelorollin epitope of E-selectin:

$$\begin{array}{c} \phantom{xxxxxxxxxxxxxxxxxxxxxxxxxxxxxxxxxxxxxx} \text{H} \\ \text{Galβ4GlcNAcβ3Galβ4GlcNAcβ3Galβ4GlcNAcβ3Galβ4GlcNAcβ→R} \\ 3 \phantom{x} 3 \phantom{xxxx} 3 \phantom{xxxxx} 3 \phantom{xxxxx} 3 \\ \text{NeuAcα Fucα} \phantom{xx} \text{Fucα} \phantom{xx} \text{Fucα} \phantom{xx} \text{Fucα} \end{array}$$

Thus, the myelorollin epitope is embodied by the following structure, which encompasses a group of unbranched polylactosamines consisting of at least 10 monosaccharides and having terminal α2→3 sialylation and internal α1→3 fucosylation at various N-acetylglucosamine residues except for solely at the penultimate N-acetylglucosamine residue:

$$\begin{array}{c} \text{Galβ4GlcNAcβ(3Galβ4GlcNAcβ)}_a\text{→R} \\ 3 \phantom{xxxxxx} | \phantom{xxxxxxx} | \\ \text{NeuAcα2} \phantom{xx} \text{R}^2 \phantom{xxxxx} (\text{R}^1)_b \end{array}$$

wherein $R_1$ is a α1→3 fucose, $R_2$ is either —OH or fucose, a is an integer of from 2 to 6, b is an integer of from 1 to 6.

Such myelorollin mimetics which depart from the representative structures A, B, C, D and X, Y above may be further defined in terms of possible spatial arrangements (FIGS. 7A–7C) of sialosyl residues (SA) and fucosyl residues at the internal GlcNAc of different positions (Fuc 1 and Fuc 2) along the polylactosamine chain. Poly-N-acetyllactosamine chain ([Galβ1→4GlcNAcβ1→|$_n$) is known to have a helical structure (Niemann et al., 1978, Biochem. Biophys. Res. Commun. 81:1286–1293; Rees, D. A., 1975, MTP International Review of Science 5:1–42, ed. Whelan, W., Butterworths (London) University Park Press (Baltimore); Atkins et al., 1974, Polymer 15:263–271).

A: possible configuration of double helical structure of monofucosylgangliosides having Fuc1 of Fuc2 at different positions (e.g., Str. 4 and 5 or Str. 9 and in Table 1). When this structure is viewed from the terminal end where SA are present, the spatial arrangement of SA and Fuc 1, Fuc 2 can be seen as shown in I (lower panel).

B: possible configuration of double helical structure of difucosylgangliosides having Fuc 1 and Fuc 2 at different positions but on the same polylactosamine chain (e.g., Str. 7, Str. 11 of Table 1). When the structure is viewed from the terminal end where SA are present the spatial arrangement of SA and Fuc 1 and 2 can be shown as in II (lower panel).

C: SLe$^x$ structure where Fuc is present at the penultimate GlcNAc (Fuc x); the positional relationship between SA and Fuc x is seen as shown in III (bottom).

The above hypothesis has been supported by minimum energy configuration model constructed by SYBYL modeling.

Proposed hypothetical schemes for assembly of sialic acid (SA) and fucosyl residue (Fuc) on polylactosamine chain of myelorollin are shown in FIG. 7. Repetitive Galβ1→4GlcNAcβ1→3Galβ1→4GlcNAcB1→3Gal forms a helical structure (Atkins et al., Polymer 15:263–271, 1974; Rees D. A., MTP Intl Review of Science 5:1–42, 1975; Niemann et al., Biochem Biophys Res Commun 81:1286–1293, 1978). There is a high possibility that double or triple helical structure is formed through hydrogen bonding (Rees D. A., MTP Intl Review of Science 5:1–42, 1975; Frey-Wyssling A., *Submicroscopic morphology of protoplasm*, Elsevier Publ. Co., Amsterdam, 1953). Scheme A: possible double helical association of two myelorollin molecules having a single Fuc at different internal GlcNAc residues (locations designated as 1 and 2; Fuc residues designated at "Fuc 1" and "Fuc 2"). Scheme B: possible double helical association of two identical myelorollin molecules each having two Fuc residues; one each at locations 1 and 2; residues designated "Fuc 1" and "Fuc 2" as above. Scheme C: SLe$^x$ having Fuc "x" at the penultimate GlcNAc.

Rolling/adhesion of E-selecting-expressing cells under dynamic conditions is presumably controlled by spatial configuration and interrelationship of SA and Fuc: their angle distance, and orientation along helical polylactosamine backbone.

A possible configuration and interrelationship between SA and Fuc viewed along the axis of the helical backbone is shown at the bottom of FIG. 7 (I corresponds to Scheme A; II to Scheme B; III to Scheme C). Configuration I, formed between two myelorollin molecules having different Fuc locations (Fuc 1[black] and Fuc 2 [white]) may greatly enhance rolling and adhesion abilities, as exemplified by the mixture of Fr. 10-1 and 10-2. Perhaps Fuc 1 and Fuc 2 are located at symmetrical positions along the helical polylactosamine backbone as shown.

Rolling/adhesion ability between myelorollin molecules associated as in Scheme B and viewed along the axis as in II is nearly the same as for two molecules associated as in Scheme A. Perhaps Fuc 1 and Fuc 2 on the two molecules are located at symmetrical positions as shown in II.

SLe$^x$ may have a very different configuration (Scheme C; view III), and fail to cause rolling.

The present invention provides a method of inhibiting cell interactions comprising exposing a first cell, such as human neutrophils or leukocytes, that expresses a ligand that causes rolling and adhesion dependent on E-selectin expressed on a second cell, such as endothelial cells and other E-selectin expressing cells, to an E-selectin-dependent rolling and adhesion inhibiting amount of at least one unbranched polylactosamine comprising at least 8 monosaccharides and having terminal α2→3 sialylation and internal α1→3 fucosylation at various N-acetylglucosamine residues except for solely at the penultimate N-acetylglucosamine residue.

Further, the present invention provides a method of inhibiting cell interactions comprising exposing a first cell, such as human neutrophils or leukocytes, that expresses a ligand that causes rolling and adhesion dependent on E-selectin expressed on a second cell, such as endothelial cells and other E-selectin expressing cells, to an E-selectin-dependent rolling and adhesion inhibiting amount of an antibody that binds to an unbranched polylactosamine comprising at least 8 monosaccharides and having terminal α2→3 sialylation and internal α1→3 fucosylation at various N-acetylglucosamine residues except for solely at the penultimate N-penultimate N-acetylglucosamine residue, wherein said antibody is further characterized by inhibiting adhesion of said first and second cells under dynamic flow conditions in vitro.

Myelorollin preparation from HL60 cells

HL60 cells. HL60 cells were obtained originally from American Type Culture Collection (ATCC) and grown in RPMI supplemented with 10% FCS. Cells were maintained in 5% $CO_2$ at 37° C., expanded for two cycles in roller bottles to collect large amounts of cells, and harvested by centrifugation. HL60 cells cultured in this manner showed a level of E-selectin binding activity similar to that of cells cultured continuously in a $CO_2$ incubator, i.e., large-scale culture in roller bottles in this way did not cause significant loss of E-selectin binding activity. Altogether, 1200 mL of packed HL60 cells were divided into about 400 mL packed aliquots, each of which was extracted as described in the following section.

Glycolipid extraction. Approximately 100 mL of packed human neutrophils or 400 mL of packed HL60 cells were extracted by homogenization in a Waring blender with 10 volumes of the lower phase of IHW (55:25:20). The extract was filtered through a Whatman #1 filter and the residue re-extracted as above. The extraction/filtration procedure was repeated once more and the combined filtrates were concentrated under reduced pressure at 40° C. using a Brinkmann rotary evaporator. The concentrated extract was subjected to Folch partitioning by dissolving the residue in 3 L of chloroform/methanol (C/M; 2:1) containing 500 mL of water. After vigorous shaking the extract was allowed to separate until two translucent phases appeared (about 8 hr). The upper phase was removed and the lower phase re-extracted by the addition of C/M/1% KCl (1:10:10) to the original volume. The liquid-extraction procedure was repeated 2× and the combined upper phases were concentrated by rotary evaporation, reconstituted in water, and dialyzed exhaustively against deionized water using Spectropor 3 dialysis tubing (MW cutoff=3500).

Anion-Exchange Chromatography. After dialysis the upper-phase extract was evaporated to dryness as above and dissolved in 50 mL of C/M/water (30:60:8) by a combination of warming (37° C.) and sonication. Insoluble material was removed by centrifugation at 1000×g for 10 min and re-extracted by sonication in an additional 50 mL of the same solvent. Following centrifugation as above the combined supernatants were loaded onto a DEAE-Sephadex column (300 mL bed volume; acetate form) and washed with 2 L of C/M/water (30:60:8) to remove all neutral lipids. The column was equilibrated with 500 mL methanol and the monosialoganglioside fraction eluted with 2 L 0.05M $NH_4OAc$ in methanol. Subsequent removal of di-, tri-, and polysialosylgangliosides was achieved by eluting batch wise with 0.15M, 0.45M, and 1.0M $NH_4OAc$, respectively. The eluted ganglioside fractions were dried by rotary evaporation, dialyzed against water, and dried as above.

Purification of Monosialogangliosides from HL60 Cells:

High Performance Liquid Chromatography. The monosialoganglioside fraction was solubilized in 10 mL of IHW and transferred from the evaporation flask to a 15 mL tube. The sample was completely dried under $N_2$ using an N-EVAP (Organomation Inc.) and reconstituted in 2 mL of IHW by sonication. The sample was injected onto a preparative Iatrobead column (6RS-8010; 0.8×60 cm; Iatron Laboratories Inc., Kanda/Tokyo, Japan) pre-equilibrated with IHW (55:40:5), and subjected to a linear gradient from IHW 55:40:5 to 55:25:20 with a flow rate of 1 mL/min. 4 mL fractions were collected over 400 min. Each fraction was spotted onto an HPTLC plate, developed in an appropriate solvent system (described below), visualized by spraying with 0.5% orcinol in 2N sulfuric acid, and pooled according to migration. Pooled fractions containing more than one band by TLC were dried under $N_2$, resolubilized in 1 mL of IHW, and injected onto a semi-preparative Iatrobead column (0.4×60 cm). A linear gradient from IHW 55:40:5 to 55:25:20 over 200 min with a flow rate of 0.5 mL/min was used. 1 mL fractions were collected and pooled according to HPTLC migration. Fractions containing a single band by HPTLC were labeled according to order of migration in C/M/0.5% $CaCl_2$ (50:55:19); i.e., the fastest migrating band was labeled #1 and the slowest #20. Fractions containing multiple bands were further purified by preparative HPTLC.

High Performance Thin Layer Chromatography. Monosialoganglioside fractions that were not resolved into single bands by HPTLC were separated by preparative HPTLC. Fractions within bands 1 to 7 were resolved in a solvent system of C/M/0.5% $CaCl_2$ (50:40:10). Fractions within bands 8–14 were resolved in C/M/0.5% $CaCl_2$ (50:55:19). Fr. 12 and 13 were further resolved (into Fr. 12-1 through 12-5 and 13-1 through 13-3 respectively) using a solvent system of isopropanol/water/$NH_4OH$ (6:3.2:1). Preparative TLC was performed by streaking 50 μL of sample across a 10×20 cm HPTLC silica gel plate (silica gel 60; EM Science, Gibbstown, N.J.), dried, and developed in the appropriate solvent system. Plates were dried, and bands were visualized by spraying with 0.03% primulin in 80% acetone. Bands were marked with a pencil under UV light. Marked bands were scraped from the plate using a razor blade, and gangliosides were extracted from the silica by sonicating for 20 min in IHW (55:25:20; 2 mL per band). The silica was removed by centrifuging at 1000×g for 10 min, re-extracted as above, and the combined supernatants were dried under $N_2$. Samples were cleaned up using 1 cc tC-18 Sep-Pak cartridges (Waters, Milford, Mass.) by first dissolving the sample in 1 mL of PBS and then applying it to a column preequilibrated with PBS after sequentially washing with 5 mL methanol and 5 mL water. Once the sample was retained, the column was washed with 10 mL of water followed by 10 mL 50% methanol, and eluted in 10 mL 100% methanol. The sample was dried under $N_2$, dissolved in 1 mL of IHW (55:25:20), and injected onto an Iatrobead column (0.4×60 cm) as above using a linear gradient from IHW 55:40:5 to 55:25:20 for 100 min at a flow rate of 1 mL/minute. One mL fractions were collected and visualized by HPTLC using the orcinol-sulfuric acid reaction. Orcinol-positive fractions were pooled and dried under $N_2$ prior to structural analysis.

Antibody preparation

Balb/c mice are immunized by human neutrophils or HL60 cells by either intravenous or intraperitoneal repeated injections followed by a booster injection with monosialogangliosides containing myelorollin fraction adsorbed on *Salmonella minnesota* as previously described (Fukushi et al., 1984, J. Biol. Chem. 259:10511–10517; Nudelman et al., 1988, J. Biol. Chem. 263:13942–13951). After three days of booster injections, spleen cells were harvested and fused with NS-1 and the hybridoma was screened through a binding assay with 98-wells coated with purified myelorollin and those coated with $SLe^x$ or sialosyl paragloboside. Hybridoma secreting antibodies that react specifically with a myelorollin coated plate, but not with $SLe^x$ or sialosyl paragloboside coated plates, were cloned. Expansion of a clone followed by recloning with the specific reactivity of myelorollin is necessary.

Therapeutic administration

The anti-inflammatory myelorollin compositions of the present invention are administered to a subject in need thereof for prophylactically preventing inflammation or relieving it after it has begun. The subject myelorollin compositions are preferably administered with a pharmaceutically acceptable carrier, such as included in liposomes or bound to carrier specific molecules with the appropriate design, the nature of which differs with the mode of administration. For example, oral administration usually requires a solid carrier, although "mimetics" of myelorollin are constructed when orally administered, while intravenous administration usually requires a liquid salt solution carrier or liposome suspension. Typically, injectable compositions are prepared as liquid solutions or suspensions; solid forms suitable for solution in, or suspension in, liquid vehicles prior to injection may also be prepared. The compounds may also be emulsified or the active ingredient encapsulated in liposome vehicles, which is more desirable for display of higher activity.

Suitable vehicles are, for example, water, saline, dextrose, glycerol, ethanol or the like, and combinations thereof In addition, if desired, the vehicle may contain minor amounts of auxiliary substances such as wetting or emulsifying agents or pH buffering agents. Actual methods of preparing such dosage forms are known, or will be apparent, to those skilled in the art. See, for example, Remington's Pharmaceutical Sciences, Mack Publishing Company, Easton, Pa., 17th edition, 1985.

Pharmaceutically acceptable formulations may employ a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the subject myelorollin molecules directly in transdermal formulations with permeation enhancers such as DMSO. Other topical formulations can be administered to treat dermal inflammation. In addition, transmucosal administration may be effected using penetrants such as bile salts or fusidic acid derivatives optionally in combination with additional detergent molecules. These formulations are useful in the preparation of suppositories, for example, or nasal sprays. For suppositories, the vehicle composition will include traditional binders and carriers, such as polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject ligands by the nasal mucosa.

Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

In determining the dose to be administered, it will be noted that it may not be desirable to completely block all selectin molecules. In order for a normal inflammatory process to proceed, at least some of the white blood cells or neutrophils must be brought into the tissue in the areas where any wound, infection or disease state is occurring. The amount of the selectin ligands administered as blocking agents must be adjusted carefully based on the particular needs of the patient while taking into consideration a variety of factors such as the type of disease that is being treated.

Where the anti-inflammatory composition of the claimed invention is an antibody directed against a myelorollin, a pharmaceutically acceptable diluent can be employed and the antibody should be "humanized" and FAB fragmented. The particular pharmaceutically acceptable diluent employed is not critical thereto. Examples of such diluents include physiological saline, Ringer's solution, vitamin cocktail, and amino acid vitamin cocktail.

The pharmaceutically effective amount of the antibodies of the present invention to be administered will vary depending upon the age, weight, and sex of the subject to be treated. Generally, the pharmaceutically effective amount is about 1.0 to 5.0 $\mu$g/100 g body weight per one injection. Generally, from 5 to 10 injections of the antibodies are employed but the present invention is not limited thereto.

The compounds of the present invention are useful to treat a wide range of diseases, for example autoimmune diseases such as rheumatoid arthritis and multiple sclerosis. The compositions of the invention are applicable to treat any disease state wherein the immune system turns against the body causing the white cells to accumulate in the tissues to the extent that they cause tissue damage, swelling, inflammation and/or pain, particularly chronic inflammatory conditions that are E-selectin mediated.

Formulations of the present invention might also be administered to prevent the undesirable after effects of tissue damage resulting from acute inflammatory conditions inducing heart attacks. This is particularly desirable in combination with P-selectin inhibitors or P-selectin ligands, since P-selectin, but not E-selectin, plays a major role in acute inflammatory responses such as heart attacks or strokes. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated endothelial cells then synthesize the ELAM-1 receptors, a type of selectin, within hours of the cells being damaged. The receptors are extended into the blood vessels where they adhere to glycolipid ligand molecules on the surface of white blood cells. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from acute physical trauma may be treated with formulations of the invention in order to relieve the amount of inflammation and swelling which normally result after an area of the body is subjected to severe trauma. Other conditions treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Various compositions comprising of: (1) a myelorollin: (A) Fr. 10-2, (B) a mixture of Fr. 10-1 and Fr. 10-2, or (C) Fr. 14, and (2) a pharmaceutically acceptable carrier such as, but not limited to: (D) polyalkylene glycol, (E) triglyceride, (F) fatty oil, (G) synthetic fatty acid ester, (H) liposome, (I) carboxymethyl cellulose, (J) sorbitol, or (K) dextran are administered in a therapeutically effective dosages thereof to patients suffering from an inflammatory disease such as, but not limited to, arthritis, rheumatoid arthritis, multiple sclerosis. These administrations are useful in curing ameliorating such diseases.

EXAMPLE

Introduction

The cloning in 1989 (Bevilacqua et al. 1989, Science 243:1160–1165; Johnston et al., 1989, Cell 56:1033–1044) of cDNA encoding vascular or platelet adhesive proteins, now termed E- and P-selectins, has led to focused attempts to identify carbohydrate epitopes which are expressed on leukocytes (see for review Varki, A., 1994, Proc. Natl. Acad. Sci. USA 91:7390–7397; Lasky, L. A. ,1995, Ann. Rev. Biochem. 64, 113–139) and function as targets of selectin-dependent "rolling" and adhesion of leukocytes on activated endothelial cells (ECs[1]), followed by transendothelial migration. This mechanism plays a central role in inflammatory responses (Lasky, L. A. ,1995, Ann. Rev. Biochem. 64:113–139). Such epitopes are involved in recruitment of the cells to inflammatory sites following infection or wounding. Sialosyl-Le$^x$ (SLe$^x$) is generally believed to be the target epitope of E-selectin binding, based on the following claims: (i) Human leukocytes, leukemic leukocytes, and their cell lines, which react with various mAbs claimed to be directed to SLe$^x$, are capable of binding to E- and P-selectin expressed at the surface of activated ECs and platelets (Ito et al., 1994, Glycoconj. J. 11:232–237; Phillips et al., 1990, Science 250:1130–1132; Polley et al., 1991, Proc. Natl. Acad. Sci. USA 88:6224–6228). (iii) Chinese Hamster Ovary (CHO) cells expressing sialosyl type 2 chain do not adhere to E-selectin, whereas transfectants of these cells with fucosyltransferase III cDNA do adhere to E-selectin (Lowe et al., 1990, Cell 63:475–484). (iv) E-selectin-dependent adhesion of SLe$^x$-expressing cells to activated ECs or platelets is inhibited by liposomes containing SLe$^x$ GSLs, or by oligosaccharides with terminal SLe$^x$ structure (Phillips et al., 1990, Science 250:1130–1132; Polley et al., 1991, Proc. Natl. Acad. Sci. USA 88:6224–6228; Handa et al., 1991, Biochem. Biophys. Res. Comm. 181:1223–1230).

There has been no chemical characterization of SLe$^x$-containing gangliosides present in neutrophils and HL60 cells, nor any unambiguous demonstration that SLe$^x$ is the major epitope present in N-linked or 0-linked glycoprotein side chains in normal or leukemic leukocytes or cell lines derived therefrom (see Discussion).

We recently characterized monosialogangliosides of HL60 cells and human neutrophils which bind (or do not bind) to E-selectin under static conditions (Stroud et al., 1995, Biochem. Biophys. Res. Comm. 209:777–787; Stroud et al., 1996, Biochemistry 35:758–769). There was no SLe$^x$ structure, with or without internal fucosylation, having <10-sugar monosaccharide units as poly-LacNAc core structure (Stroud et al., 1996, Biochemistry 35:758–769). All the E-selectin binding fractions had $\alpha 2 \rightarrow 3$ sialosylation at the terminal Gal and two or more $\alpha 1 \rightarrow 3$ fucosylations at internal GlcNAc other than the penultimate (Stroud et al., 1995, Biochem. Biophys. Res. Comm. 209:777–787; Stroud et al., 1996, Biochemistry 35:770–778). These binding fractions were collectively termed "myeloglycan." There was an extremely minor component of poly-LacNAc having SLe$^x$ terminus with α1→3 fucosylation at internal GlcNAc. We concluded that the major E-selectin binding site in human neutrophils and HL60 cells is myeloglycan type rather than SLe$^x$-containing glycan. None of the myeloglycan or poly-LacNAc SLe$^x$ structures examined showed P-selectin binding (Stroud et al., 1996, Biochemistry 35:758–769; Stroud et al., 1996, Biochemistry 35:770–778).

These results under static conditions are now compared with rolling and adhesive behavior of the same cells under dynamic flow conditions, using a parallel-plate laminar-flow chamber based on the design by Lawrence et al. (Lawrence et al., 1990, Blood 75:227–237; Lawrence and Springer, 1991, Cell 65:859–873). In this experimental system, sialosyl poly-LacNAc with internal α1→3 fucosylation, regardless of position and number of substitutions at internal GlcNAc, produced strong cell rolling/adhesion. A mixture of two sialosyl poly-LacNAc structures with α1→3 fucosylation of GlcNAc at different locations (hereby termed "myelorollin") produced consistently stronger rolling/adhesion than either structure alone, particularly at very low dose (0.05 or 0.1 ng).

MATERIALS AND METHODS

GSLs and monosialogangliosides

Monosialoganglioside fractions used for adhesion assay presented in this EXAMPLE are shown in FIG. 8. Structures were verified by $^1$H-NMR, $^+$ion FABMS, and ES-MS with CID of permethylated compounds as described previously (Stroud et al., 1995, Biochem. Biophys. Res. Comm. 209:777–787; Stroud et al., 1996, Biochemistry 35:758–769; Stroud et al., 1996, Biochemistry 35:770–778). Structures of Fr. 9-1, 9-2, 10-1, and 10-2 were further confirmed by endo-β-galactosidase digestion (Fukuda et al., 1979, J. Biol. Chem. 254:5458–5465), methylation analysis, and $^+$ion FABMS.

Cells and binding assay

CHO cells transfected with E-selectin cDNA were established as described previously (Handa et al., 1995, Int. J. Oncol. 6:773–781). E-selectin-expressing transfectants were isolated by cytofluorometry using anti-E-selectin mAb E1A. Inhibition of E-selectin-dependent cell adhesion was performed using anti-E-selectin mAb E1C at 10 μg/mL concentration. These mAbs were established through immunization of BALB/c mice with E-selectin-expressing NS1 cells.

E-selectin-dependent cell binding to various GSLs under static conditions

Static adhesion assay using 96-well plates: Poly-LacNAc gangliosides with SLe$^x$-Le$^x$ structure, and Fr. 9, 10-1, 10-2, and 12-2, dissolved in 50% ethanol, were serially diluted in 96-well plates (the first well contained 250–500 ng), and plates were dried at 37° C. for 5 hr. Plates with similar serial dilutions of poly-LacNAc gangliosides were prepared for control cell adhesion in the presence of mAb E1C 15 μg/mL (see above). E-selectin-expressing CHO cells (Handa et al., 1995, Int. J. Oncol. 6:773–781) were metabolically labeled with [$^3$H]thymidine and incubated for 2 days. Cell suspension (2×10$^6$ per mL) was prepared by 2 mM EDTA treatment of cultured cells. A 50 μL aliquot of this cell suspension (containing 1×10$^5$ cells; about 5000 cpm) was added to each well and incubated for 1 hr. As a control, EDTA-harvested cells were washed with DMEM and incubated with mAb E1C (10 μg/ml) on ice for 30 min, followed by preparation of cell suspension as above, but containing 10 μg E1C per mL. Aliquots were added to each well and incubated as above. Cells were washed 3× with PBS by inversion of the plate on blotting paper. Adherent cell count as measured by $^3$H activity was determined (see FIG. 1A legend).

Static adhesion assay using polystyrene latex beads: In order to observe static adhesion with the same matrix used for dynamic adhesion assay, the following procedure was used. Polystyrene latex beads of 1 μm or 4 μm diameter (IDC Spheres™; IDC, Portland, Oreg.), affixed to objective microscope slides, were used as carriers of poly-LacNAc GSLs. 30 μL of the 4 μm diameter bead suspension (containing 2×10$^9$ beads/mL) or 60 μL of 1 μm bead suspension (containing 1×10$^{11}$ beads/mL) were placed in Eppendorf tubes and washed with absolute ethanol 3×. Sedimented 4 μm beads were suspended in 500 mL ethanol, and sedimented 1 μm beads were suspended in 2 mL ethanol. 1 μL aliquots of these suspensions were placed on freshly opened microscope slides (Labcraft Superfrost® Plus, Curtin Matheson Scientific, Houston, Tex.). Beads were distributed homogeneously on the glass surface within a circular spot with diameter ≈1 cm. Slides were heated at 150° C. for 50 sec, which caused the beads to adhere strongly to the surface such that they could not be washed off by water stream at various velocities. Gangliosides dissolved in isopropanol-hexane-water at the same molar concentration were applied to latex beads affixed to the slides; namely, 1 μL aliquots containing 50–100 ng ganglioside were placed on the center of the circular spot. The ganglioside thus became affixed to the bead surface. Plates were immersed in 3% BSA in PBS for 1 hr at room temp, and washed 3× with PBS containing Ca$^{2+}$/Mg$^{2+}$.

Plates were overlaid with 5×10$^5$ CHO cells freshly harvested and suspended in RPMI culture medium for 15 min without moving. Washing with RPMI 3× was usually sufficient to eliminate non-adherent cells from beads. However, careful microscopic examination had to be repeated until the cells placed on control polystyrene beads were washed out. Plates were then fixed with 1% glutaraldehyde in PBS and number of cells adhered to the layer of poly-LacNAc ganglioside-coated beads were counted.

E-selectin-dependent cell binding to various GSLs under dynamic flow conditions

Slides prepared as above were incubated with 3% BSA prewarmed to 37° C., incubated at that temperature for at least 1 hr, and washed with PBS containing Ca$^{2+}$/Mg$^{2+}$. Slides were placed in a parallel plate laminar flow chamber connected to an infusion pump (model 935, Harvard Apparatus, Cambridge, Mass.). The assembly, originally described by Lawrence et al. (Lawrence et al., 1990, Blood 75:227–237; Lawrence and Springer, 1991, Cell 65:859–873) simulates the flow shear stress present in physiological microvascular environments. A laminar flow with defined rate and wall shear stress is achieved by manipulation of the infusion pump, which is connected to the inlet of the flow chamber. A suspension of E-or P-selectin-expressing CHO cells (1×10$^5$/cells mL), freshly harvested from culture with EDTA, washed, and resuspended in 1% FCS-RPMI medium, was infused into the assembly at various laminar flow rates. Cell movements were observed under inverted phase-contrast microscope (Diaphot-TMD, Nikon) and recorded by time-lapse videocassette recorder. Cell rolling and adhesion were observed, and numbers of rolling and adherent cells during a 2 min period at shear stresses from 0.4 to 4.8 dynes/cm$^2$ were counted from at least 10 fields on videotape. Wall shear stress (T) was calculated by the equation of Lawrence et al. (Lawrence et al., 1990, Blood 75:227–237; Lawrence et al., 1987, Blood 70:1284–1290):

$$T = 3\mu Q / 2ba^2$$

where $\mu$=coefficient of viscosity (1.0 cP), Q=volumetric flow rate (cm$^3$/sec), a=half channel height (in this case, $5.7 \times 10^{-3}$ cm), and b=channel width (1.3 cm).

RESULTS

Adhesion of E-selectin-expressing CHO cells to myeloglycan analogs and SLe$^x$-Le$^x$ under static conditions Adhesion of E-selectin-expressing CHO cells to various poly-LacNAc gangliosides with myeloglycan analogs and SLe$^x$-containing structures was examined under the conditions described in Materials & Methods. These conditions allowed adhesion of various gangliosides to polystyrene microsphere beads (diameter 1 mm) affixed to microscope slides. $10^5$/mL E-selectin-expressing CHO cells were overlaid and left for 10 min, followed by washing and counting of cell number. These static adhesion conditions were ideal for comparison with our dynamic flow system, since the matrices on which gangliosides adhered were identical. SLe$^x$-Le$^x$ (VI$^3$NeuAcV$^3$FucIII$^3$FucnLc$_6$Cer; Str. 1 in FIG. 8) showed slightly higher adhesion than Fr. 13-1 (X$^3$NeuAcVII$^3$FucV$^3$FucnLc$_{10}$Cer; Str. 2 in FIG. 8). Fr. 14 (a mixture of myeloglycan and other poly-LacNAc gangliosides; Str. 3, 4, 5, and 6 in FIG. 8) showed moderate adhesion (slightly lower than SLe$^x$-Le$^x$). Under the same conditions, Fr. 10-1 (VIII$^3$NeuAcV$^3$FucnLc$_8$Cer; Str. 7 in FIG. 8), Fr. 10-2 (VIII$^3$NeuAcIII$^3$FucnLc$_8$Cer; Str. 8 in FIG. 8), and Fr. 12-2 (X$^3$NeuAcVII$^3$ FucnLc$_{10}$Cer) showed much weaker adhesion than Fr. 13-1 or Fr. 14 (FIG. 1B). See also Table 3 which provides value, for data shown in FIG. 1A. Sialosyls poly-LacNAc without internal fucosylation (e.g. VI$^3$NeuAcnLc$_6$Cer; Fr. 7) showed no adhesion.

Myeloglycan analogs showed higher E-selectin-dependent rolling/adhesion than SLe$^x$-Le$^x$ under dynamic flow conditions at physiological shear stress 100 ng of poly-LacNAc ganglioside (Fr. 13-1, Fr. 14, or SLe$^x$-Le$^x$) was adhered to beads affixed to microscope slides, which were then placed in a dynamic flow system as described in Materials & Methods. We observed rolling/adhesion of E-selectin-expressing CHO cells in this system at various shear stresses. Trends of adhesion of poly-LacNAc gangliosides to beads with diameter 4 $\mu$m or 1 $\mu$m were essentially similar (FIGS. 2B, 2C). Fr. 13-1 and Fr. 14 produced strong rolling/adhesion at 4.8 or 2.4 dynes/cm$^2$. Number of rolling cells was lower at 1.2 dynes/cm$^2$ (FIGS. 2B, 2C, 2D). Number of adhering cells on beads coated with SLe$^x$-Le$^x$ was significantly lower than for Fr. 13-1 or 14. No rolling was observed with SLe$^x$-Le$^x$ (FIG. 2A).

An artificial mixture of Fr. 10-1 and 10-2 enhanced rolling/adhesion under dynamic flow conditions Fr. 10-1 and 10-2 were characterized as poly-LacNAc gangliosides having $\alpha 1 \rightarrow 3$ fucosylation at GlcNAc-V and GlcNAc-II respectively. 100 ng of either fraction adhered to beads affixed to slides showed comparable adhesion at 4.8 and 2.4 dynes/cm (FIG. 3A, plots 1 and 2). An artificial mixture of 50 ng each of Fr. 10-1 and 10-2 produced much higher rolling/adhesion at these shear stresses (plot 3). Statistical significances of differences between plots (P value from unpaired Student's t-test) are shown in the inset table on FIG. 3A.

Enhancement of rolling/adhesion by a mixture of 10-1 and 10-2 as compared to either fraction alone was more evident when a 1000-fold smaller concentration was used (FIG. 3B). 10-2 at this small concentration (0.1 ng per spot) still produced marked rolling/adhesion (FIG. 3B, plot 2), but 10-1 did not (plot 1). Much higher rolling/adhesion at physiological shear stress (2.4–4.8 dynes/cm$^2$) was observed when a mixture of 0.05 ng each of 10-1 and 10-2 was used (plot 3). Statistical significances between plots (P value from unpaired Student's t-test) are shown in the inset table on FIG. 3B.

DISCUSSION

Expression of E- and P-selectin on ECs in response to inflammatory stimuli causes interaction of ECs with neutrophils or other leukocytes, resulting in rolling followed by adhesion and transendothelial migration of leukocytes. E-selectin-dependent adhesion has been thought to be mediated by recognition of SLe$^x$ epitope expressed on leukocytes by E-selectin. This concept was based on various observations (see Introduction). These observations, however, did not include unequivocal chemical identification of the real carbohydrate epitope present on neutrophils. Human neutrophils, other leukocytes, and leukemic leukocyte cell lines (HL60 and U937) show strong reactivity with various mAbs previously claimed to be directed to SLe$^x$. However, quantities of SLe$^x$ chemically detectable in these cells are extremely small. $^+$ion FABMS of permethylated side chains of N-linked structures in leukemic leukocytes gave a barely detectable m/z 999 signal, representing SLe$^x$ structure (Fukuda et al., 1984, J. Biol. Chem. 259:10925–10935). The presence of SLe$^x$ in side chains of N- or O-linked structures in neutrophils or myelogenous leukemia cells was assumed (Asada et al., 1991, Biochemistry 30:1561–1571; Patel et al., 1994, Biochemistry 33:14815–14824), but not supported by unambiguous chemical analysis. Our recent systematic studies on gangliosides of normal human leukocytes and HL60 cells indicated that only unbranched monosialogangliosides having cores with >10 sugars are responsible for E-selectin binding (Stroud et al., 1995, Biochem. Biophys. Res. Commun. 209:777–787; Stroud et al., 1996, Biochemistry 35:758–769; Stroud et al., 1996, Biochemistry 35:770–778). Gangliosides with SLe$^x$ structure (e.g. IV$^3$NeuAcIII$^3$FucnLc$_4$Cer, VI$^3$NeuAcV$^3$FucnLc$_6$Cer, VI$^3$NeuAcV$^3$FucIII$^3$FucnLc$_6$Cer), which are abundantly present in various types of solid human cancer (Yang and Hakomori, 1971, J. Biol. Chem. 246:1192–1200; Fukushi et al., 1984, J. Biol. Chem. 259:10511–10517), were completely absent from leukocytes and HL60 cells (Stroud et al., 1996, Biochemistry 35:758–769). Among long-chain PLA lipids having 8-, 10-, or 12-sugar cores, structures having SLe$^x$ epitope without internal fucosylation (e.g. VIII$^3$NeuAcVII$^3$FucnLc$_8$Cer, X$^3$NeuAcIX$^3$FucnLc$_{10}$Cer, XII$^3$NeuAcXI$^3$FucnLc$_{12}$Cer) were completely absent. Instead, there were trace components having SLe$^x$ with internal fucosylation (e.g. X$^3$NeuAcIX$^3$FucVII$^3$FucnLc$_{10}$Cer) (Stroud et al., 1996, Biochemistry 35:770–778). The major structures present in leukocytes and HL60 cells were a series of unbranched, long-chain PLAs having terminal $\alpha 2 \rightarrow 3$ sialylation and internal $\alpha 1 \rightarrow 3$ fucosylation, with the structures A, B, C, and D shown below (Stroud et al., 1996, Biochemistry 35:758–769; Stroud et al., 1996, Biochemistry 35:770–778).

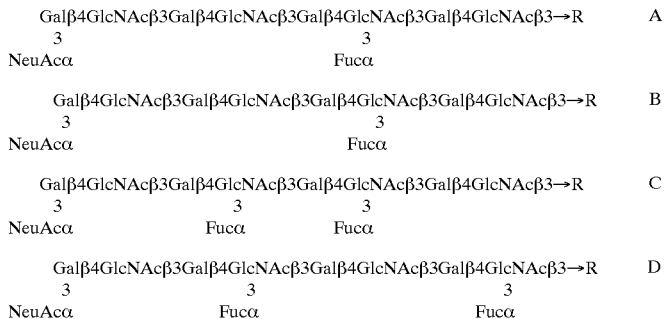

A is common to Str. 3 and 7 in FIG. 8. B is common to Str. 4 and 8. C is common to Str. 2 and 5 in FIG. 8. D is found in Str. 6 in FIG. 8. None of these four structures contains $SLe^x$ epitope. A was previously found in gangliosides isolated from chronic myelogenous leukemia cells (Fukuda et al., 1984, J. Biol. Chem. 259:10925–10935) and from human colonic cancer, and was identified as ACFH-18 antigen (Nudelman et al., 1988, J. Biol. Chem. 263:13942–13951). A was also identified as being defined by mAb "VIM-2" (Macher et al., 1988, J. Biol. Chem. 263, 10186–10191), and was once claimed to be the E-selectin binding epitope (Tiemeyer et al., 1991, Proc. Natl. Acad. Sci. USA 88:1138–1142). However, because VIM-2-positive, $SLe^x$-negative CHO cells showed no E-selectin-dependent adhesion (Lowe et al., 1990, Cell 63:475–484), VIM-2 epitope was considered not to be involved in such adhesion.

In our previous study, only fractions with terminal $\alpha 2 \rightarrow 3$ sialylation and multiple internal $\alpha 1 \rightarrow 3$ polyfucosylation (e.g. C and D above, or a mixture of these structures) showed clear E-selectin binding upon application of TLC overlay technique with $^{32}$p-labeled CHO cells permanently expressing E- or P-selectin (Stroud et al., 1996, Biochemistry 35:758–769; Stroud et al., 1996, Biochemistry 35:770–778). Poly-LacNAc with terminal $\alpha 2 \rightarrow 3$ sialylation and internal $\alpha 1 \rightarrow 3$ monofucosylation (e.g. A and B) did not show E-selectin binding under these conditions. These binding properties were confirmed in a static binding assay system using E-selectin-expressing CHO cells overlaid on glycolipids coated on polystyrene beads affixed to glass plates. Glycolipid with typical $SLe^x$ structure ($SLe^x$-$Le^x$; $VI^3NeuAcV^3FucIII^3FucnLc_6Cer$) showed highest binding in the static system. In contrast, in a dynamic flow system using the same glycolipid-coated beads affixed to glass plates, $SLe^x$-$Le^x$ produced no rolling and relatively weak adhesion compared to Fr. 10-1, 10-2, 13-1, and 14. Strong rolling/adhesion of cells were observed when structures A and B were used. Typical examples are Fr. 10-1 and 10-2. Fr. 13-1 (pure myeloglycan type with structure C) and Fr. 14 (mixture of A, B, C, D) also produced strong rolling/adhesion under physiological shear stress conditions.

Given the finding that a mixture of myeloglycan and myelorollin structures (e.g. Fr. 14) produces the strongest rolling/adhesion under physiological shear stress conditions, we closely investigated Fr. 10-1 (Str. 7 in FIG. 8), Fr. 10-2 (Str. 8 in FIG. 8), and a mixture of equal quantities of 10-1 and 10-2. Rolling/adhesion caused by 100 ng of pure 10-1 and 10-2 under physiological shear stress were comparable. Interestingly, a mixture of 50 ng each of these two components produced much higher rolling/adhesion, particularly under physiological shear stress. This trend was more evident when much smaller quantities of glycolipids were applied. The most dramatic enhancement was seen when 0.05 ng each of 10-1 and 10-2 were used, compared to 0.1 ng of either component alone. These findings suggest that extremely small quantities of 10-1 and 10-2 may interact with each other to form a binding site for E-selectin with higher affinity. The molecular mechanism for this synergistic effect remains unknown.

$SLe^x$-$Le^x$ structure, which produced the strongest E-selectin-dependent adhesion under static conditions, was weaker than myeloglycan or myelorollin structures under dynamic flow conditions (FIGS. 2A vs. 2B and 2C). The difference was even more striking at very low doses. $SLe^x$-$Le^x$ at a dose of 0.05 ng caused essentially no cell rolling/adhesion (FIG. 4A), whereas a mixture of Fr. 10-1 and 10-2 (0.05 ng each, giving the same molarity as 0.05 ng $SLe^x$-$Le^x$) caused strong rolling/adhesion (FIG. 4B). These results support the hypothesis that mixtures of myeloglycan or myelorollin structures, rather than $SLe^x$, are the ligands for E-selectin-dependent rolling/adhesion of HL60 cells and human neutrophils.

Our results also suggest an explanation of why a series of poly-LacNAc structures with differing location of $\alpha 1 \rightarrow 3$ fucosylation, and terminal sialylation, are present and form arrays on the neutrophil surface. Combinations of specific structures may form high-, middle-, or low-affinity binding sites in order to optimally bind E-selectin under high-, middle-, or low-shear stress dynamic flow conditions. Poly-LacNAc is known to form helical structures. Myelorollin and myeloglycan may have helical backbone structures onto which multiple or single fucosyl residues are linked and oriented in different directions. Such helical structures, based on the positioning of the fucosyl residues, could interact with each other.

CITATIONS

1. Varki, A. (1994) *Proc. Natl. Acad. Sci.* USA 91, 7390–7397
2. Lasky, L. A. (1995) *Ann. Rev. Biochem.* 64, 113–139
3. Ito, K., Handa, K., and Hakomori, S. (1994) *Glycoconj. J.* 11, 232–237
4. Phillips, M. L., Nudelman, E. D., Gaeta, F. C. A., Perez, M., Singhal, A. K., Hakomori, S., and Paulson, J. C. (1990) *Science* 250, 1130–1132
5. Polley, M. J., Phillips, M. L., Wayner, E. A., Nudelman, E. D., Singhal, A. K., Hakomori, S., and Paulson, J. C. (1991) *Proc. Natl. Acad. Sci. USA* 88, 6224–6228
6. Lowe, J. B., Kukpwska-Latello, J. F., Nair, R. P., Larsen, R. D., Marks, R. M., Macher, B. A., Kelley, R. J., and Ernst, L. K. (1991) *J. Biol. Chem.* 266, 17467–17477
6a. Walz, G., Aruffo, A., Kolanus, W., Bevilacqua, M. P., and Seed, B. (1990) *Science* 250, 1132–1135
7. Handa, K., Nudelman, E. D., Stroud, M. R., Shiozawa, T., and Hakomori, S. (1991) *Biochem. Biophys. Res. Commun.* 181, 1223–1230

8. Berg, E. L., Robinson, M. K., Mansson, O., Butcher, E. C., and Magnani, J. L. (1991) *J. Biol. Chem.* 266, 14869–14872
9. Takada, A., Ohmori, K., Takahashi, N., Tsuyuoka, K., Yago, A., Zenita, K., Hasegawa, A., and Kannagi, R. (1991) *Biochem. Biophys. Res. Commun.* 179, 713–719
10. Stroud, M. R., Handa, K., Ito, K., Salyan, M. E. K., Fang, H., Levery, S. B., Hakomori, S., Reinhold, B. B., and Reinhold, V. N. (1995) *Biochem. Biophys. Res. Commun.* 209, 777–787
11. Handa, K., White, T., Ito, K., Fang, H., Wang, S., and Hakomori, S. (1995) *Int. J. Oncol.* 6, 773–781
12. Lawrence, M. B., Smith, C. W., Eskin, S. G., and McIntire, L. V. (1990) *Blood* 75, 227–237
13. Lawrence, M. B. and Springer, T. A. (1991) *Cell* 65, 859–873
14. Lawrence, M. B., McIntire, L. V., and Eskin, S. G. (1987) *Blood* 70, 1284–1290
15. Fukuda, M., Spooncer, E., Oates, J. E., Dell, A., and Klock, J. C. (1984) *J. Biol. Chem.* 259, 10925–10935
16. Asada, M., Furukawa, K., Kantor, C., Gahmberg, C. G., and Kobata, A. (1991) *Biochemistry* 30, 1561–1571
17. Patel, T. P., Goelz, S. E., Lobb, R. R., and Parekh, R. B. (1994) *Biochemistry* 33, 14815–14824
18. Yang, H.-J. and Hakomori, S. (1971) *J. Biol. Chem.* 246, 1192–1200
19. Fukushi, Y., Nudelman, E. D., Levery, S. B., Rauvala, H., and Hakomori, S. (1984) *J. Biol. Chem.* 259, 10511–10517
20. Nudelman, E. D. Levery, S. B., Stroud, M. R., Salyan, M. E. K., Abe, K., and Hakomori, S. (1988) *J. Biol. Chem.* 263, 13942 13951
21. Macher, B. A., Buehler, J., Scudder, P., Knapp, W., and Feizi, T. (1988) *J. Biol. Chem.* 263, 10186–10191
22. Tiemeyer, M., Swiedler, S. J., Ishihara, M., Moreland, M., Schweingruber, H., Hirtzer, P., and Brandley, B. K. (1991) *Proc. Natl. Acad. Sci. USA* 88, 1138–1142
23. Fukushima, K., Hirota, M., Terasaki, P. I., Wakisaka, A., Togashi, H., Chia, D., Suyama, N., Fukushi, Y., Nudelman, E. D., and Hakomori, S. (1984) *Cancer Res.* 44, 5279–5285
24. Muroi, K., Suda, T., Nojiri, H., Ema, H., Amemiya, Y., Miura, Y., Nakauchi, H., Singhal, A. K., and Hakomori, S. (1992) *Blood* 79, 713–719
25. Sako, D., Chang, X.-J., Barone, K. M., Vachino, G., White, H. M., Shaw, G., Veldman, G. M., Bean, K. M., Ahern, T. J., Furie, B., Cumming, D. A., and Larsen, G. R. (1993) *Cell* 75, 1179–1186
26. Niemann, H., Watanabe, K., and Hakomori, S. (1978) *Biochem. Biophys. Res. Commun.* 81, 1286–1293
27. Rees, D. A. (1975) MTP International Review of Science 5, 1 42, ed. Whelan, W., Butterworths (London) University Park Press (Baltimore); Atkins, E. D. T., Isaac, D. H., Nieduszynski, I. A., Phelps, C. E., and Sheehan, J. K. (1974) *Polymer* 15, 263–271.

While the preferred embodiment of the invention has been illustrated and described, it will be appreciated that various changes can be made therein without departing from the spirit an scope of the invention.

Various publications are cited herein, the disclosures of which are incorporated by reference in their entireties.

What is claimed is:

1. An antibody that specifically binds a myelorollin comprising:

(A)
$$\begin{array}{c} \text{Gal}\beta\text{4GlcNAc}\beta\text{3Gal}\beta\text{4GlcNAc}\beta\text{3Gal}\beta\text{4GlcNAc}\beta\rightarrow R \\ 3 \qquad\qquad\qquad\qquad 3 \\ \text{NeuAc}\alpha 2 \qquad\qquad\qquad\qquad \text{Fuc}\alpha \end{array}$$

or (B)
$$\begin{array}{c} \text{Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\rightarrow R \\ 3 \qquad\qquad\qquad\qquad\qquad\qquad 3 \\ \text{NeuAc}\alpha 2 \qquad\qquad\qquad\qquad\qquad\qquad \text{Fuc}\alpha \end{array}$$

wherein R comprises a H atom, a substituted or unsubstituted aryl group, an alkyl, alkenyl or hydroxyalkyl group having 1 to 10 carbon atoms, a complex lipid, a simple lipid, an oligosaccharide which does not contain any lactosamine residue, a ceramide residue, a pharmaceutically active ingredient, a solid carrier or a covalent compound thereof.

2. An antibody that specifically binds a myelorollin comprising:

(A)
$$\begin{array}{c} \text{Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\rightarrow R \\ 3 \qquad\qquad\qquad\qquad\qquad\qquad\qquad\qquad 3 \\ \text{NeuAc}\alpha 2 \qquad\qquad\qquad\qquad\qquad\qquad\qquad\qquad \text{Fuc}\alpha \end{array}$$

or (B)
$$\begin{array}{c} \text{Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\rightarrow R \\ 3 \qquad\qquad\qquad 3 \qquad\qquad\qquad 3 \\ \text{NeuAc}\alpha 2 \qquad\qquad \text{Fuc}\alpha \qquad\qquad \text{Fuc}\alpha \end{array}$$

or (C)
$$\begin{array}{c} \text{Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\rightarrow R \\ 3 \qquad\qquad\qquad\qquad 3 \qquad\qquad\qquad 3 \\ \text{NeuAc}\alpha 2 \qquad\qquad\qquad \text{Fuc}\alpha \qquad\qquad \text{Fuc}\alpha \end{array}$$

wherein R comprises a H atom, a substituted or unsubstituted aryl group, an alkyl, alkenyl or hydroxyalkyl group having 1 to 10 carbon atoms, a complex lipid, a simple lipid, an oligosaccharide, a ceramide residue, a pharmaceutically active ingredient, a solid carrier or a covalent compound thereof.

3. An antibody that specifically binds a myelorollin comprising:

$$\begin{array}{ll}\text{Gal}\beta\text{4GlcNAc}\beta\text{3Gal}\beta\text{4GlcNAc}\beta\text{3Gal}\beta\text{4GlcNAc}\beta\text{3Gal}\beta\text{4Glc}\beta\rightarrow\text{R} & \text{(A)}\\ \quad\quad\quad\; 3 \quad\quad\quad\quad\quad\quad\quad\quad\quad\quad\;\; 3 \\ \text{NeuAc}\alpha 2 \quad\quad\quad\quad\quad\quad\quad\quad\quad\;\; \text{Fuc}\alpha\end{array}$$

or $$\begin{array}{ll}\text{Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\text{3Gal}\beta\text{4Glc}\beta\rightarrow\text{R} & \text{(B)}\\ \quad\quad\quad\; 3 \quad\quad\quad\quad\quad\quad\quad\quad\quad\quad\quad\quad\quad\quad\quad\;\; 3 \\ \text{NeuAc}\alpha 2 \quad\quad\quad\quad\quad\quad\quad\quad\quad\quad\quad\quad\quad\quad\; \text{Fuc}\alpha\end{array}$$

or $$\begin{array}{ll}\text{Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\text{3Gal}\beta\text{4Glc}\beta\rightarrow\text{R} & \text{(C)}\\ \quad\quad\quad\; 3 \quad\quad\quad\quad\quad\quad\quad 3 \quad\quad\quad\quad\quad\quad 3 \\ \text{NeuAc}\alpha 2 \quad\quad\quad\quad\quad\; \text{Fuc}\alpha \quad\quad\quad\quad\; \text{Fuc}\alpha\end{array}$$

or $$\begin{array}{ll}\text{Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\text{3Gal}\beta\text{4GlcNAc}\beta\text{3Gal}\beta\text{4Glc}\beta\rightarrow\text{R} & \text{(D)}\\ \quad\quad\quad\; 3 \quad\quad\quad\quad\quad\quad\quad 3 \quad\quad\quad\quad\quad\quad\quad\quad\quad\quad\quad 3 \\ \text{NeuAc}\alpha 2 \quad\quad\quad\quad\quad\; \text{Fuc}\alpha \quad\quad\quad\quad\quad\quad\quad\quad\quad \text{Fuc}\alpha\end{array}$$

wherein R is a ceramide residue.

4. A method for inhibiting E-selectin-dependent rolling of a first cell on a second cell, comprising exposing the first cell and/or the second cell to an effective amount of the antibody of any one of claims 1–3 which inhibits the rolling; wherein the first cell expresses a myelorollin that causes E-selectin-dependent rolling and that binds the antibody, and the second cell expresses E-selectin.

5. The method according to claim 4, wherein the first cell is a leukocyte or leukemic cell.

6. The method according to claim 4, wherein the first cell is neutrophil or human promyelogenous leukemia HL60 cell.

* * * * *